United States Patent
Kawana et al.

(10) Patent No.: US 9,617,240 B2
(45) Date of Patent: Apr. 11, 2017

(54) PYRAZOLE DERIVATIVE

(71) Applicant: TEIJIN PHARMA LIMITED, Tokyo (JP)

(72) Inventors: Asahi Kawana, Hino (JP); Chikashi Kanazawa, Hino (JP); Masayuki Tera, Takatsuki (JP); Yoshimasa Takahashi, Hino (JP); Mariko Imazeki, Tokyo (JP); Hiroyuki Takahashi, Hino (JP); Akira Tanokura, Hino (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 0 days.

(21) Appl. No.: 14/774,517

(22) PCT Filed: Mar. 28, 2014

(86) PCT No.: PCT/JP2014/059912
§ 371 (c)(1),
(2) Date: Sep. 10, 2015

(87) PCT Pub. No.: WO2014/157740
PCT Pub. Date: Oct. 2, 2014

(65) Prior Publication Data
US 2016/0039784 A1  Feb. 11, 2016

(30) Foreign Application Priority Data
Mar. 29, 2013 (JP) ................................ 2013-072788

(51) Int. Cl.
| | | |
|---|---|---|
| C07D 401/04 | (2006.01) |
| C07D 401/14 | (2006.01) |
| C07D 405/14 | (2006.01) |
| C07D 409/14 | (2006.01) |

(52) U.S. Cl.
CPC ......... *C07D 401/04* (2013.01); *C07D 401/14* (2013.01); *C07D 405/14* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 4,495,195 A | 1/1985 | Beck et al. | |
| 6,015,829 A | 1/2000 | Ishibuchi et al. | |
| 7,816,558 B2 * | 10/2010 | Sato | C07D 213/79 546/318 |
| 2009/0018104 A1 | 1/2009 | Sato et al. | |
| 2009/0036428 A1 | 2/2009 | Kawakami et al. | |
| 2009/0306396 A1 | 12/2009 | Toyoshima et al. | |
| 2012/0184582 A1 | 7/2012 | Song et al. | |

FOREIGN PATENT DOCUMENTS

| | | |
|---|---|---|
| EP | 0 048 615 A1 | 3/1982 |
| EP | 1 932 833 A1 | 6/2008 |
| JP | 59-95272 A | 6/1984 |
| JP | 10-310578 A | 11/1998 |
| WO | 98/18765 A1 | 5/1998 |
| WO | 99/55693 A1 | 11/1999 |
| WO | 2005/111003 A1 | 11/2005 |
| WO | 2007/043400 A1 | 4/2007 |
| WO | 2007/043457 A1 | 4/2007 |
| WO | 2007/097403 A1 | 8/2007 |
| WO | 2007/113226 A1 | 10/2007 |
| WO | 2008/126770 A1 | 10/2008 |

(Continued)

OTHER PUBLICATIONS

Thomas Cailly et al., "Regioselective functionalization of 2-(2'-fluorophenyl)-3-cyanopyridine and its cyclization to benzo[*h*]-1,6-naphthyridines", Tetrahedron, 2010, pp. 1299-1307, vol. 66.

M. Tutonda et al., "Diels-Alder Reactions of the Heterodiene System in 2(1H)-Pyrazinones", Tetrahedron Letters, 1986, pp. 2509-2512, vol. 27, No. 22.

Database Registry, 2011, [online] Retrieved on Jun. 3, 2014, 17pgs.

Namal C. Warshakoon et al., "Design and synthesis of substituted pyridine derivatives as HIF-1α prolyl hydroxylase inhibitors", Bioorganic & Medicinal Chemistry Letters, 2006, pp. 5616-5620, vol. 16.

(Continued)

*Primary Examiner* — Timothy R Rozof
(74) *Attorney, Agent, or Firm* — Sughrue Mion, PLLC

(57) ABSTRACT

Provided are a compound expressed by formula (I) or a pharmacologically permissible salt thereof, as well as a drug or drug composition that contains this compound as an active ingredient, having a xanthine oxidase inhibiting effect that is very useful for treating or preventing diseases that are contributed to by xanthine oxidase, such as gout, hyperuricemia, tumor lysis syndrome, urinary tract stones, hypertension, dyslipidemia, diabetes, cardiovascular disease such as heart failure and arterial sclerosis, renal disease such as diabetic near opacity and the like, respiratory disease such as chronic obstructive pulmonary disease and the like, autoimmune diseases such as inflammatory bowel disease, and the like. [In the formula, A, X, Y, Z, R, and $R^1$ have the meaning set forth in claim 1].

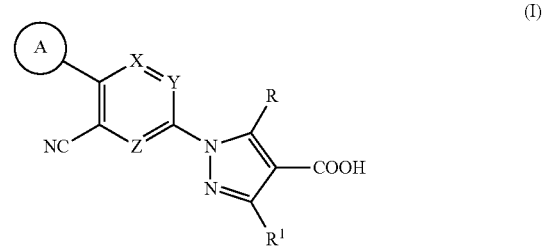

(I)

19 Claims, No Drawings

(56) References Cited

FOREIGN PATENT DOCUMENTS

| WO | 2008/126772 A1 | 10/2008 |
| WO | 2010/044403 A1 | 4/2010 |
| WO | 2011/011712 A1 | 1/2011 |
| WO | 2011/019780 A1 | 2/2011 |
| WO | 2011/043568 A2 | 4/2011 |

OTHER PUBLICATIONS

Namal C. Warshakoon et al., "Design and synthesis of a series of novel pyrazolopyridines as HIF 1-α prolyl hydroxylase inhibitors", Bioorganic & Medicinal Chemistry Letters, 2006, pp. 5687-5690, vol. 16.

International Search Report for PCT/JP2014/059912 dated Jun. 17, 2014.

* cited by examiner

PYRAZOLE DERIVATIVE

CROSS REFERENCE TO RELATED APPLICATIONS

This application is a National Stage of International Application No. PCT/JP2014/059912 filed Mar. 28, 2014, claiming priority based on Japanese Patent Application No. 2013-072788 filed Mar. 29, 2013, the contents of all of which are incorporated herein by reference in their entirety.

TECHNICAL FIELD

The present invention relates to a novel compound having a xanthine oxidase inhibitory activity and a method for manufacturing the same as well as a xanthine oxidase inhibitor containing the compound as an active ingredient.

In particular, the present invention relates to a pyrazole derivative useful as a therapeutic agent or a preventive agent for diseases associated with xanthine oxidase such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary disease, inflammatory bowel diseases or autoimmune diseases.

BACKGROUND ART

Xanthine oxidase is an enzyme catalyzing the conversion of hypoxanthine to xanthine and further to uric acid in nucleic acid metabolism.

A xanthine oxidase inhibitor inhibits uric acid synthesis to reduce a level of uric acid in the blood with respect to the action of xanthine oxidase. That is, a xanthine oxidase inhibitor is effective as a therapeutic agent for hyperuricemia and various diseases caused by hyperuricemia. On the other hand, there are gouty arthritis and gouty tophus called gout as a clinical condition caused as a result of deposition of urate crystals after prolonged hyperuricemia. In addition, hyperuricemia is considered to be important as a factor of lifestyle diseases associated with obesity, hypertension, dyslipidemia and diabetes or metabolic syndromes, and recently, it has been clarified that hyperuricemia is a risk factor of renal damage, urinary calculi and cardiovascular diseases according to epidemiological surveys (Guideline for the Management of Hyperuricemia and Gout, 2nd edition). Further, a xanthine oxidase inhibitor is expected to be useful for the treatment of diseases associated with active oxygen species by the active oxygen species generation inhibitory activity, for example, for the treatment of cardiovascular diseases through the vascular function-improving action (Circulation. 2006; 114: 2508-2516).

Allopurinol and febuxostat are clinically used as a therapeutic agent for hyperuricemia, but allopurinol has been reported to have a side effect such as Stevens-Johnson syndrome, toxic epidermal necrolysis, hepatic disorder and renal dysfunction (Nippon Rinsho, 2003; 61, Suppl. 1: 197-201).

As a compound having a xanthine oxidase inhibitory activity, for example, there have been reported a phenyl pyrazole derivative (Patent Documents 1 to 3), and a triaryl carboxylic acid derivative (Patent Documents 4 to 7), and the like, such as a pyrazole derivative in which the central aromatic ring is a benzene ring. In addition, there has been reported a pyrazole derivative which is a central bicyclic hetero ring such as a 6-indolepyrazole derivative (Patent Documents 8).

On the other hand, in Non-Patent Documents 1 and 2, a pyrazole carboxylic acid derivative having a pyridine ring in the center is reported.

CITATION LIST

Patent Literature

PTL 1: Japanese Unexamined Patent Application Publication S59-95272
PTL 2: International Publication No. 98/18765
PTL 3: Japanese Unexamined Patent Application Publication H10-310578
PTL 4: International Publication No. 2007/043457
PTL 5: International Publication No. 2007/097403
PTL 6: International Publication No. 2008/126770
PTL 7: International Publication No. 2008/126772
PTL 8: International Publication No. 2011/043568

Non-Patent Literature

NPL 1: Bioorganic Medicinal Chemistry Letters, 2006, Vol. 16(21), p. 5616-5620
NPL 2: Bioorganic Medicinal Chemistry Letters, 2006, Vol. 16(21), p. 5687-5690

SUMMARY OF INVENTION

Technical Problem

An object of the present invention is to provide a novel compound having a xanthine oxidase inhibitory activity. Further, an object of the present invention is to provide a compound having an excellent uric acid lowering action. In addition, an object of the present invention is to provide a compound useful as a therapeutic agent or a preventive agent for diseases associated with xanthine oxidase such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary disease, inflammatory bowel diseases or autoimmune diseases.

Solution to Problem

As a result of earnest studies on compounds having xanthine oxidase inhibitory activity, the inventors have completed the present invention based on the findings: that a compound represented by the following formula (I)

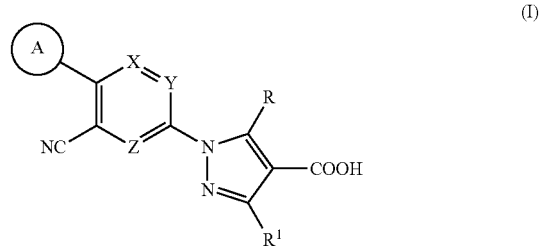

i.e., a pyrazole derivative which has a tricyclic triaryl structure and has as the central ring a pyridine ring possessing one nitrogen atom and substituted with a cyano group, has xanthine oxidase inhibitory activity; further that it has novel xanthine oxidase inhibitory activity accompanied by an excellent uric acid lowering effects; and further that it has sustained xanthine oxidase inhibitory activity that enables particularly excellent uric acid lowering effect over a long period of time. In addition, the inventors have completed the present invention based on the finding that the pyrazole derivative can be a good therapeutic or prophylactic agent for gout, hyperuricemia, tumor lysis syndrome, urinary calculus, hypertension, dyslipidemia, diabetes, cardiovascular diseases such as arteriosclerosis or heart failure, renal diseases such as diabetic nephropathy, respiratory diseases such as chronic obstructive pulmonary disease, inflammatory bowel diseases, autoimmune diseases, or the like.

The present invention is a compound represented by the following formula (I):

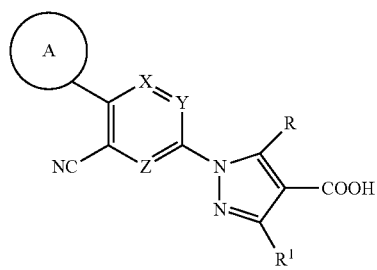

(I)

wherein:

A represents a $C_{6-10}$ aryl group or a heteroaryl group, wherein the aryl group or heteroaryl group may be unsubstituted or substituted with 1 to 3 groups Q which are the same or different from one another and selected from the group consisting of a halogen atom, —CN, —NO$_2$, a $C_{1-6}$ alkyl group, a $C_{3-7}$ cycloalkyl group, a $C_{1-6}$ halogenoalkyl group, a phenyl group, —CH$_2$—O—R$^2$, —O—R$^2$, —O—C$_{1-6}$ halogenoalkyl, —O-benzyl, —O-phenyl, —O—CO—R$^2$, —NR$^3$R$^4$, —NH—CO—R$^2$, —CO$_2$—R$^2$, —CO—R$^2$, —CO—NR$^3$R$^4$, —NH—SO$_2$—R$^2$, —CO-aryl, —S—R$^2$, —SO$_2$—C$_{1-6}$ alkyl, and —SO$_2$-phenyl;

X, Y, and Z represent CR$^5$ or a nitrogen atom, wherein one of X, Y, and Z represents a nitrogen atom and the remaining two represent CR$^5$;

R represents a hydrogen atom or a $C_{1-6}$ alkyl group;

R$^1$ represents a hydrogen atom, an amino group, or a $C_{1-6}$ alkyl group;

R$^2$ represents a hydrogen atom or a $C_{1-6}$ alkyl group;

R$^3$ and R$^4$ are the same or different from each other and are a hydrogen atom or a $C_{1-6}$ alkyl group, where R$^3$ and R$^4$ may be taken together to form with the nitrogen atom to which they are attached a nitrogen-containing saturated monocyclic heterocycle; and R$^5$ represents a hydrogen atom, a halogen atom, or a $C_{1-6}$ alkyl group;

or a pharmaceutically acceptable salt thereof.

The present invention is also a pharmaceutical composition comprising a compound represented by the above formula (I), or a pharmaceutically acceptable salt thereof, and a pharmaceutically acceptable carrier.

The present invention is also a xanthine oxidase inhibitor comprising a compound represented by the above formula (I), or a pharmaceutically acceptable salt thereof, as an active ingredient.

The present invention is also a therapeutic or prophylactic agent for diseases associated with xanthine oxidase, such as gout, hyperuricemia, tumor lysis syndrome, urinary calculus, hypertension, dyslipidemia, diabetes, cardiovascular diseases such as arteriosclerosis or heart failure, renal diseases such as diabetic nephropathy, respiratory diseases such as chronic obstructive pulmonary disease, inflammatory bowel diseases, or autoimmune diseases, comprising a compound represented by the above formula (I), or a pharmaceutically acceptable salt thereof, as an active ingredient.

Furthermore, the present invention is a compound represented by the following formula (II) which can be used as an intermediate in the manufacture of the compound represented by the above formula (I):

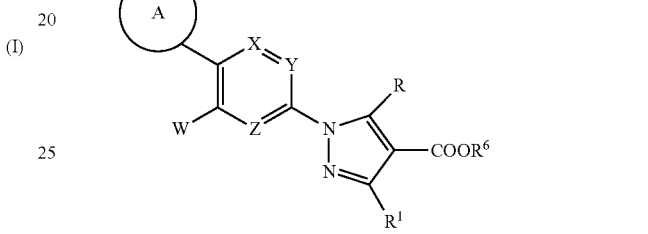

(II)

wherein:

A represents a $C_{6-10}$ aryl group or a heteroaryl group, wherein the aryl group or heteroaryl group may be unsubstituted or substituted with 1 to 3 groups Q which are the same or different from one another and selected from the group consisting of a halogen atom, —CN, —NO$_2$, a $C_{1-6}$ alkyl group, a $C_{3-7}$ cycloalkyl group, a $C_{1-6}$ halogenoalkyl group, a phenyl group, —CH$_2$—O—R$^2$, —O—R$^2$, —O—C$_{1-6}$ halogenoalkyl, —O-benzyl, —O-phenyl, —O—CO—R$^2$, —NR$^3$R$^4$, —NH—CO—R$^2$, —CO$_2$—R$^2$, —CO—R$^2$, —CO—NR$^3$R$^4$, —NH—SO$_2$—R$^2$, —CO-aryl, —S—R$^2$, —SO$_2$—C$_{1-6}$ alkyl, and —SO$_2$-phenyl;

X, Y, and Z represent CR$^5$ or a nitrogen atom, wherein one of X, Y, and Z represents a nitrogen atom and the remaining two represent CR$^5$;

R represents a hydrogen atom or a $C_{1-6}$ alkyl group;

R$^1$ represents a hydrogen atom, an amino group, or a $C_{1-6}$ alkyl group;

R$^2$ represents a hydrogen atom or a $C_{1-6}$ alkyl group;

R$^3$ and R$^4$ are the same or different from each other and are a hydrogen atom or a $C_{1-6}$ alkyl group, where R$^3$ and R$^4$ may be taken together to form with the nitrogen atom to which they are attached a nitrogen-containing saturated monocyclic heterocycle; and R$^5$ represents a hydrogen atom, a halogen atom, or a $C_{1-6}$ alkyl group;

R$^6$ represents a protective group of a carboxyl group; and

W represents a halogen atom, a methanesulfonyloxy group, a p-toluenesulfonyloxy group, a trifluoromethanesulfonyloxy group, or a cyano group.

Furthermore, the present invention is a compound represented by the following formula (III) which can be used as an intermediate in the manufacture of the compound represented by the above formula (I):

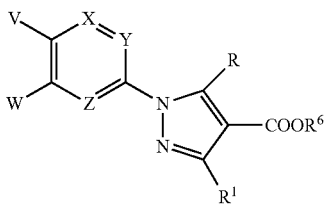

(III)

Wherein,

X, Y, and Z represent $CR^5$ or a nitrogen atom, wherein one of X, Y, and Z represents a nitrogen atom and the remaining two represent $CR^5$;

R represents a hydrogen atom or a $C_{1-6}$ alkyl group;

$R^1$ represents a hydrogen atom, an amino group, or a $C_{1-6}$ alkyl group;

$R^5$ represents a hydrogen atom, a halogen atom, or a $C_{1-6}$ alkyl group;

$R^6$ represents a protective group of a carboxyl group;

V represents a halogen atom, a methanesulfonyloxy group, a p-toluenesulfonyloxy group, a trifluoromethanesulfonyloxy group, a hydroxyl group, or a benzyloxy group; and W represents a halogen atom, a methanesulfonyloxy group, a p-toluenesulfonyloxy group, a trifluoromethanesulfonyloxy group, or a cyano group.

Furthermore, the present invention is a compound represented by the following formula (IV) which can be used as an intermediate in the manufacture of the compound represented by the above formula (I):

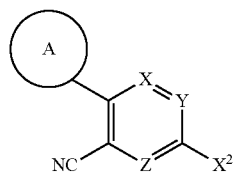

(IV)

wherein:

A represents a $C_{6-10}$ aryl group or a heteroaryl group, wherein the aryl group or heteroaryl group may be unsubstituted or substituted with 1 to 3 groups Q which are the same or different from one another and selected from the group consisting of a halogen atom, —CN, —$NO_2$, a $C_{1-6}$ alkyl group, a $C_{3-7}$ cycloalkyl group, a $C_{1-6}$ halogenoalkyl group, a phenyl group, —$CH_2$—O—$R^2$, —O—$R^2$, —O—$C_{1-6}$ halogenoalkyl, —O-benzyl, —O-phenyl, —O—CO—$R^2$, —$NR^3R^4$, —NH—CO—$R^2$, —$CO_2$—$R^2$, —CO—$R^2$, —CO—$NR^3R^4$, —NH—$SO_2$—$R^2$, —CO-aryl, —S—$R^2$, —$SO_2$—$C_{1-6}$ alkyl, and —$SO_2$-phenyl;

X, Y, and Z represent $CR^5$ or a nitrogen atom, wherein one of X, Y, and Z represents a nitrogen atom and the remaining two represent $CR^5$;

$R^2$ represents a hydrogen atom or a $C_{1-6}$ alkyl group;

$R^3$ and $R^4$ are the same or different from each other and are a hydrogen atom or a $C_{1-6}$ alkyl group, where $R^3$ and $R^4$ may be taken together to form with the nitrogen atom to which they are attached a nitrogen-containing saturated monocyclic heterocycle; and $R^5$ represents a hydrogen atom, a halogen atom, or a $C_{1-6}$ alkyl group; and $X^2$ represents a halogen atom, a methanesulfonyloxy group, a p-toluenesulfonyloxy group or a trifluoromethanesulfonyloxy group.

Advantageous Effects of Invention

The present invention provides a novel compound having a high inhibitory activity of xanthine oxidase and a method for manufacturing the same compound. Further, the compound by the present invention is useful as a therapeutic agent or a preventive agent for diseases associated with xanthine oxidase in particular such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary disease, inflammatory bowel diseases or autoimmune diseases.

DESCRIPTION OF EMBODIMENTS

Terms used alone or in combination in the present specification will be explained below. Unless otherwise stated, the explanation of each substituent shall be common to each site. It should be noted that when any variable occurs in any number of constituents, its definition is independent in each constituent. In addition, combinations of substituents and variables are permissible only if such combinations result in chemically stable compounds.

"Xanthine oxidase" is used both in a broad sense that it is an enzyme for catalyzing an oxidation reaction from hypoxanthine to xanthine and further to uric acid and in a narrow sense that it is an oxidase type xanthine oxidoreductase which is one of the enzymes that catalyze the same reaction. In the present invention, unless otherwise specified, "xanthine oxidase" is collectively called an enzyme which catalyzes an oxidation reaction from hypoxanthine to xanthine and further to uric acid. Among the xanthine oxidoreductase which is responsible for this reaction, two types of oxidase type oxidoreductase and dehydrogenase type oxidoreductase are present and both types are included in the xanthine oxidase of the present invention. Unless otherwise specified, "xanthine oxidase" in "xanthine oxidase inhibitory activity", "xanthine oxidase inhibitor" and the like also has the same meaning as defined above.

For the purpose of the present invention, an "aryl group" means a group formed by removing one of the hydrogen atoms bonded to an aromatic hydrocarbon ring. $C_{6-10}$ aryl groups include, for example, phenyl, naphthyl, indenyl, tetrahydronaphthyl, indanyl, azulenyl groups, and the like.

For the purpose of the present invention, a "heteroaryl group" means a 3- to 10-membered monocyclic or bicyclic heterocyclic ring system of aromatic character which contains 1 to 5 heteroatoms selected from the group consisting of oxygen, sulfur, and nitrogen atoms. The "3- to 10-membered monocyclic or bicyclic heterocyclic ring system of aromatic character" refers to a monovalent group derived by the removal of a hydrogen atom from a 3- to 10-membered monocyclic or bicyclic aromatic heterocycle and having 1 to 5 heteroatoms selected from the group consisting of oxygen, sulfur, and nitrogen atoms. In the case of a bicyclic heteroaryl group, if one of the rings is an aromatic ring or an aromatic heterocycle, the other ring may have a ring structure which is not aromatic. The numbers of the respective heteroatoms and their combination in such a heteroaryl group are not particularly limited as long as they can form part of a ring of a predetermined number of members and exist chemically stably. Such heteroaryl groups include, for example, pyridyl, pyrazyl, pyrimidyl, pyridazinyl, furyl, thienyl, pyrazolyl, 1,3-dioxaindanyl, isoxazolyl, isothiazolyl, benzofuranyl, isobenzofuryl, benzothienyl, indolyl, isoindolyl, chromanyl, benzothiazolyl, benzimidazolyl, benzoxazolyl, pyranyl, imidazolyl, oxazolyl, thiazolyl, triazinyl, triazolyl, furazanyl, thiadiazolyl, dihydrobenzofuryl, dihydroisobenzofuryl, dihydroquinolyl, dihydroisoquinolyl, dihydrobenzoxazolyl, dihydropteridinyl, benzoxazolyl, benzisoxazolyl, benzodioxazolyl, quinolyl, isoquinolyl, benzotriazolyl, pteridinyl, purinyl, quinoxalinyl, quinazolinyl, cinnolinyl, tetrazolyl groups, and the like.

For the purpose of the present invention, a "halogen atom" means a fluorine, chlorine, bromine, or iodine atom.

For the purpose of the present invention, an "alkyl group" means a monovalent saturated linear or branched aliphatic hydrocarbon group. $C_{1-6}$ alkyl groups include, for example, methyl, ethyl, n-propyl, n-butyl, n-pentyl, n-hexyl, isopropyl, isobutyl, s-butyl, t-butyl, isopentyl, 2-methylbutyl, neopentyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, t-pentyl, isohexyl groups, and the like.

For the purpose of the present invention, an "alkylene group" means a divalent saturated linear or branched aliphatic hydrocarbon group having 1 to 6 carbon atoms. $C_{1-6}$ alkylene groups include, for example, methylene, ethylene, n-propylene, isopropylene, n-pentylene, n-hexylene groups, and the like.

For the purpose of the present invention, a "cycloalkyl group" means a cyclic saturated hydrocarbon group. $C_{3-7}$ cycloalkyl groups include, for example, cyclopropyl, cyclobutyl, cyclopentyl, cyclohexyl, cycloheptyl groups, and the like.

For the purpose of the present invention, a "halogenoalkyl group" means an alkyl group substituted with one or more halogens. $C_{1-6}$ halogenoalkyl groups include, for example, trifluoromethyl, difluoromethyl groups, and the like.

For the purpose of the present invention, a "nitrogen-containing saturated monocyclic heterocycle" means a 5- to 8-membered saturated or partially unsaturated monocyclic heterocycle which contains one nitrogen atom and may further contain one heteroatom selected from the group consisting of nitrogen, sulfur, and oxygen atoms, and includes, for example, pyrrolidine, piperidine, piperazine, azepane, diazepane, azocane, morpholine, thiomorpholine, tetrahydropyridine rings, and the like.

In the foregoing "nitrogen-containing saturated monocyclic heterocycle," a sulfur atom, which is a ring atom, may be oxidized to form an oxide or a dioxide, or a nitrogen atom may be oxidized to form an oxide.

In the present invention, a "protective group of a carboxyl group" is, for example, a general protective group of a carboxyl group, which is described in PROTECTIVE GROUPS IN ORGANIC SYNTHESIS, THIRD EDITION, John Wiley & Sons. Inc. Examples of the protective group include methyl group, ethyl group, isopropyl group, heptyl group, t-butyl group, methoxymethyl group, methylthiomethyl group, methoxyethoxymethyl group, methoxyethyl group, benzyl group, t-butyldimethylsilyl groups, and the like.

In the foregoing formula (I), A represents a $C_{6-10}$ aryl group or a heteroaryl group, wherein the aryl group or heteroaryl group may be unsubstituted or substituted with 1 to 3 groups Q which are the same or different from one another and selected from the group consisting of a halogen atom, —CN, —NO$_2$, a $C_{1-6}$ alkyl group, a $C_{3-7}$ cycloalkyl group, a $C_{1-6}$ halogenoalkyl group, a phenyl group, —CH$_2$—O—R$^2$, —O—R$^2$, —O—C$_{1-6}$ halogenoalkyl, —O-benzyl, —O-phenyl, —O—CO—R$^2$, —NR$^3$R$^4$, —NH—CO—R$^2$, —CO$_2$—R$^2$, —CO—R$^2$, —CO—NR$^3$R$^4$, —NH—SO$_2$—R$^2$, —CO-aryl, —S—R$^2$, —SO$_2$—C$_{1-6}$ alkyl, and —SO$_2$-phenyl;

Although specific examples of the "aryl group" and the "heteroaryl group" are as defined above, preferred "aryl groups" or "heteroaryl groups" for A include phenyl, pyridyl, pyrazyl, pyrimidyl, furyl, thienyl, isoxazolyl, isothiazolyl, benzofuranyl, benzothienyl, benzothiazolyl, benzimidazolyl, benzoxazolyl, pyranyl, imidazolyl, oxazolyl, thiazolyl, triazinyl, triazolyl, benzoxazolyl, benzisoxazolyl groups, and the like, and more preferred are phenyl and thienyl groups.

A may be unsubstituted or substituted with 1 to 3 groups Q which are the same or different from one another and selected from the group consisting of a halogen atom, —CN, —NO$_2$, a $C_{1-6}$ alkyl group, a $C_{3-7}$ cycloalkyl group, a $C_{1-6}$ halogenoalkyl group, a phenyl group, —CH$_2$—O—R$^2$, —O—R$^2$, —O—C$_{1-6}$ halogenoalkyl, —O-benzyl, —O-phenyl, —O—CO—R$^2$, —NR$^3$R$^4$, —NH—CO—R$^2$, —CO$_2$—R$^2$, —CO—R$^2$, —CO—NR$^3$R$^4$, —NH—SO$_2$—R$^2$, —CO-aryl, —S—R$^2$, —SO$_2$—C$_{1-6}$ alkyl, and —SO$_2$-phenyl. In the case where A is substituted with Q, the number of Q is preferably 1 or 2. It is preferred that A is unsubstituted or substituted with group(s) Q selected from the group consisting of a halogen atom, a $C_{1-6}$ alkyl group, a $C_{3-7}$ cycloalkyl group, a $C_{1-6}$ halogenoalkyl group, a phenyl group, —O—R$^2$, and —O—C$_{1-6}$ halogenoalkyl. It is more preferred that A is unsubstituted or substituted with group(s) Q selected from the group consisting of a halogen atom, a methyl group, and a methoxy group. As the halogen atom, a fluorine atom is preferred.

Particularly preferred A can be represented, for example, by the following structural formulae.

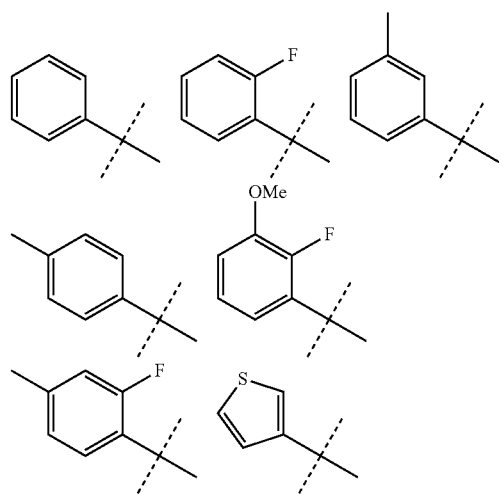

In the foregoing formula (I), R represents a hydrogen atom or a $C_{1-6}$ alkyl group. Although specific examples of the "$C_{1-6}$ alkyl group" are as defined above, preferred "$C_{1-6}$ alkyl groups" include methyl, ethyl, n-propyl, n-butyl, n-pentyl, n-hexyl, isopropyl, isobutyl, s-butyl, t-butyl, isopentyl, 2-methylbutyl, neopentyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, t-pentyl, isohexyl groups, and the like. R is more preferably a hydrogen atom or a methyl group, and particularly preferably a hydrogen atom.

In the foregoing formula (I), $R^1$ represents a hydrogen atom, an amino group or a $C_{1-6}$ alkyl group. Although specific examples of the "$C_{1-6}$ alkyl group" are as defined above, preferred "$C_{1-6}$ alkyl groups" include methyl, ethyl, n-propyl, n-butyl, n-pentyl, n-hexyl, isopropyl, isobutyl, s-butyl, t-butyl, isopentyl, 2-methylbutyl, neopentyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, t-pentyl, isohexyl groups, and the like. $R^1$ is more preferably a hydrogen atom, an amino group or a methyl group, and particularly preferably a hydrogen atom.

In the foregoing formula (I), $R^2$ represents a hydrogen atom, an amino group or a $C_{1-6}$ alkyl group. Although specific examples of the "$C_{1-6}$ alkyl group" are as defined above, preferred "$C_{1-6}$ alkyl groups" include methyl, ethyl, n-propyl, n-butyl, n-pentyl, n-hexyl, isopropyl, isobutyl, s-butyl, t-butyl, isopentyl, 2-methylbutyl, neopentyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, t-pentyl, isohexyl groups, and the like. $R^2$ is more preferably a hydrogen atom or a methyl group, and particularly preferably a methyl group.

In the foregoing formula (I), $R^3$ and $R^4$ are the same or different from each other and are a hydrogen atom or a $C_{1-6}$ alkyl group, where $R^3$ and $R^4$ may be taken together to form with the nitrogen atom to which they are attached a nitrogen-containing saturated monocyclic heterocycle. Although specific examples of the "$C_{1-6}$ alkyl group" and the "nitrogen-containing saturated monocyclic heterocycle" are as defined above, preferred "$C_{1-6}$ alkyl groups" include methyl, ethyl, n-propyl, n-butyl, n-pentyl, n-hexyl, isopropyl, isobutyl, s-butyl, t-butyl, isopentyl, 2-methylbutyl, neopentyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, t-pentyl, isohexyl groups, and the like, and preferred "nitrogen-containing saturated monocyclic heterocycles" include pyrrolidine, piperidine, piperazine, azepane, diazepane, azocane, morpholine, thiomorpholine, tetrahydropyridine rings, and the like. More preferred as $R^3$, $R^4$, and "nitrogen-containing saturated monocyclic heterocycles" are a hydrogen atom, a methyl group, pyrrolidine, piperidine, piperazine, and morpholine, and particularly preferred are a hydrogen atom, a methyl group, and morpholine.

In the foregoing formula (I), X, Y, and Z represent $CR^5$ or a nitrogen atom, wherein one of X, Y, and Z represents a nitrogen atom and the remaining two represent $CR^5$. The three cases where each one of X, Y, and Z is a nitrogen atom can be represented by the following structural formulae. Among these, the one where Y is a nitrogen atom is preferred.

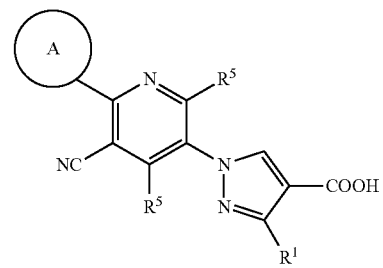

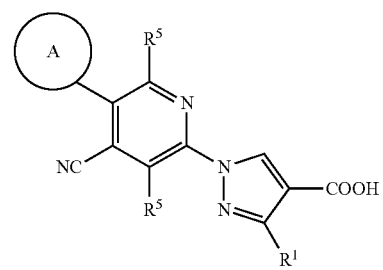

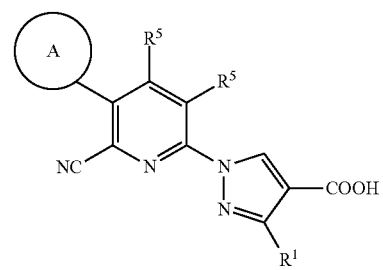

$R^5$ includes a hydrogen atom, a halogen atom, or a $C_{1-6}$ alkyl group, and a hydrogen atom is preferred.

In the foregoing formula (I), as a combination of A, Q, R, $R^1$, $R^2$, $R^3$, $R^4$, $R^5$, X, Y, and Z, a combination of preferred groups, each of which is described above, is preferred, and a combination of groups which are described as more preferred is more preferred. A combination where A and $R^1$ in the structure of formula (I) of the combination of groups which are described as more preferred are replaced by particularly preferred groups is particularly preferred.

The compounds of the present invention are those that exhibit excellent xanthine oxidase inhibitory activity. In addition, the compounds of the present invention have excellent uric acid-lowering effects. Furthermore, the compounds of the present invention have prolonged sustained uric acid-lowering effects.

Specific examples of preferred compounds can include the following compounds.

| Compound No. | Structure | Name |
|---|---|---|
| 1 | 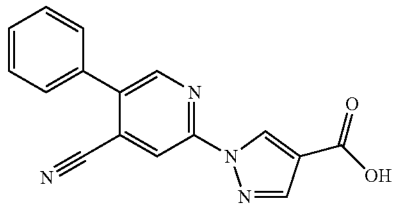 [SMILES: N#Cc1cc(-n2cc(C(=O)O)cn2)ncc1-c1ccccc1] | 1-(4-cyano-5-phenylpyridin-2-yl)-1H-pyrazole-4-carboxylic acid |
| 2 | 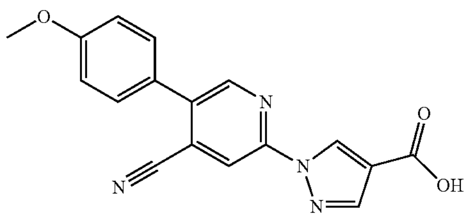 [SMILES: COc1ccc(-c2cnc(-n3cc(C(=O)O)cn3)cc2C#N)cc1] | 1-[4-cyano-5-(4-methoxyphenyl)pyridin-2-yl]-1H-pyrazole-4-carboxylic acid |
| 3 | 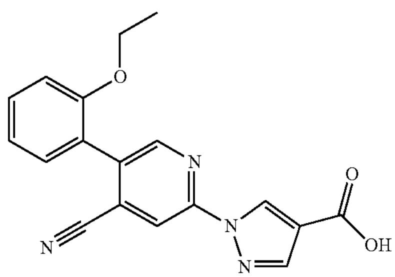 [SMILES: CCOc1ccccc1-c1cnc(-n2cc(C(=O)O)cn2)cc1C#N] | 1-[4-cyano-5-(2-ethoxyphenyl)pyridin-2-yl]-1H-pyrazole-4-carboxylic acid |
| 4 | 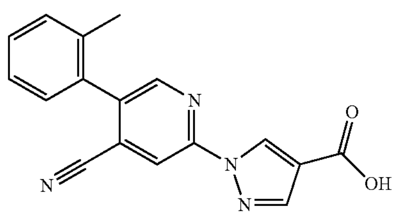 [SMILES: Cc1ccccc1-c1cnc(-n2cc(C(=O)O)cn2)cc1C#N] | 1-[4-cyano-5-(2-methylphenyl)pyridin-2-yl]-1H-pyrazole-4-carboxylic acid |
| 5 | 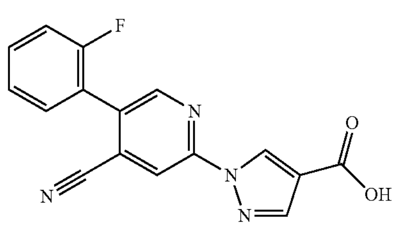 [SMILES: N#Cc1cc(-n2cc(C(=O)O)cn2)ncc1-c1ccccc1F] | 1-[4-cyano-5-(2-fluorophenyl)pyridin-2-yl]-1H-pyrazole-4-carboxylic acid |
| 6 | 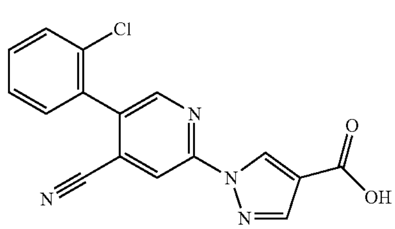 | 1-[4-cyano-5-(2-chlorophenyl)pyridin-2-yl]-1H-pyrazole-4-carboxylic acid |

-continued

| Compound No. | Structure | Name |
|---|---|---|
| 7 | 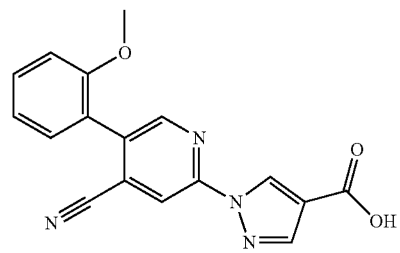 [SMILES: COc1ccccc1-c1cnc(-n2cc(C(=O)O)cn2)cc1C#N] | 1-[4-cyano-5-(2-methoxyphenyl)pyridin-2-yl]-1H-pyrazole-4-carboxylic |
| 8 | 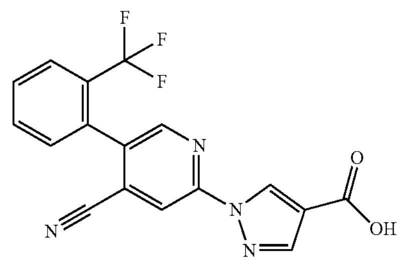 [SMILES: N#Cc1cc(-n2cc(C(=O)O)cn2)ncc1-c1ccccc1C(F)(F)F] | 1-{4-cyano-5-[2-(trifluoromethyl)phenyl]pyridin-2-yl}-1H-pyrazole-4-carboxylic acid |
| 9 | 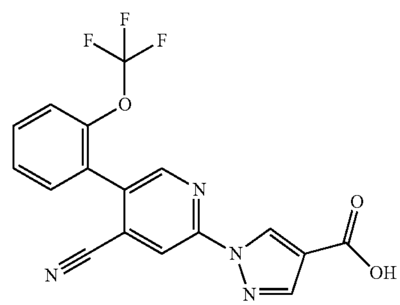 [SMILES: N#Cc1cc(-n2cc(C(=O)O)cn2)ncc1-c1ccccc1OC(F)(F)F] | 1-{4-cyano-5-[2-(trifluoromethoxy)phenyl]pyridin-2-yl]-1H-pyrazole-4-carboxylic acid |
| 10 | 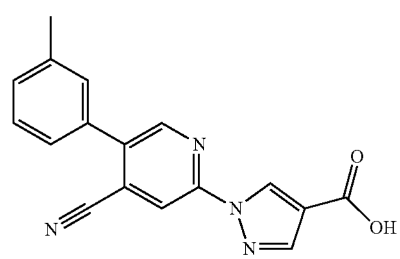 [SMILES: Cc1cccc(-c2cnc(-n3cc(C(=O)O)cn3)cc2C#N)c1] | 1-[4-cyano-5-(3-methylphenyl)pyridin-2-yl]-1H-pyrazole-4-carboxylic acid |
| 11 | 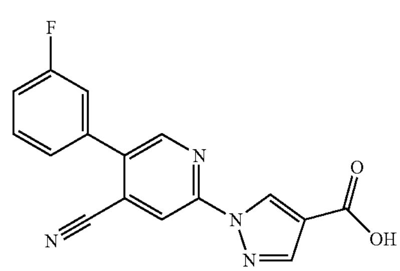 [SMILES: N#Cc1cc(-n2cc(C(=O)O)cn2)ncc1-c1cccc(F)c1] | 1-[4-cyano-5-(3-fluorophenyl)pyridin-2-yl]-1H-pyrazole-4-carboxylic acid |

-continued

| Compound No. | Structure | Name |
|---|---|---|
| 12 | 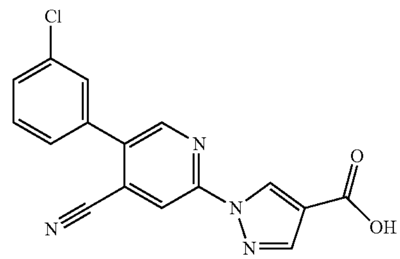 [SMILES: N#Cc1cc(-n2cc(C(=O)O)cn2)ncc1-c1cccc(Cl)c1] | 1-[4-cyano-5-(3-chlorophenyl)pyridin-2-yl]-1H-pyrazole-4-carboxylic acid |
| 13 | 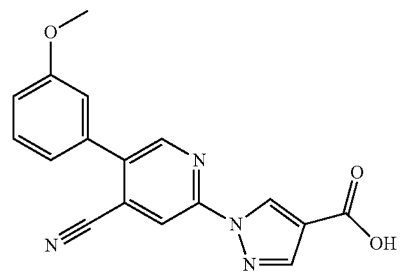 [SMILES: COc1cccc(-c2cnc(-n3cc(C(=O)O)cn3)cc2C#N)c1] | 1-[4-cyano-5-(3-methoxyphenyl)pyridin-2-yl]-1H-pyrazole-4-carboxylic acid |
| 14 | 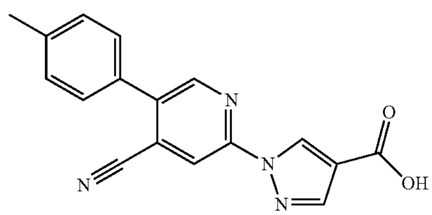 [SMILES: Cc1ccc(-c2cnc(-n3cc(C(=O)O)cn3)cc2C#N)cc1] | 1-[4-cyano-5-(4-methylphenyl)pyridin-2-yl]-1H-pyrazole-4-carboxylic acid |
| 15 | 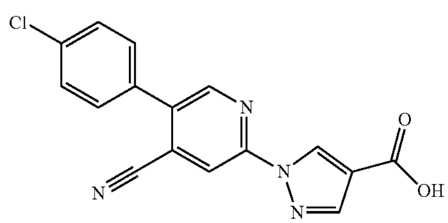 [SMILES: N#Cc1cc(-n2cc(C(=O)O)cn2)ncc1-c1ccc(Cl)cc1] | 1-[4-cyano-5-(4-chlorophenyl)pyridin-2-yl]-1H-pyrazole-4-carboxylic acid |
| 16 | 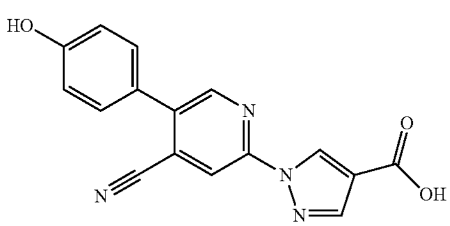 [SMILES: N#Cc1cc(-n2cc(C(=O)O)cn2)ncc1-c1ccc(O)cc1] | 1-[4-cyano-5-(4-hydroxyphenyl)pyridin-2-yl]-1H-pyrazole-4-carboxylic acid |
| 17 | 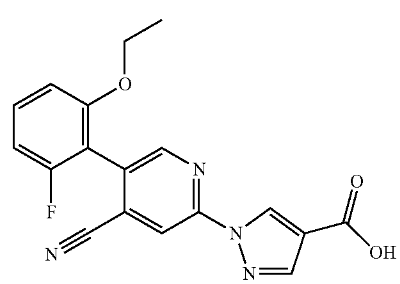 [SMILES: CCOc1cccc(F)c1-c1cnc(-n2cc(C(=O)O)cn2)cc1C#N] | 1-[4-cyano-5-(2-ethoxy-6-fluorophenyl)pyridin-2-yl]-1H-pyrazole-4-carboxylic acid |

-continued

| Compound No. | Structure | Name |
|---|---|---|
| 18 | 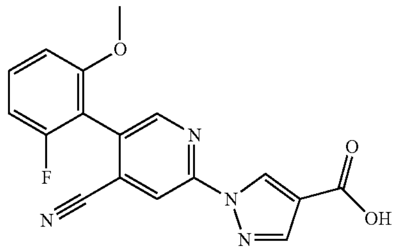 [SMILES: COc1cccc(F)c1-c1cnc(-n2cc(C(=O)O)cn2)cc1C#N] | 1-[4-cyano-5-(2-fluoro-6-methoxyphenyl)pyridin-2-yl]-1H-pyrazole-4-carboxylic acid |
| 19 | 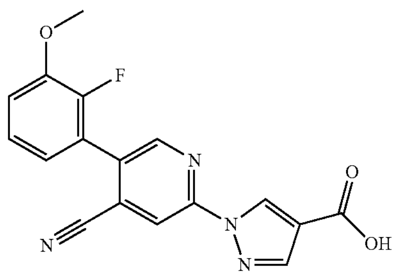 [SMILES: COc1cccc(-c2cnc(-n3cc(C(=O)O)cn3)cc2C#N)c1F] | 1-[4-cyano-5-(2-fluoro-3-methoxyphenyl)pyridin-2-yl]-1H-pyrazole-4-carboxylic acid |
| 20 | 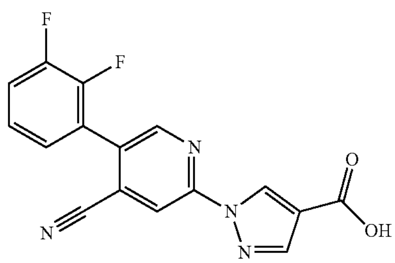 [SMILES: N#Cc1cc(-n2cc(C(=O)O)cn2)ncc1-c1cccc(F)c1F] | 1-[4-cyano-5-(2,3-difluorophenyl)pyridin-2-yl]-1H-pyrazole-4-carboxylic acid |
| 21 | 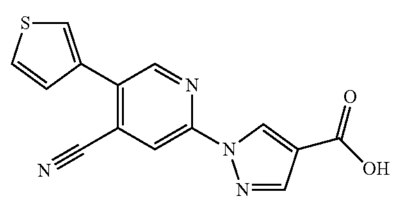 [SMILES: N#Cc1cc(-n2cc(C(=O)O)cn2)ncc1-c1ccsc1] | 1-[4-cyano-5-(thiophen-3-yl)pyridin-2-yl]-1H-pyrazole-4-carboxylic acid |
| 22 | 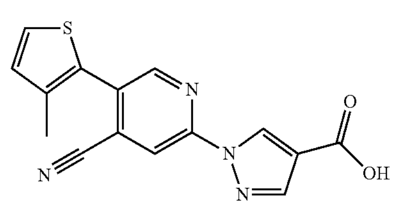 [SMILES: Cc1ccsc1-c1cnc(-n2cc(C(=O)O)cn2)cc1C#N] | 1-[4-cyano-5-(3-methylthiophen-2-yl)pyridin-2-yl]-1H-pyrazole-4-carboxylic acid |
| 23 | 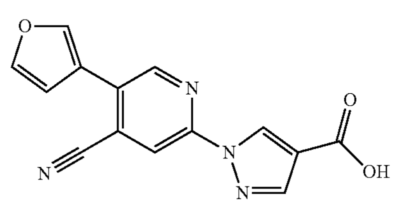 [SMILES: N#Cc1cc(-n2cc(C(=O)O)cn2)ncc1-c1ccoc1] | 1-[4-cyano-5-(furan-3-yl)pyridin-2-yl]-1H-pyrazole-4-carboxylic acid |

-continued

| Compound No. | Structure | Name |
|---|---|---|
| 24 | 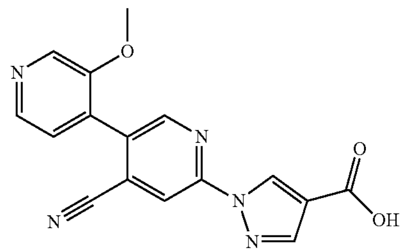 [SMILES: COc1cnccc1-c1cnc(-n2cc(C(=O)O)cn2)cc1C#N] | 1-[4-cyano-5-(3-methoxypyridin-4-yl)pyridin-2-yl]-1H-pyrazole-4-carboxylic acid |
| 25 | 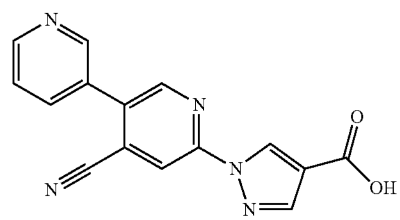 [SMILES: N#Cc1cc(-n2cc(C(=O)O)cn2)ncc1-c1cccnc1] | 1-[4-cyano-5-(pyridin-3-yl)pyridin-2-yl]-1H-pyrazole-4-carboxylic acid |
| 26 | 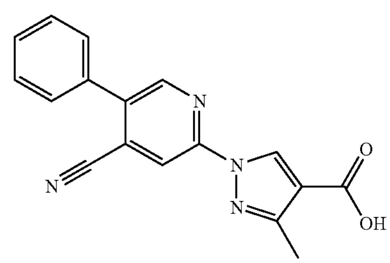 [SMILES: Cc1nn(-c2cc(C#N)c(-c3ccccc3)cn2)cc1C(=O)O] | 1-(4-cyano-5-phenylpyridin-2-yl)-3-methyl-1H-pyrazole-4-carboxylic acid |
| 27 | 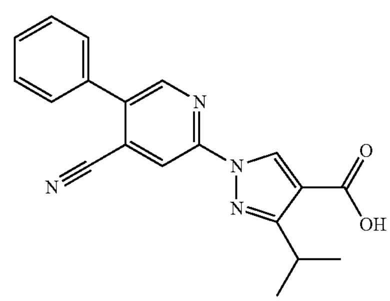 [SMILES: CC(C)c1nn(-c2cc(C#N)c(-c3ccccc3)cn2)cc1C(=O)O] | 1-(4-cyano-5-phenylpyridin-2-yl)-3-(propan-2-yl)-1H-pyrazole-4-carboxylic acid |
| 28 | 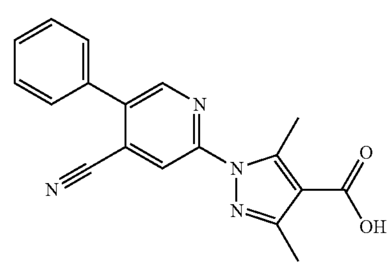 [SMILES: Cc1nn(-c2cc(C#N)c(-c3ccccc3)cn2)c(C)c1C(=O)O] | 1-(4-cyano-5-phenylpyridin-2-yl)-3,5-dimethyl-1H-pyrazole-4-carboxylic acid |
| 29 | 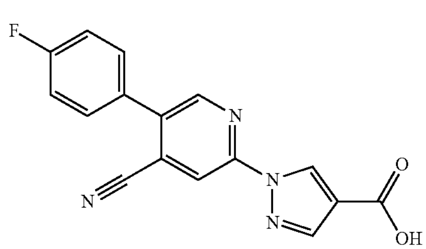 [SMILES: N#Cc1cc(-n2cc(C(=O)O)cn2)ncc1-c1ccc(F)cc1] | 1-[4-cyano-5-(4-fluorophenyl)pyridin-2-yl]-1H-pyrazole-4-carboxylic acid |

-continued
| Compound No. | Structure | Name |
|---|---|---|
| 30 | 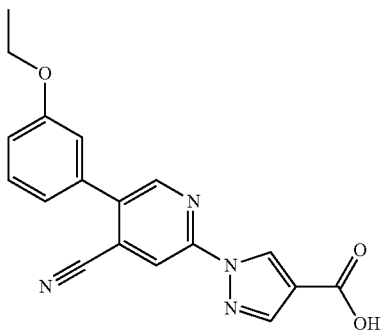 [SMILES: CCOc1cccc(-c2cnc(-n3cc(C(=O)O)cn3)cc2C#N)c1] | 1-[4-cyano-5-(3-ethoxyphenyl)pyridin-2-yl]-1H-pyrazole-4-carboxylic acid |
| 31 | 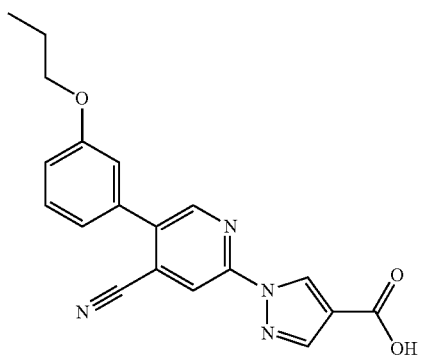 [SMILES: CCCOc1cccc(-c2cnc(-n3cc(C(=O)O)cn3)cc2C#N)c1] | 1-[4-cyano-5-(3-propoxyphenyl)pyridin-2-yl]-1H-pyrazole-4-carboxylic acid |
| 32 | 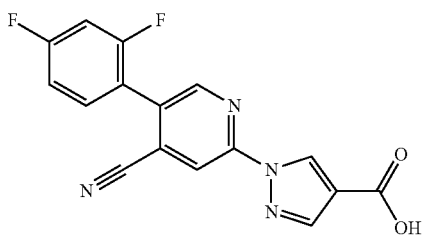 [SMILES: N#Cc1cc(-n2cc(C(=O)O)cn2)ncc1-c1ccc(F)cc1F] | 1-[4-cyano-5-(2,4-difluorophenyl)pyridin-2-yl]-1H-pyrazole-4-carboxylic acid |
| 33 | 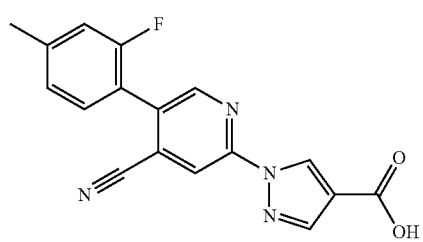 [SMILES: Cc1ccc(-c2cnc(-n3cc(C(=O)O)cn3)cc2C#N)c(F)c1] | 1-[4-cyano-5-(2-fluoro-4-methylphenyl)pyridin-2-yl]-1H-pyrazole-4-carboxylic acid |
| 34 | 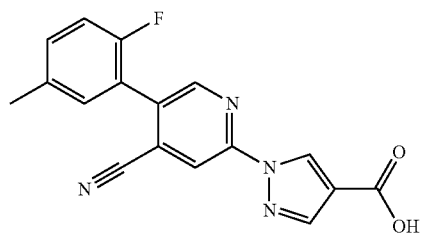 [SMILES: Cc1ccc(F)c(-c2cnc(-n3cc(C(=O)O)cn3)cc2C#N)c1] | 1-[4-cyano-5-(2-fluoro-5-methylphenyl)pyridin-2-yl]-1H-pyrazole-4-carboxylic acid |

-continued

| Compound No. | Structure | Name |
|---|---|---|
| 35 | 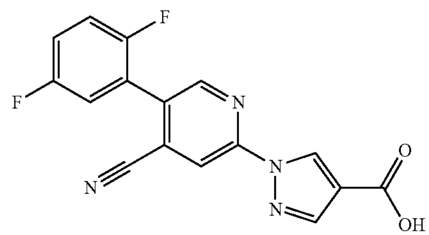 [SMILES: N#Cc1cc(-n2cc(C(=O)O)cn2)ncc1-c1cc(F)ccc1F] | 1-[4-cyano-5-(2,5-difluorophenyl)pyridin-2-yl]-1H-pyrazole-4-carboxylic acid |
| 36 | 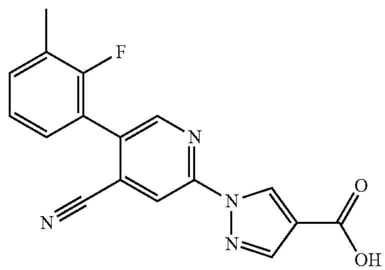 [SMILES: Cc1cccc(-c2cnc(-n3cc(C(=O)O)cn3)cc2C#N)c1F] | 1-[4-cyano-5-(2-fluoro-3-methylphenyl)pyridin-2-yl]-1H-pyrazole-4-carboxylic acid |
| 37 | 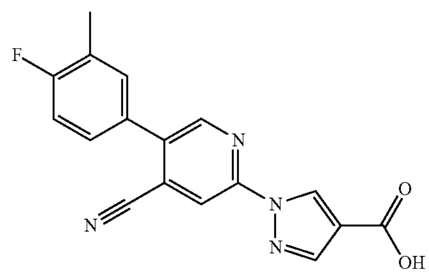 [SMILES: Cc1cc(-c2cnc(-n3cc(C(=O)O)cn3)cc2C#N)ccc1F] | 1-[4-cyano-5-(4-fluoro-3-methylphenyl)pyridin-2-yl]-1H-pyrazole-4-carboxylic acid |
| 38 | 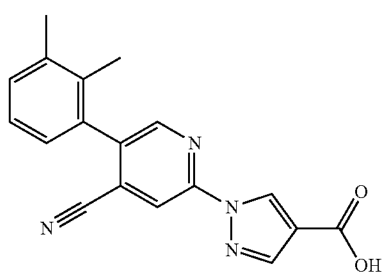 [SMILES: Cc1cccc(-c2cnc(-n3cc(C(=O)O)cn3)cc2C#N)c1C] | 1-[4-cyano-5-(2,3-dimethylphenyl)pyridin-2-yl]-1H-pyrazole-4-carboxylic acid |
| 39 | 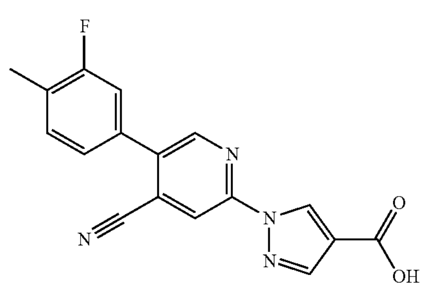 [SMILES: Cc1ccc(-c2cnc(-n3cc(C(=O)O)cn3)cc2C#N)cc1F] | 1-[4-cyano-5-(3-fluoro-4-methylphenyl)pyridin-2-yl]-1H-pyrazole-4-carboxylic acid |

-continued

| Compound No. | Structure | Name |
|---|---|---|
| 40 | 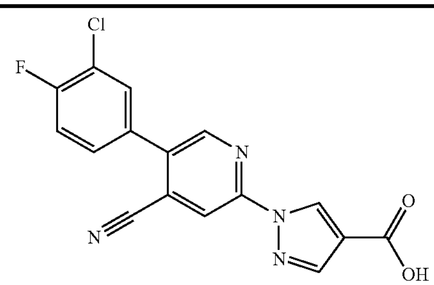 | 1-[4-cyano-5-(3-chloro-4-fluorophenyl)pyridin-2-yl]-1H-pyrazole-4-carboxylic acid |
| 41 | 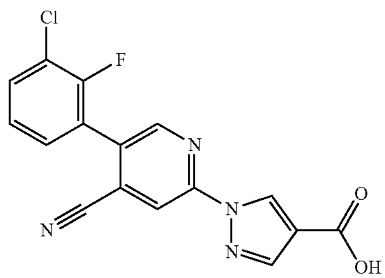 [SMILES: N#Cc1cc(-n2cc(C(=O)O)cn2)ncc1-c1cccc(Cl)c1F] | 1-[4-cyano-5-(3-chloro-2-fluorophenyl)pyridin-2-yl]-1H-pyrazole-4-carboxylic acid |
| 42 | 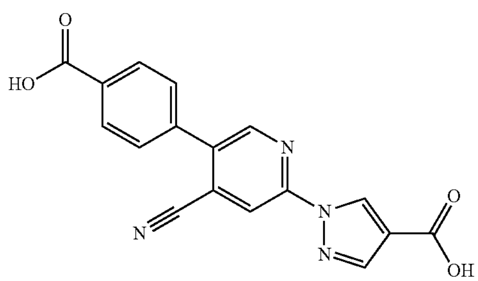 [SMILES: N#Cc1cc(-n2cc(C(=O)O)cn2)ncc1-c1ccc(C(=O)O)cc1] | 1-[5-(4-carboxyphenyl)-4-cyanopyridin-2-yl]-1H-pyrazole-4-carboxylic acid |
| 43 | 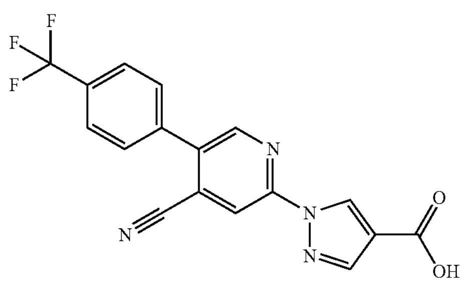 [SMILES: N#Cc1cc(-n2cc(C(=O)O)cn2)ncc1-c1ccc(C(F)(F)F)cc1] | 1-{4-cyano-5-[4-(trifluoromethyl)phenyl]pyridin-2-yl}-1H-pyrazole-4-carboxylic acid |
| 44 | 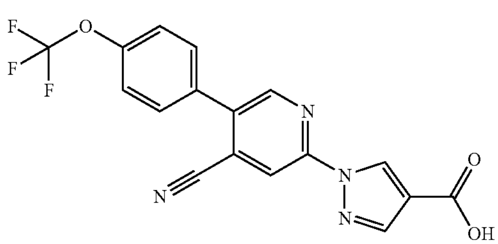 [SMILES: N#Cc1cc(-n2cc(C(=O)O)cn2)ncc1-c1ccc(OC(F)(F)F)cc1] | 1-{4-cyano-5-[4-(trifluoromethoxy)phenyl]pyridin-2-yl}-1H-pyrazole-4-carboxylic acid |
| 45 | 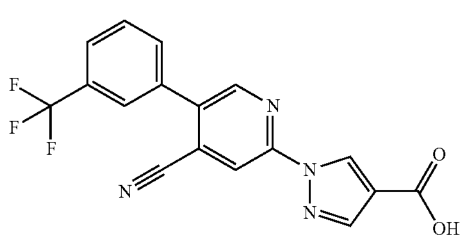 [SMILES: N#Cc1cc(-n2cc(C(=O)O)cn2)ncc1-c1cccc(C(F)(F)F)c1] | 1-{4-cyano-5-[3-(trifluoromethyl)phenyl]pyridin-2-yl}-1H-pyrazole-4-carboxylic acid |

| Compound No. | Structure | Name |
|---|---|---|
| 46 | 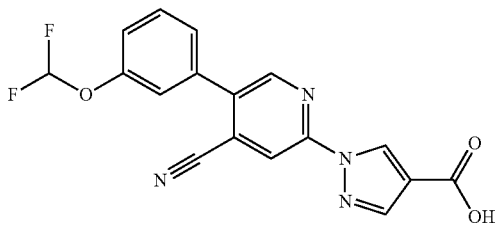 [SMILES: N#Cc1cc(-n2cc(C(=O)O)cn2)ncc1-c1cccc(OC(F)F)c1] | 1-{4-cyano-5-[3-(difluoromethoxy)phenyl]pyridin-2-yl}-1H-pyrazole-4-carboxylic acid |
| 47 | 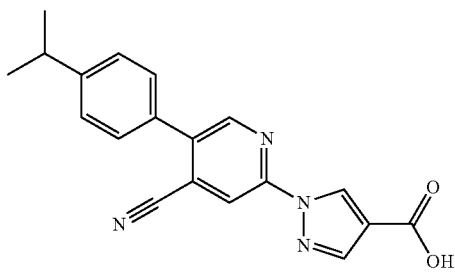 [SMILES: CC(C)c1ccc(-c2cnc(-n3cc(C(=O)O)cn3)cc2C#N)cc1] | 1-[4-cyano-5-[4-(propane-2-yl)phenyl]pyridin-2-yl}-1H-pyrazole-4-carboxylic acid |
| 48 | 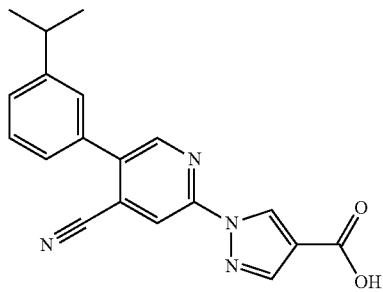 [SMILES: CC(C)c1cccc(-c2cnc(-n3cc(C(=O)O)cn3)cc2C#N)c1] | 1-{4-cyano-5-[3-(propane-2-yl)phenyl]pyridine-2-yl}-1H-pyrazole-4-carboxylic acid |
| 49 | 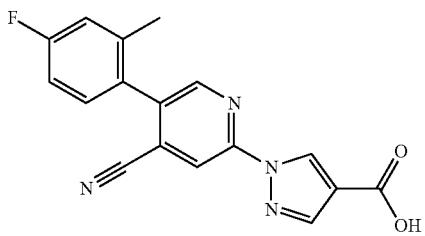 | 1-[4-cyano-5-(4-fluoro-2-methylphenyl)pyridin-2-yl]-1H-pyrazole-4-carboxylic acid |
| 50 | 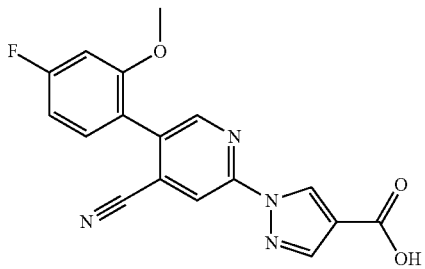 [SMILES: COc1cc(F)ccc1-c1cnc(-n2cc(C(=O)O)cn2)cc1C#N] | 1-[4-cyano-5-(4-fluoro-2-methoxyphenyl)pyridin-2-yl]-1H-pyrazole-4-carboxylic acid |

-continued

| Compound No. | Structure | Name |
|---|---|---|
| 51 | 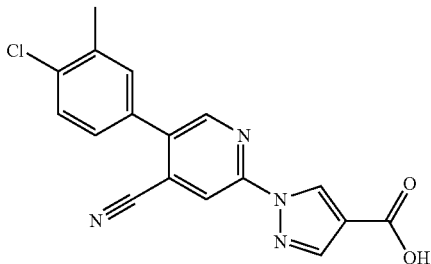 [SMILES: Cc1cc(-c2cnc(-n3cc(C(=O)O)cn3)cc2C#N)ccc1Cl] | 1-[4-cyano-5-(4-chloro-3-methylphenyl)pyridin-2-yl]-1H-pyrazole-4-carboxylic acid |
| 52 | 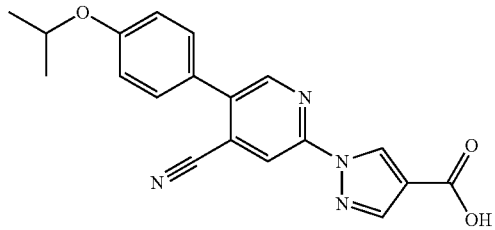 [SMILES: CC(C)Oc1ccc(-c2cnc(-n3cc(C(=O)O)cn3)cc2C#N)cc1] | 1-{4-cyano-5-[4-propan-2-yloxy)phenyl]pyridin-2-yl}-1H-pyrazole-4-carboxylic acid |
| 53 | 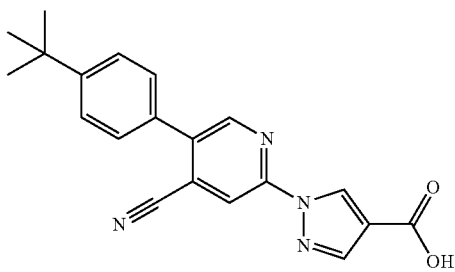 [SMILES: CC(C)(C)c1ccc(-c2cnc(-n3cc(C(=O)O)cn3)cc2C#N)cc1] | 1-[5-(4-tert-butylphenyl)-4-cyanopyridin-2-yl]-1H-pyrazole-4-carboxylic acid |
| 54 | 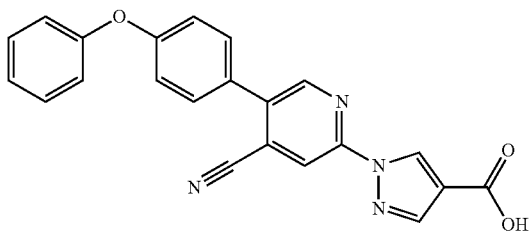 [SMILES: N#Cc1cc(-n2cc(C(=O)O)cn2)ncc1-c1ccc(Oc2ccccc2)cc1] | 1-[4-cyano-5-(4-phenoxyphenyl)pyridin-2-yl]-1H-pyrazole-4-carboxylic acid |
| 55 | 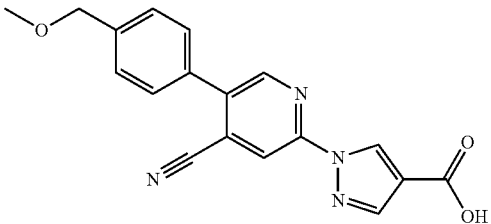 [SMILES: COCc1ccc(-c2cnc(-n3cc(C(=O)O)cn3)cc2C#N)cc1] | 1-{4-cyano-5-[4-(methoxymethyl)phenyl]pyridin-2-yl}-1H-pyrazole-4-carboxylic acid |
| 56 | 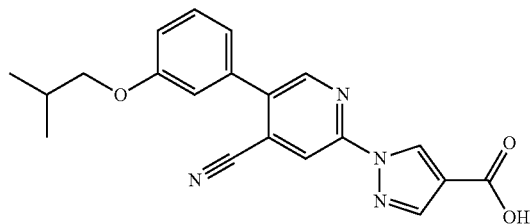 [SMILES: CC(C)COc1cccc(-c2cnc(-n3cc(C(=O)O)cn3)cc2C#N)c1] | 1-{4-cyano-5-[3-(propane-2-yl)phenyl]pyridine-2-yl}-1H-pyrazole-4-carboxylic acid |

| Compound No. | Structure | Name |
|---|---|---|
| 57 | 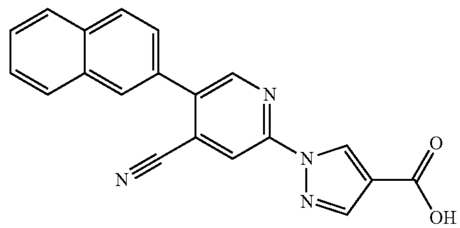 [SMILES: N#Cc1cc(-n2cc(C(=O)O)cn2)ncc1-c1ccc2ccccc2c1] | 1-[4-cyano-5-(naphthalen-2-yl)pyridin-2-yl]-1H-pyrazole-4-carboxylic acid |
| 58 | 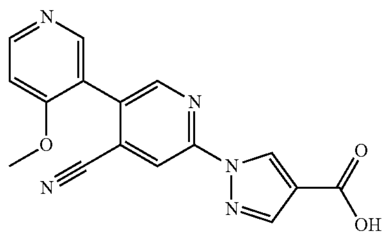 [SMILES: COc1ccncc1-c1cnc(-n2cc(C(=O)O)cn2)cc1C#N] | 1-[4-cyano-5-(4-methoxypyridin-3-yl)pyridin-2-yl]-1H-pyrazole-4-carboxylic acid |
| 59 | 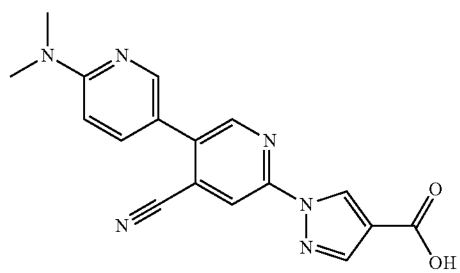 [SMILES: CN(C)c1ccc(-c2cnc(-n3cc(C(=O)O)cn3)cc2C#N)cn1] | 1-{4-cyano-5-[6-(dimethylamino)pyridin-3-yl]pyridin-2-yl}-1H-pyrazole-4-carboxylic acid |
| 60 | 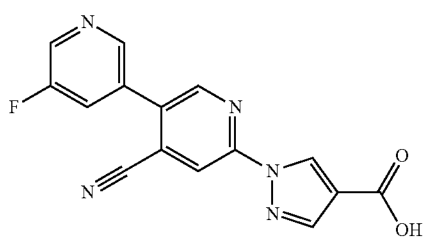 [SMILES: N#Cc1cc(-n2cc(C(=O)O)cn2)ncc1-c1cncc(F)c1] | 1-[4-cyano-5-(5-fluoropyridin-3-yl)pyridin-2-yl]-1H-pyrazole-4-carboxylic acid |
| 61 | 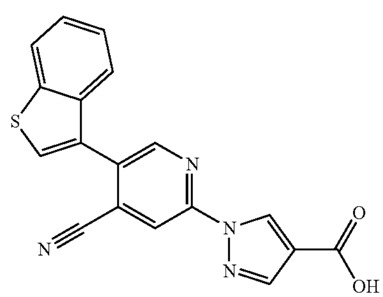 [SMILES: N#Cc1cc(-n2cc(C(=O)O)cn2)ncc1-c1csc2ccccc12] | 1-[5-(1-benzothiophen-3-yl)-4-cyanopyridin-2-yl]-1H-pyrazole-4-carboxylic acid |
| 62 | 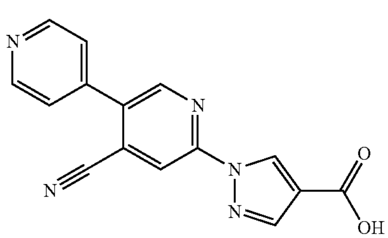 [SMILES: N#Cc1cc(-n2cc(C(=O)O)cn2)ncc1-c1ccncc1] | 1-[4-cyano-5-(pyridin-4-yl)pyridin-2-yl]-1H-pyrazole-4-carboxylic acid |

-continued

| Compound No. | Structure | Name |
|---|---|---|
| 63 | 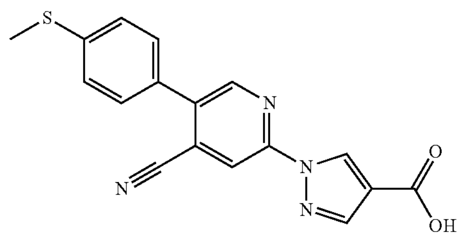 [SMILES: CSc1ccc(-c2cnc(-n3cc(C(=O)O)cn3)cc2C#N)cc1] | 1-{4-cyano-5-[4-(methylsulfanyl)phenyl]pyridin-2-yl}-1H-pyrazole-4-carboxylic acid |
| 64 | 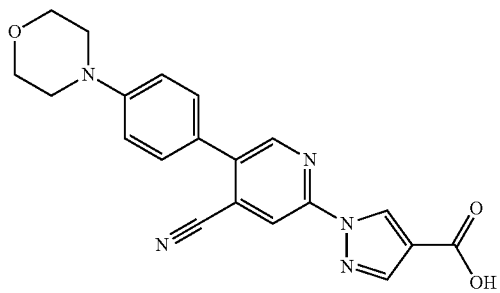 [SMILES: N#Cc1cc(-n2cc(C(=O)O)cn2)ncc1-c1ccc(N2CCOCC2)cc1] | 1-{4-cyano-5-[4-(morpholine-4-yl)phenyl]pyridine-2-yl}-1H-pyrazole-4-carboxylic acid |
| 65 | 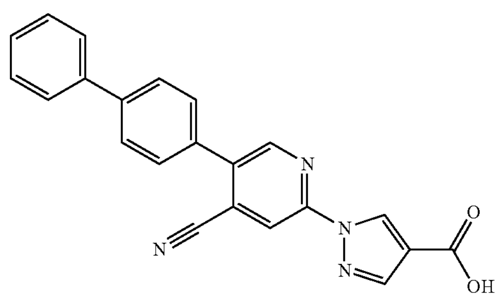 [SMILES: N#Cc1cc(-n2cc(C(=O)O)cn2)ncc1-c1ccc(-c2ccccc2)cc1] | 1-[4-cyano-5-(4-phenylphenyl)pyridine-2-yl]-1H-pyrazole-4-carboxyic acid |
| 66 | 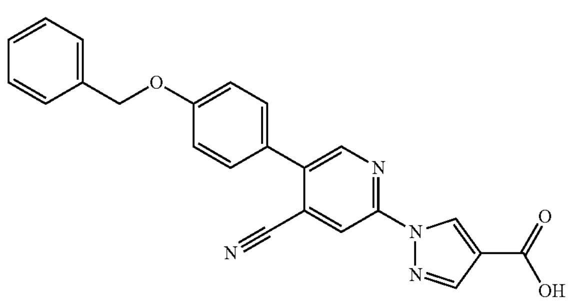 [SMILES: N#Cc1cc(-n2cc(C(=O)O)cn2)ncc1-c1ccc(OCc2ccccc2)cc1] | 1-{5-[4-(benzyloxy)phenyl]-4-cyanopyridine-2-yl}-1H-pyrazole-4-carboxylic acid |
| 67 | 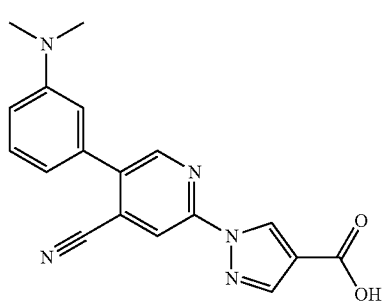 [SMILES: CN(C)c1cccc(-c2cnc(-n3cc(C(=O)O)cn3)cc2C#N)c1] | 1-{4-cyano-5-[3-(dimethylamino)phenyl]pyridine-2-yl}-1H-pyrazole-4-carboxylic acid |

-continued

| Compound No. | Structure | Name |
|---|---|---|
| 68 | 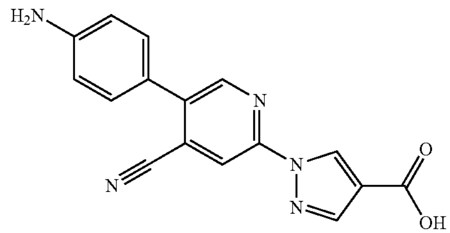 [SMILES: N#Cc1cc(-n2cc(C(=O)O)cn2)ncc1-c1ccc(N)cc1] | 1-[5-(4-aminophenyl)-4-cyanopyridine-2-yl]-1H-pyrazole-4-carboxylic acid |
| 69 | 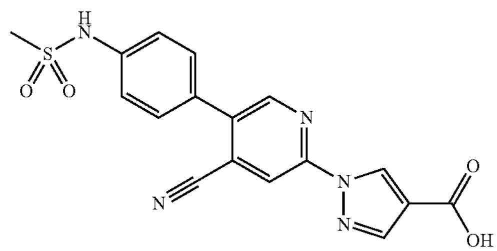 [SMILES: CS(=O)(=O)Nc1ccc(-c2cnc(-n3cc(C(=O)O)cn3)cc2C#N)cc1] | 1-[4-cyano-5-(4-methanesulfonamidophenyl)pyridine-2-yl]-1H-pyrazole-4-carboxylic acid |
| 70 | 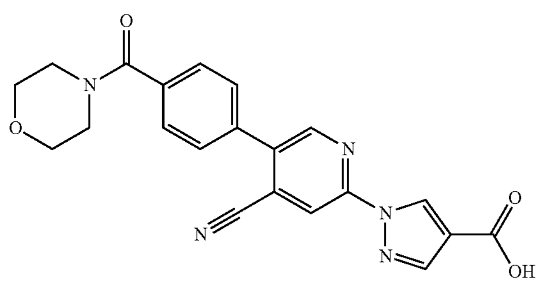 [SMILES: N#Cc1cc(-n2cc(C(=O)O)cn2)ncc1-c1ccc(C(=O)N2CCOCC2)cc1] | 1-(4-cyano-5-{4-[(morpholine-4-yl)carbonyl]phenyl}pyridine-2-yl)-1H-pyrazole-4-carboxylic acid |
| 71 | 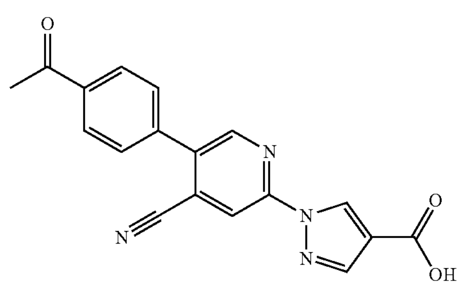 [SMILES: CC(=O)c1ccc(-c2cnc(-n3cc(C(=O)O)cn3)cc2C#N)cc1] | 1-[5-(4-acetophenyl)-4-cyanopyridin-2-yl]-1H-pyrazole-4-carboxylic acid |
| 72 | 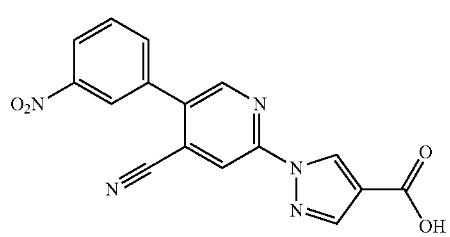 [SMILES: N#Cc1cc(-n2cc(C(=O)O)cn2)ncc1-c1cccc([N+](=O)[O-])c1] | 1-[4-cyano-5-(3-nitrophenyl)pyridin-2-yl]-1H-pyrazole-4-carboxylic acid |
| 73 | 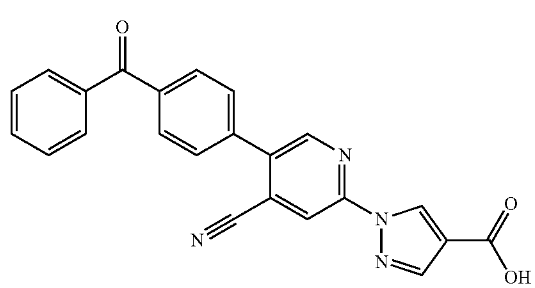 [SMILES: N#Cc1cc(-n2cc(C(=O)O)cn2)ncc1-c1ccc(C(=O)c2ccccc2)cc1] | 1-[5-(4-benzoylphenyl)-4-cyanopyridin-2-yl]-1H-pyrazole-4-carboxylic acid |

| Compound No. | Structure | Name |
|---|---|---|
| 74 | 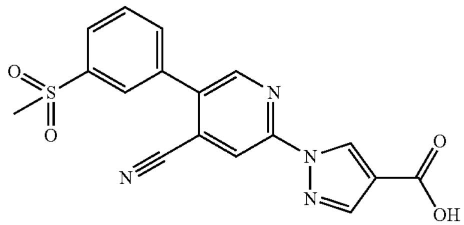 [SMILES: CS(=O)(=O)c1cccc(-c2cnc(-n3cc(C(=O)O)cn3)cc2C#N)c1] | 1-[4-cyano-5-(4-methanesulfonylphenyl)pyridin-2-yl]-1H-pyrazole-4-carboxylic acid |
| 75 | 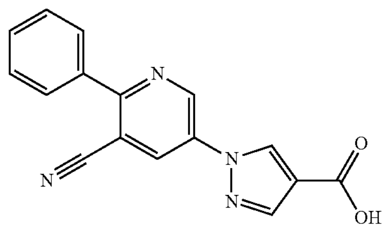 [SMILES: N#Cc1cc(-n2cc(C(=O)O)cn2)cnc1-c1ccccc1] | 1-(5-cyano-6-phenylpyridin-3-yl)-1H-pyrazole-4-carboxylic acid |
| 76 | 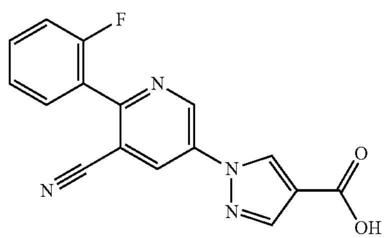 [SMILES: N#Cc1cc(-n2cc(C(=O)O)cn2)cnc1-c1ccccc1F] | 1-[5-cyano-6-(2-fluorophenyl)pyridin-3-yl]-1H-pyrazole-4-carboxylic acid |
| 77 | 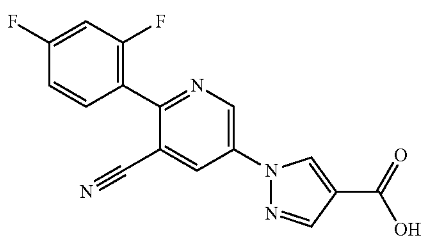 [SMILES: N#Cc1cc(-n2cc(C(=O)O)cn2)cnc1-c1ccc(F)cc1F] | 1-[5-cyano-6-(2,4-difluorophenyl)pyridin-3-yl]-1H-pyrazole-4-carboxylic acid |
| 78 | 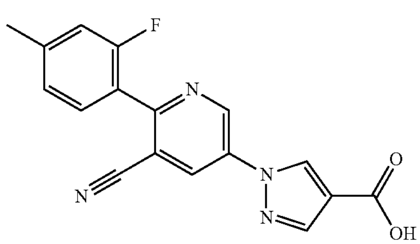 [SMILES: Cc1ccc(-c2ncc(-n3cc(C(=O)O)cn3)cc2C#N)c(F)c1] | 1-[5-cyano-6-(2-fluoro-4-methylphenyl)pyridin-3-yl]-1H-pyrazole-4-carboxylic acid |
| 79 | 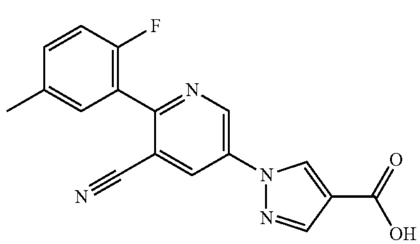 [SMILES: Cc1ccc(F)c(-c2ncc(-n3cc(C(=O)O)cn3)cc2C#N)c1] | 1-[5-cyano-6-(2-fluoro-5-methylphenyl)pyridin-3-yl]-1H-pyrazole-4-carboxylic acid |

-continued

| Compound No. | Structure | Name |
|---|---|---|
| 80 | 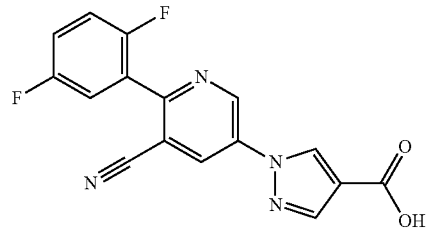 [SMILES: N#Cc1cc(-n2cc(C(=O)O)cn2)cnc1-c1cc(F)ccc1F] | 1-[5-cyano-6-(2,5-difluorophenyl)pyridin-3-yl]-1H-pyrazole-4-carboxylic acid |
| 81 | 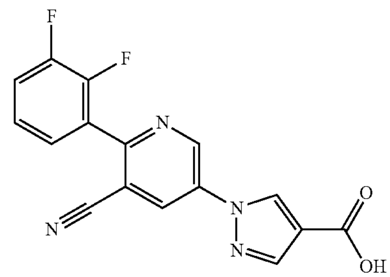 [SMILES: N#Cc1cc(-n2cc(C(=O)O)cn2)cnc1-c1cccc(F)c1F] | 1-[5-cyano-6-(2,3-difluorophenyl)pyridin-3-yl]-1H-pyrazole-4-carboxylic acid |
| 82 | 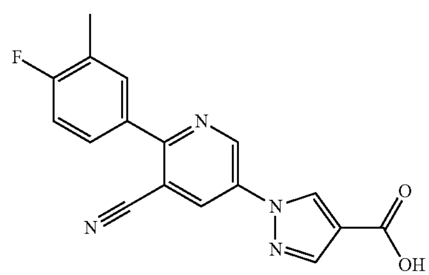 [SMILES: Cc1cc(-c2ncc(-n3cc(C(=O)O)cn3)cc2C#N)ccc1F] | 1-[5-cyano-6-(4-fluoro-3-methylphenyl)pyridin-3-yl]-1H-pyrazole-4-carboxyic acid |
| 83 | 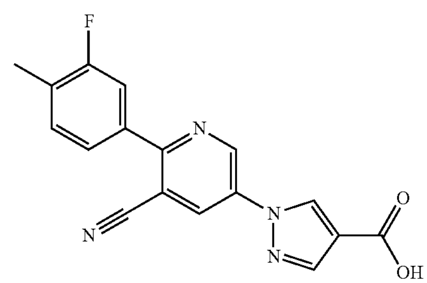 [SMILES: Cc1ccc(-c2ncc(-n3cc(C(=O)O)cn3)cc2C#N)cc1F] | 1-[5-cyano-6-(3-fluoro-4-methylphenyl)pyridin-3-yl]-1H-pyrazole-4-carboxylic acid |
| 84 | 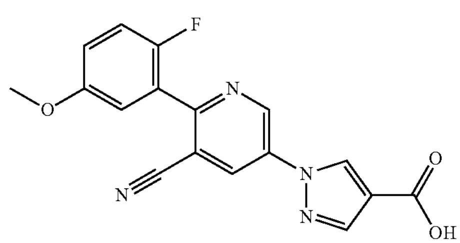 [SMILES: COc1ccc(F)c(-c2ncc(-n3cc(C(=O)O)cn3)cc2C#N)c1] | 1-[5-cyano-6-(2-fluoro-5-methoxyphenyl)pyridin-3-yl]-1H-pyrazole-4-carboxylic acid |
| 85 | 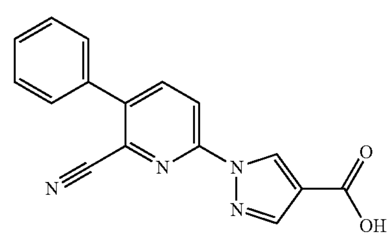 [SMILES: N#Cc1nc(-n2cc(C(=O)O)cn2)ccc1-c1ccccc1] | 1-(6-cyano-5-phenylpyridin-2-yl)-1H-pyrazole-4-carboxylic acid |

-continued

| Compound No. | Structure | Name |
|---|---|---|
| 86 | 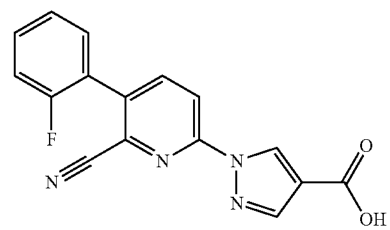 [SMILES: N#Cc1nc(-n2cc(C(=O)O)cn2)ccc1-c1ccccc1F] | 1-[6-cyano-5-(2-fluorophenyl)pyridin-2-yl]-1H-pyrazole-4-carboxylic acid |
| 87 | 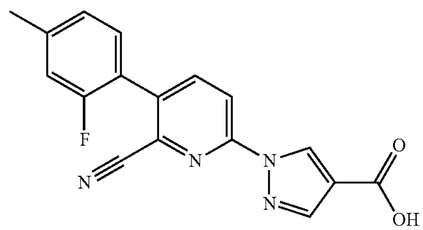 [SMILES: Cc1ccc(-c2ccc(-n3cc(C(=O)O)cn3)nc2C#N)c(F)c1] | 1-[6-cyano-5-(2-fluoro-4-methylphenyl)pyridin-2-yl]-1H-pyrazole-4-carboxylic acid |
| 88 | 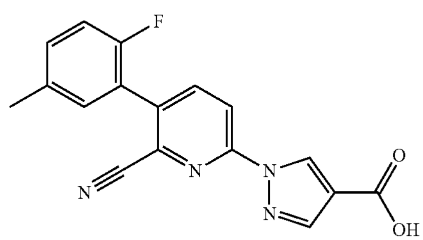 [SMILES: Cc1ccc(F)c(-c2ccc(-n3cc(C(=O)O)cn3)nc2C#N)c1] | 1-[6-cyano-5-(2-fluoro-5-methylphenyl)pyridin-2-yl]-1H-pyrazole-4-carboxylic acid |
| 89 | 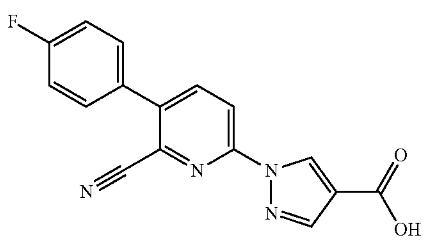 [SMILES: N#Cc1nc(-n2cc(C(=O)O)cn2)ccc1-c1ccc(F)cc1] | 1-[6-cyano-5-(2-fluoro-5-methylphenyl)pyridin-2-yl]-1H-pyrazole-4-carboxylic acid |
| 90 | 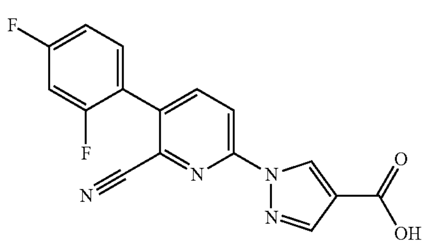 [SMILES: N#Cc1nc(-n2cc(C(=O)O)cn2)ccc1-c1ccc(F)cc1F] | 1-[6-cyano-5-(2,4-difluorophenyl)pyridin-2-yl]-1H-pyrazole-4-carboxylic acid |
| 91 | 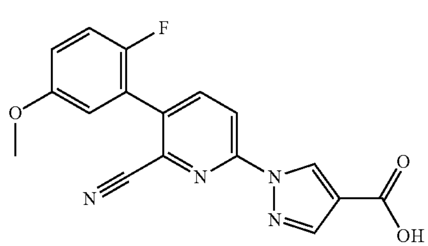 [SMILES: COc1ccc(F)c(-c2ccc(-n3cc(C(=O)O)cn3)nc2C#N)c1] | 1-[6-cyano-5-(2-fluoro-5-methoxyphenyl)pyridin-2-yl]-1H-pyrazole-4-carboxylic acid |

-continued

| Compound No. | Structure | Name |
|---|---|---|
| 92 | 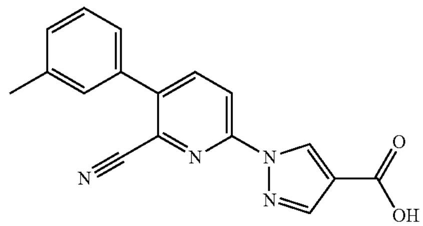 [SMILES: Cc1cccc(-c2ccc(-n3cc(C(=O)O)cn3)nc2C#N)c1] | 1-[6-cyano-5-(3-methylphenyl)pyridin-2-yl]-1H-pyrazole-4-carboxylic acid |
| 93 | 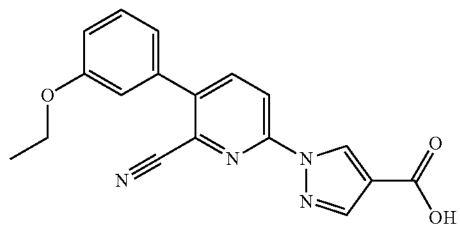 [SMILES: CCOc1cccc(-c2ccc(-n3cc(C(=O)O)cn3)nc2C#N)c1] | 1-[6-cyano-5-(3-ethoxyphenyl)pyridin-2-yl]-1H-pyrazole-4-carboxylic acid |
| 94 | 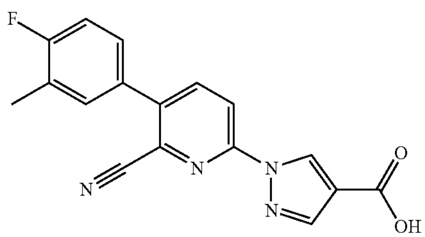 [SMILES: Cc1cc(-c2ccc(-n3cc(C(=O)O)cn3)nc2C#N)ccc1F] | 1-[6-cyano-5-(4-fluoro-3-methylphenyl)pyridin-2-yl]-1H-pyrazole-4-carboxylic acid |
| 95 | 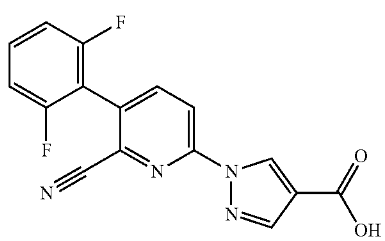 [SMILES: N#Cc1nc(-n2cc(C(=O)O)cn2)ccc1-c1c(F)cccc1F] | 1-[6-cyano-5-(2,6-difluorophenyl)pyridin-2-yl]-1H-pyrazole-4-carboxylic acid |
| 96 | 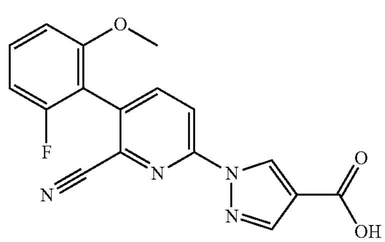 [SMILES: COc1cccc(F)c1-c1ccc(-n2cc(C(=O)O)cn2)nc1C#N] | 1-[6-cyano-5-(2-fluoro-6-methoxyphenyl)pyridin-2-yl]-1H-pyrazole-4-carboxylic acid |
| 97 | 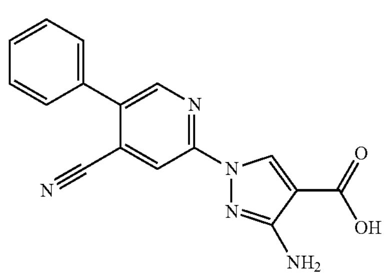 [SMILES: N#Cc1cc(-n2cc(C(=O)O)c(N)n2)ncc1-c1ccccc1] | 3-amino-1-(4-cyano-5-phenylpyridin-2-yl)-1H-pyrazole-4-carboxylic acid |

-continued

| Compound No. | Structure | Name |
|---|---|---|
| 98 | 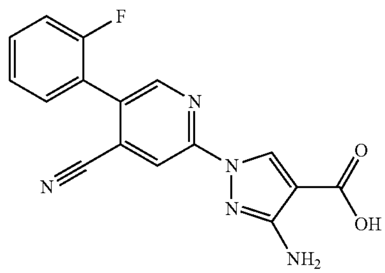 [SMILES: N#Cc1cc(-n2cc(C(=O)O)c(N)n2)ncc1-c1ccccc1F] | 3-amino-1-[4-cyano-5-(2-fluorophenyl)pyridin-2-yl]-1H-pyrazole-4-carboxylic acid |
| 99 | 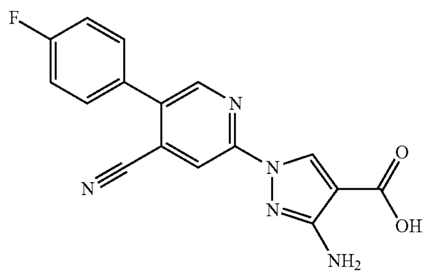 [SMILES: N#Cc1cc(-n2cc(C(=O)O)c(N)n2)ncc1-c1ccc(F)cc1] | 3-amino-1-[4-cyano-5-(4-fluorophenyl)pyridin-2-yl]-1H-pyrazole-4-carboxylic acid |
| 100 | 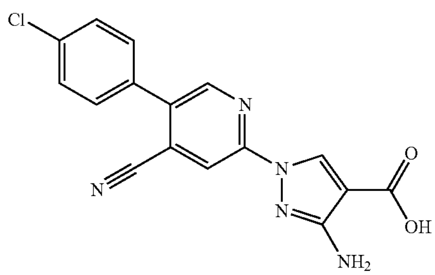 [SMILES: N#Cc1cc(-n2cc(C(=O)O)c(N)n2)ncc1-c1ccc(Cl)cc1] | 3-amino-1-[4-cyano-5-(4-chlorophenyl)pyridin-2-yl]-1H-pyrazole-4-carboxylic acid |
| 101 | 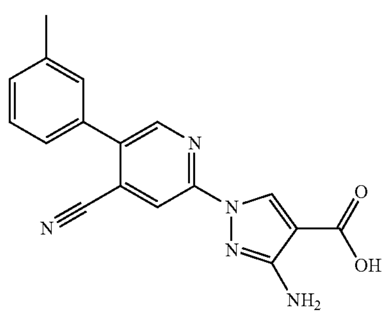 [SMILES: Cc1cccc(-c2cnc(-n3cc(C(=O)O)c(N)n3)cc2C#N)c1] | 3-amino-1-[4-cyano-5-(3-methylphenyl)pyridin-2-yl]-1H-pyrazole-4-carboxylic acid |
| 102 | 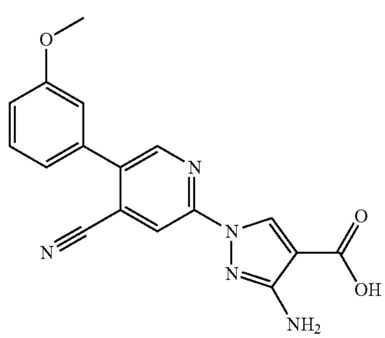 [SMILES: COc1cccc(-c2cnc(-n3cc(C(=O)O)c(N)n3)cc2C#N)c1] | 3-amino-1-[4-cyano-5-(3-methoxyphenyl)pyridin-2-yl]-1H-pyrazole-4-carboxylic acid |

| Compound No. | Structure | Name |
|---|---|---|
| 103 | 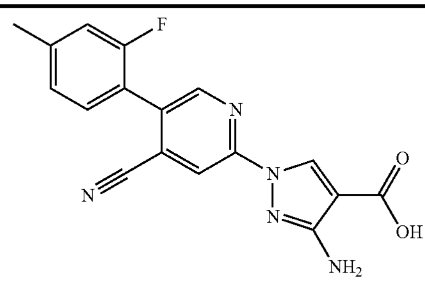 | 3-amino-1-[4-cyano-5-(2-fluoro-4-methylphenyl)pyridin-2-yl]-1H-pyrazole-4-carboxylic acid |
| 104 | 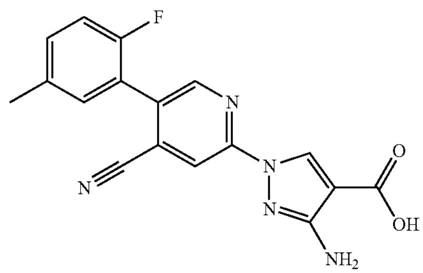 [SMILES: Cc1ccc(F)c(-c2cnc(-n3cc(C(=O)O)c(N)n3)cc2C#N)c1] | 3-amino-1-[4-cyano-5-(2-fluoro-5-methylphenyl)pyridin-2-yl]-1H-pyrazole-4-carboxylic acid |
| 105 | 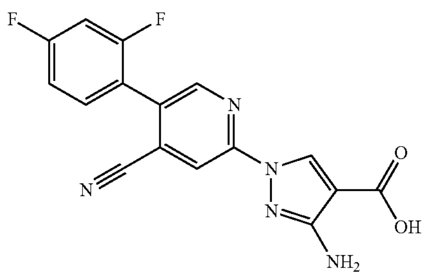 [SMILES: N#Cc1cc(-n2cc(C(=O)O)c(N)n2)ncc1-c1ccc(F)cc1F] | 3-amino-1-[4-cyano-5-(2,4-difluorophenyl)pyridin-2-yl]-1H-pyrazole-4-carboxylic acid |
| 106 | 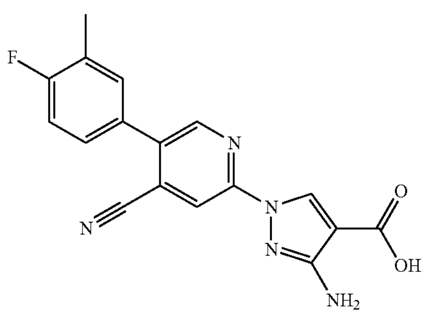 [SMILES: Cc1cc(-c2cnc(-n3cc(C(=O)O)c(N)n3)cc2C#N)ccc1F] | 3-amino-1-[4-cyano-5-(4-fluoro-3-methylphenyl)pyridin-2-yl]-1H-pyrazole-4-carboxylic acid |
| 107 | 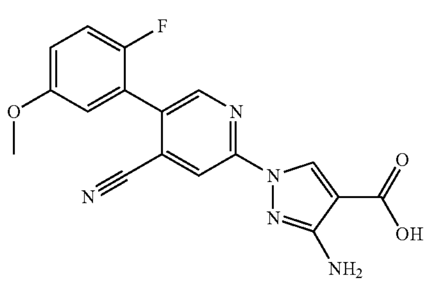 [SMILES: COc1ccc(F)c(-c2cnc(-n3cc(C(=O)O)c(N)n3)cc2C#N)c1] | 3-amino-1-[4-cyano-5-(2-fluoro-5-methoxyphenyl)pyridine-2-yl]-1H-pyrazole-4-carboxylic acid |

Comp. No. denotes compound number in the above tables.

Of these compounds, more preferred are compounds 1, 2, 5, 6, 7, 10, 13, 14, 15, 16, 19, 20, 21, 22, 29, 30, 31, 32, 33, 34, 35, 36, 37, 38, 39, 41, 42, 43, 44, 47, 48, 50, 51, 52, 53, 54, 55, 57, 59, 61, 63, 64, 65, 66, 68, 69, 70, 71, 73, 97, 98, 99, 100, 101, 102, 103, 104, 105, 106, and 107, and further preferred are compounds 1, 5, 10, 14, 19, 21, 33, 97, and 98.

In the compound represented by the foregoing formula (II) which can be used as an intermediate in the manufacture of the compounds represented by the foregoing formula (I)

of the present invention, the definitions of A, Q, R, $R^1$, $R^2$, $R^3$, $R^4$, $R^5$, X, Y, and Z are the same as those in the foregoing formula (I). W represents a halogen atom, a methanesulfonyloxy group, a p-toluenesulfonyloxy group, a trifluoromethanesulfonyloxy group, or a cyano group. W is more preferably a halogen atom or a cyano group, and particularly preferably a cyano group. $R^6$ represents a carboxyl-protecting group. The definition of the carboxyl-protecting group is as set out above, and it is preferably a methyl, ethyl, or benzyl group.

Further, in the compound represented by the foregoing formula (III) which can be used as an intermediate in the manufacture of the compounds represented by the foregoing formula (I) of the present invention, the definitions of R, $R^1$, $R^5$, X, Y and Z are the same as those in the foregoing formula (I). V represents a halogen atom, a methanesulfonyloxy group, a p-toluenesulfonyloxy group, a trifluoromethanesulfonyloxy group, a hydroxyl group, or a benzyloxy group. V is preferably a halogen atom, a trifluoromethanesulfonyloxy group, a hydroxyl group, or a benzyloxy group. W represents a halogen atom, a methanesulfonyloxy group, a p-toluenesulfonyloxy group, a trifluoromethanesulfonyloxy group, or a cyano group. W is more preferably a halogen atom or a cyano group, and particularly preferably a cyano group. $R^6$ represents a carboxyl-protecting group. The definition of the carboxyl-protecting group is as set out above, and it is preferably a methyl, ethyl, or benzyl group.

In the compound represented by the foregoing formula (IV) which can be used as an intermediate in the manufacture of the compounds represented by the foregoing formula (I) of the present invention, the definitions of A, Q, $R^2$, $R^3$, $R^4$, $R^5$, X, Y, and Z are the same as those in the foregoing formula (I). $X^2$ represents a halogen atom, a methanesulfonyloxy group, a p-toluenesulfonyloxy group or a trifluoromethanesulfonyloxy group. A halogen atom is preferable.

<General Synthetic Methods>

Compounds of formula (I) of the present invention and intermediates can be synthesized according, for example, to any of the synthetic methods as described below. It should be noted that, in each formula, A, R, $R^1$, Q, X, Y, and Z are as defined for formula (I). In addition, the reagents, solvents, etc. shown in chemical formulae as conditions are merely illustrative, as mentioned also in the text. If necessary, each substituent may be protected with an appropriate protecting group and may be deprotected at an appropriate stage. It should be noted that, as appropriate protecting groups and methods for their removal, protecting groups of each substituent which are widely used in the art and known methods, for example those described in PROTECTIVE GROUPS in ORGANIC SYNTHESIS, THIRD EDITION, John Wiley & Sons, Inc., may be employed.

In addition, when abbreviations are used for substituents, reagents, and solvents in the text or in tables, they stand for the following.

DMF: N,N-dimethylformamide
THF: tetrahydrofuran
Ph: phenyl
TFA: trifluoroacetic acid Synthetic Method (A)
Synthesis of Compound (A-2)

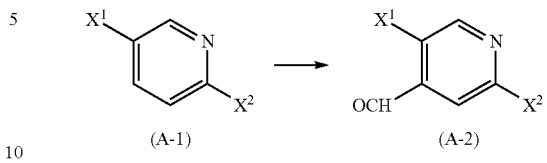

(In the formulae, $X^1$ and $X^2$ represent leaving groups) Leaving groups represented by $X^1$ and $X^2$ include a halogen atom, a methanesulfonyloxy group, a p-toluenesulfonyloxy group, a trifluoromethanesulfonyloxy group, and the like. This reaction is a method for synthesizing compound (A-2) by lithiation or sodiation of the 4-position of the pyridine of compound (A-1) using base, followed by formylation using a formylating agent. Bases include lithium diisopropylamine (LDA) prepared from diisopropylamine and n-butyllithium, and the like. Formylating agents include N,N-dimethylformamide (DMF), N-formylmorpholine, and the like. This reaction is carried out by reacting compound (A-1) with an equivalent amount or a small excess of a base in an inert solvent at −78° C. to 0° C., then adding an equivalent amount or an excess of formylating agent, and allowing them to react for normally 0.5 to 5 hours. It is preferred that this reaction is performed under an inert gas atmosphere such as nitrogen. Solvents here include, though not particularly limited, for example, ethers such as diethyl ether, tetrahydrofuran (THF), 1,4-dioxane, 1,2-dimethoxyethane, and 1,2-diethoxyethane, or a mixed solvent thereof, and the like.

Synthesis of Compound (A-4)

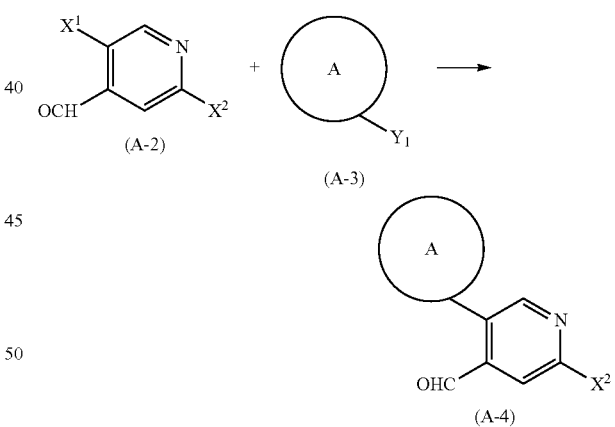

(In the formulae, $X^1$ and $X^2$ represent leaving groups, and $Y^1$ represents —B(OH)$_2$ or —B(OR$^7$)OR$^8$, wherein $R^7$ and $R^8$ are the same or different from each other and represent $C_{1-6}$ alkyl groups, or $R^7$ and $R^8$ are taken together to represent a $C_{1-6}$ alkylene group.) This reaction is a method for synthesizing compound (A-4) by coupling compounds (A-2) and (A-3). The leaving groups represented by $X^1$ and $X^2$ include a halogen atom, a methanesulfonyloxy group, a p-toluenesulfonyloxy group, a trifluoromethanesulfonyloxy group, and the like. This reaction is carried out by using equivalent amounts of compounds (A-2) and (A-3) or by using either one in excess and allowing them to react in an inert solvent in the presence of a base and a palladium catalyst between room temperature and heating under reflux for normally 0.5 to 2 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, alcohols such as methanol, ethanol, 2-propanol, and butanol, N,N-dimethylformamide (DMF), N-methylpyrrolidone, dimethyl sulfoxide (DMSO), water, or a mixed solvent thereof, and the like. Bases include sodium hydroxide, potassium hydroxide, lithium hydroxide, inorganic salts such as sodium carbonate, potassium carbonate, cesium carbonate, and tripotassium phosphate, metal alkoxides such as sodium ethoxide and sodium methoxide, or solutions obtained by diluting these bases with water etc., and the like. As the palladium catalyst, tetrakis(triphenylphosphine)palladium, dichlorobis(triphenylphosphine)palladium, palladium chloride-1,1'-bis(diphenylphosphino)ferrocene, or the like is preferred.

Synthesis of Compound (A-5)

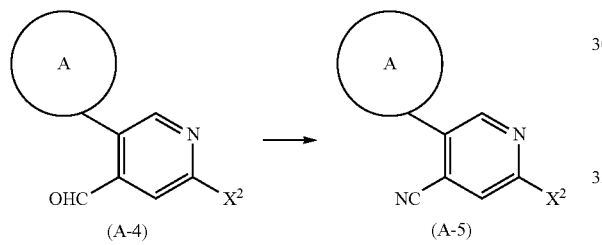

(A-4)    (A-5)

(In the formulae, $X^2$ represents a leaving group.) Leaving groups represented by $X^2$ include a halogen atom, a methanesulfonyloxy group, a p-toluenesulfonyloxy group, a trifluoromethanesulfonyloxy group, and the like. This reaction is a conversion reaction of the formyl group into a cyano group and is carried out by reacting the aromatic aldehyde derivative represented by the above formula (A-4) with hydroxylamine. As the hydroxylamine, such as the hydrochloride may be used; in that case, however, it is preferred that an appropriate basic substance is added. In addition, it is possible to accelerate the reaction by adding 1.0 to 3.0 equivalents of acetic anhydride, acetyl chloride, trichloroacetyl chloride, and the like. The amount of hydroxylamine or its salts used in this reaction is normally 1 or more equivalents and preferably 1.0 to 2.0 equivalents. When a basic substance is used, 1.0 to 3.0 equivalents relative to the salt of hydroxylamine are used. As the basic substance used, a carboxylate such as sodium formate, potassium formate, or sodium acetate, a carbonate such as potassium carbonate, sodium carbonate, or sodium hydrogencarbonate, or an organic amine base such as triethylamine, pyridine, or 4-aminopyridine is used. The reaction is carried out by allowing the reactants to react in an inert solvent in the presence of a base between room temperature and heating under reflux for normally 0.5 hours to 3 days. It is preferred that this reaction is performed under an inert gas atmosphere such as nitrogen. Solvents used in this reaction include solvents such as acetic acid, formic acid, toluene, benzene, pyridine, ethyl acetate, dichloromethane, 1,2-dichloroethane, chloroform, carbon tetrachloride, diethyl ether, tetrahydrofuran, 1,4-dioxane, 1,2-dimethoxyethane, 1,2-diethoxyethane, N,N-dimethylformamide (DMF), N-methylpyrrolidone, dimethyl sulfoxide (DMSO), methanol, ethanol, and 2-propanol.

Synthesis of Compound (A-7)

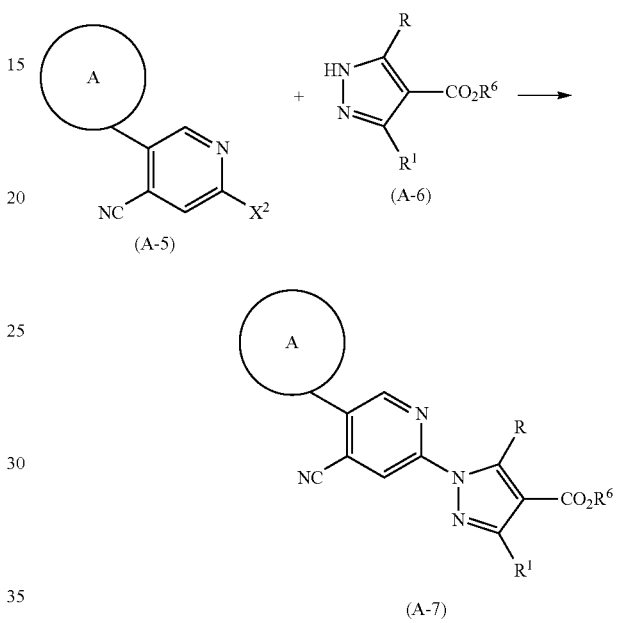

(In the formulae, $R^6$ represents a carboxyl-protecting group and $X^2$ represents a leaving group.) The leaving groups represented by $X^2$ include a halogen atom, a methanesulfonyloxy group, a p-toluenesulfonyloxy group, a trifluoromethanesulfonyloxy group, and the like. This reaction is carried out by using equivalent amounts of compounds (A-5) and (A-6) or by using either one in excess and allowing them to react in a reaction inert solvent in the presence of a base catalyst between room temperature and heating under reflux for normally 0.5 to 3 days. It is preferred that this reaction is performed under an inert gas atmosphere such as nitrogen. Solvents here include, not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, N,N-dimethylformamide (DMF), N-methylpyrrolidone, dimethyl sulfoxide (DMSO) or a mixed solvent thereof, and the like. Bases include sodium hydride, sodium hydroxide, potassium hydroxide, lithium hydroxide, inorganic salts such as sodium carbonate, potassium carbonate, cesium carbonate, metal alkoxides such as sodium ethoxide and sodium methoxide, or an organic amine base such as triethylamine, N-ethyl-N,N-diisopropylamine (DIPEA) or 1,8-diazabicyclo[5.4.0]-7-undecene (DBU), and the like.

Synthesis of Compound (A-8)

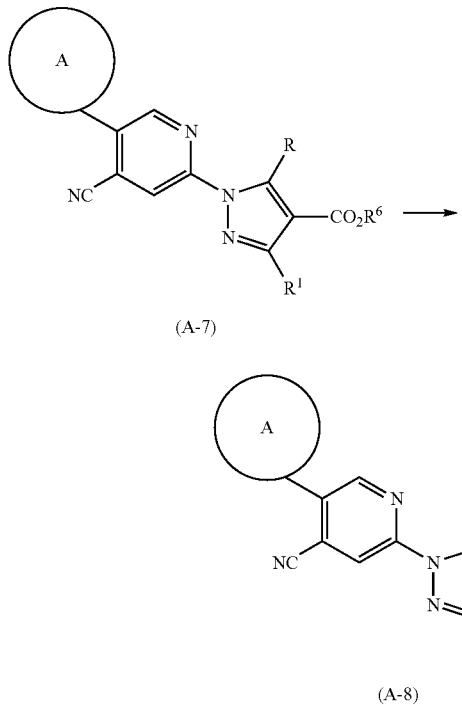

(In the formulae, $R^6$ represents a carboxyl-protecting group.) This synthetic method is a method for synthesizing the compound (A-8) of the invention by deprotecting the protecting group $R^6$ of compound (A-7) using an acid or a base etc.

This reaction is carried out by allowing compound (A-7) to react with an equivalent amount or an excess of acid or base in an inert solvent between room temperature and heating under reflux for normally 0.5 to 5 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, alcohols such as methanol, ethanol, 2-propanol, and butanol, N,N-dimethylformamide (DMF), N-methylpyrrolidone, dimethyl sulfoxide (DMSO), water, or a mixed solvent thereof, and the like. Acids include inorganic acids such as hydrogen chloride, hydrogen bromide, sulfuric acid, nitric acid, phosphoric acid or a solution of the acids diluted with water or organic solvents. Bases include sodium hydroxide, potassium hydroxide, lithium hydroxide, inorganic salts such as sodium carbonate, potassium carbonate, cesium carbonate, and tripotassium phosphate, metal alkoxides such as sodium ethoxide and sodium methoxide, or solutions obtained by diluting these bases with water etc., and the like.

Compound (A-7), for example, can be synthesized also according to the Synthetic Method (B) described below.

Synthetic Method (B)
Synthesis of Compound (B-1)

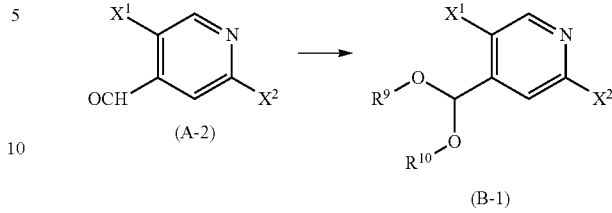

(In the formulae, $X^1$ and $X^2$ represent leaving groups. $R^9$ and $R^{10}$ are the same or different from each other and represent $C_{1-6}$ alkyl groups, or $R^9$ and $R^{10}$ are taken together to represent a $C_{1-6}$ alkylene group.) Leaving groups represented by $X^1$ and $X^2$ include a halogen atom, a methanesulfonyloxy group, a p-toluenesulfonyloxy group, a trifluoromethanesulfonyloxy group, and the like. This reaction is carried out by allowing compound (A-2) to react with an equivalent amount or an excess of alcohol or trialkyl orthoformate in an inert solvent in the presence of an acid between room temperature and heating under reflux for normally 0.5 to 2 days. As the acid here, a Brønsted acid such as hydrogen chloride, trifluoroacetic acid, tosylsulfonic acid, or camphorsulfonic acid, a Lewis acid such as trimethylsilyl trifluorosulfonate or trifluoroborane, or the like is used. Solvents used in this reaction include, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, chloroform, and carbon tetrachloride, alcohols such as methanol, ethanol, and 2-propanol, or a mixed solvent thereof, and the like.

Synthesis of Compound (B-2)

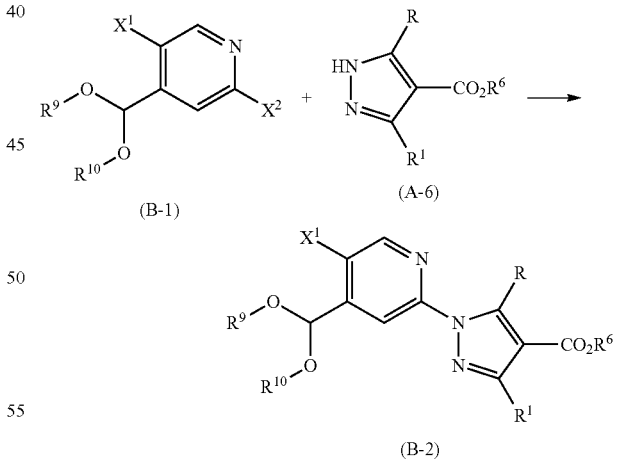

(In the formulae, $R^6$ represents a carboxyl-protecting group, and $X^1$ and $X^2$ represent leaving groups. $R^9$ and $R^{10}$ are the same or different from each other and represent $C_{1-6}$ alkyl groups, or $R^9$ and $R^{10}$ are taken together to represent a $C_{1-6}$ alkylene group.) Leaving groups represented by $X^1$ and $X^2$ include a halogen atom, a methanesulfonyloxy group, a p-toluenesulfonyloxy group, a trifluoromethanesulfonyloxy group, and the like. This reaction is carried out by using equivalent amounts of compounds (B-1) and (A-6) or by using either one in excess and allowing them to react in an inert solvent in the presence of a base catalyst between room temperature and heating under reflux for normally 0.5 hours to 3 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, N,N-dimethylformamide (DMF), N-methylpyrrolidone, dimethyl sulfoxide (DMSO) or a mixed solvent thereof, and the like. Bases include sodium hydride, sodium hydroxide, potassium hydroxide, lithium hydroxide, inorganic salts such as sodium carbonate, potassium carbonate, cesium carbonate, sodium hydride, metal alkoxides such as sodium ethoxide and sodium methoxide, or an organic amine base such as triethylamine, N-ethyl-N, N-diisopropylamine (DIPEA) or 1,8-diazabicyclo(5.4.0)-7-undecene (DBU), and the like.

Synthesis of Compound (B-3)

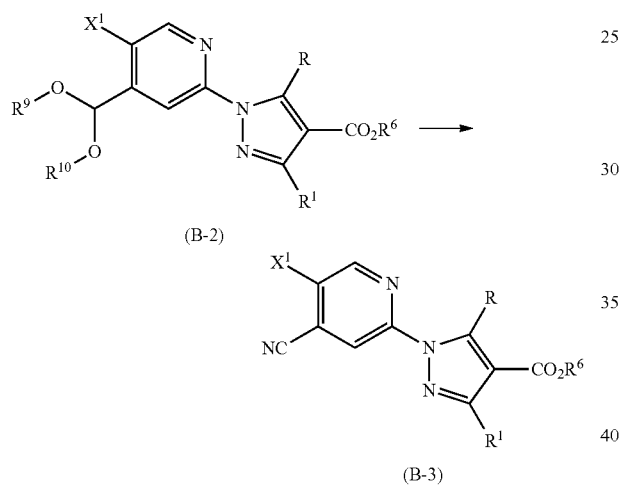

(In the formulae, $R^6$ represents a carboxyl-protecting group and $X^1$ represents leaving groups. $R^9$ and $R^{10}$ are the same or different from each other and represent $C_{1-6}$ alkyl groups, or $R^9$ and $R^{10}$ are taken together to represent a $C_{1-6}$ alkylene group.) This synthetic method is a method for synthesizing compound (B-3) by cyanation of compound (B-2). Leaving group represented by $X^1$ includes a halogen atom, a methanesulfonyloxy group, a p-toluenesulfonyloxy group, a trifluoromethanesulfonyloxy group, and the like. In this reaction, cyanation is carried out by converting the aromatic dialkoxy acetal derivative represented by the above formula (B-2) into an aldehyde derivative via deprotection reaction and subsequently reacting it with hydroxylamine. This reaction is a conversion reaction of the formyl group into a cyano group and is carried out by reacting the aromatic aldehyde derivative represented by the above formula (A-4) with hydroxylamine. As the hydroxylamine, salts such as the hydrochloride may be used; in that case, however, it is preferred that an appropriate basic substance is added. In addition, it is possible to accelerate the reaction by adding 1.0 to 3.0 equivalents of acetic anhydride, acetyl chloride, trichloroacetyl chloride, and the like. The amount of hydroxylamine or its salts used in this reaction is normally 1 or more equivalents and preferably 1.0 to 2.0 equivalents.

When a basic substance is used, 1.0 to 3.0 equivalents relative to the salt of hydroxylamine are used. As the basic substance used, a carboxylate such as sodium formate, potassium formate, or sodium acetate, a carbonate such as potassium carbonate, sodium carbonate, or sodium hydrogencarbonate, or an organic amine salt such as triethylamine, pyridine, or 4-aminopyridine is used. The reaction is carried out by allowing them to react in an inert solvent in the presence of a base between room temperature and heating under reflux for normally 0.5 hours to 3 days. It is preferred that this reaction is performed under an inert gas atmosphere such as nitrogen. Solvents used in this reaction include solvents such as acetic acid, formic acid, toluene, benzene, pyridine, ethyl acetate, dichloromethane, 1,2-dichloroethane, chloroform, carbon tetrachloride, diethyl ether, tetrahydrofuran (THF), 1,4-dioxane, 1,2-dimethoxyethane, 1,2-diethoxyethane, N,N-dimethylformamide (DMF), N-methylpyrrolidone, dimethyl sulfoxide (DMSO), methanol, ethanol, and 2-propanol or a mixed solvent thereof.

Synthesis of Compound (A-7)

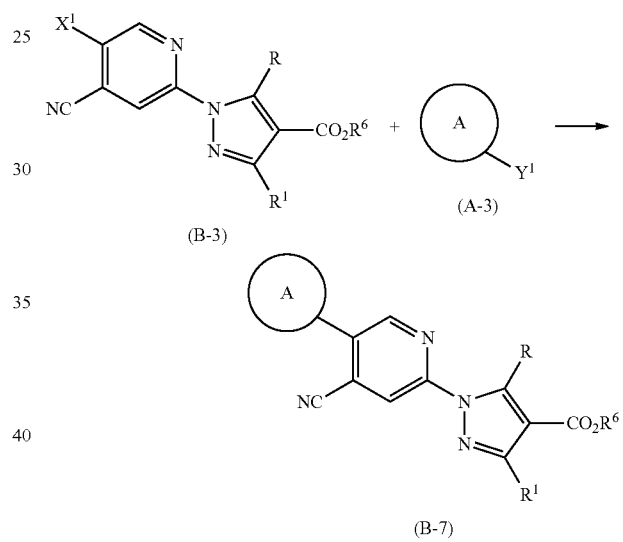

(In the formulae, $R^6$ represents a carboxyl-protecting group and $X^1$ represents a leaving group. And $Y^1$ represents —B(OH)$_2$ or —B(OR$^7$)OR$^8$, wherein $R^7$ and $R^8$ are the same or different from each other and represent $C_{1-6}$ alkyl groups, or $R^7$ and $R^8$ are taken together to represent a $C_{1-6}$ alkylene group.) This reaction is a method for synthesizing compound (A-7) by coupling compounds (B-3) and (A-3). The leaving groups represented by $X^1$ include a halogen atom, a methanesulfonyloxy group, a p-toluenesulfonyloxy group, a trifluoromethanesulfonyloxy group, and the like. This reaction is carried out by using equivalent amounts of compounds (B-3) and (A-3) or by using either one in excess and allowing them to react in an inert solvent in the presence of a base and a palladium catalyst between room temperature and heating under reflux for normally 0.5 to 2 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, alcohols such as methanol, ethanol, 2-propanol, and butanol, N,N-dimethylformamide (DMF), N-methylpyrrolidone, dimethyl sulfoxide (DMSO), water, or a mixed solvent thereof, and the like. Bases include sodium hydroxide, potassium hydroxide, lithium hydroxide, inorganic salts such as sodium carbonate, potassium carbonate, cesium carbonate, and tripotassium phosphate, metal alkoxides such as sodium ethoxide and sodium methoxide, or solutions obtained by diluting these bases with water etc., and the like. As the palladium catalyst, tetrakis(triphenylphosphine)palladium, dichlorobis(triphenylphosphine)palladium, palladium chloride-1,1'-bis(diphenylphosphino)ferrocene, or the like is preferred.

Synthetic Method (C)

Synthesis of Compound (C-2)

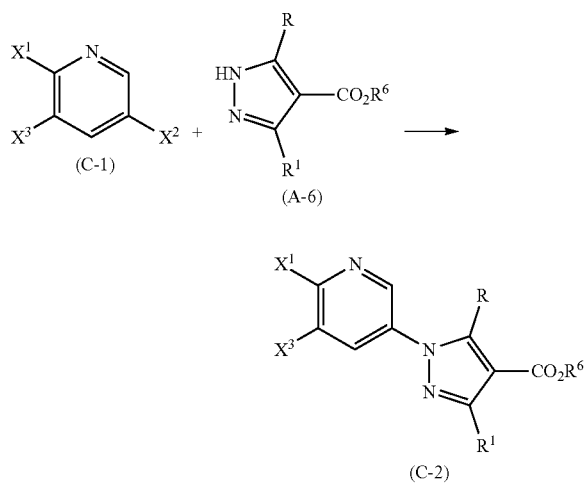

(In the formulae, $R^6$ represents a carboxyl-protecting group. $X^1$, $X^2$ and $X^3$ represent leaving groups.) The leaving groups represented by $X^1$, $X^2$ and $X^3$ include a halogen atom, a methanesulfonyloxy group, a p-toluenesulfonyloxy group, a trifluoromethanesulfonyloxy group, and the like. This reaction is carried out by using equivalent amounts of compounds (C-1) and (A-6) or by using either one in excess and allowing them to react in an inert solvent in the presence of a base between room temperature and heating under reflux for normally 0.5 hours to 3 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, N,N-dimethylformamide (DMF), N-methylpyrrolidone, dimethyl sulfoxide (DMSO) or a mixed solvent thereof, and the like. Bases include inorganic salts such as sodium hydroxide, potassium hydroxide, lithium hydroxide, sodium carbonate, potassium carbonate, cesium carbonate, sodium hydride, metal alkoxides such as sodium ethoxide and sodium methoxide, or an organic amine base such as triethylamine, N-ethyl-N,N-diisopropylamine (DIPEA) or 1,8-diazabicyclo(5,4,0)-7-undecene (DBU), and the like.

Synthesis of Compound (C-3)

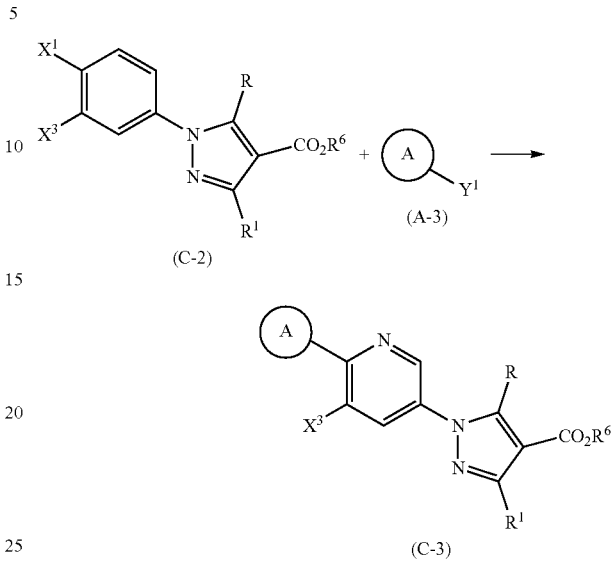

(In the formulae, $R^6$ represents a carboxyl-protecting group and $X^1$ and X3 represents a leaving group. And $Y^1$ represents $-B(OH)_2$ or $-B(OR^7)OR^8$, wherein $R^7$ and $R^8$ are the same or different from each other and represent $C_{1-6}$ alkyl groups, or $R^7$ and $R^8$ are taken together to represent a $C_{1-6}$ alkylene group.) This reaction is a method for synthesizing compound (C-3) by coupling compounds (C-2) and (A-3). The leaving groups represented by $X^1$ and $X^3$ include a halogen atom, a methanesulfonyloxy group, a p-toluenesulfonyloxy group, a trifluoromethanesulfonyloxy group, and the like. This reaction is carried out by using equivalent amounts of compounds (C-2) and (A-3) or by using either one in excess and allowing them to react in an inert solvent in the presence of a base and a palladium catalyst between room temperature and heating under reflux for normally 0.5 to 2 days. It is preferred that this reaction is performed under an inert gas atmosphere such as nitrogen. Solvents here include, though not particularly limited to, for example, aromatic hydrocarbons such as benzene, toluene, and xylene, ethers such as diethyl ether, tetrahydrofuran (THF), 1,4-dioxane, 1,2-dimethoxyethane; and 1,2-diethoxyethane, halogenated hydrocarbons such as dichloromethane, 1,2-dichloroethane, and chloroform, alcohols such as methanol, ethanol, 2-propanol, and butanol, N,N-dimethylformamide (DMF), N-methylpyrrolidone, dimethyl sulfoxide (DMSO), water, or mixed a solvent thereof, and the like. Bases include sodium hydroxide, potassium hydroxide, lithium hydroxide, inorganic salts such as sodium carbonate, potassium carbonate, cesium carbonate, and tripotassium phosphate, metal alkoxides such as sodium ethoxide and sodium methoxide, or solutions obtained by diluting these bases with water etc., and the like. As the palladium catalyst, tetrakis(triphenylphosphine)palladium, dichlorobis(triphenylphosphine)palladium, palladium chloride-1,1'-bis(diphenylphosphino)ferrocene, or the like is preferred.

Synthesis of Compound (C-4)

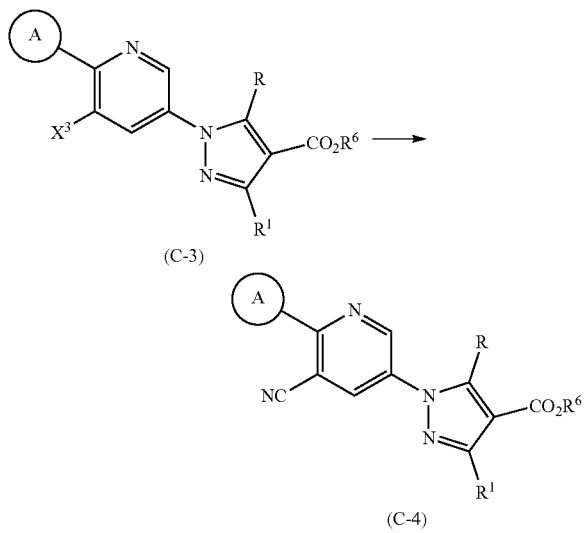

(C-3)

(C-4)

Synthesis of Compound (C-5)

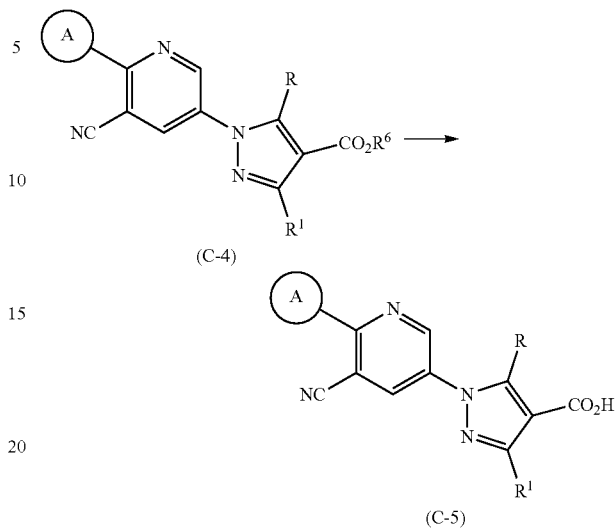

(C-4)

(C-5)

(In the formulae, $R^6$ represents a carboxyl-protecting group. $X^3$ represents a leaving group.) This synthetic method is a method for synthesizing compound (C-4) by cyanation of compound (C-3). The leaving group represented by $X^3$ includes a halogen atom and the like. This reaction is a reaction that replaces the leaving group $X^3$ with a cyano group, and is carried out by reacting the above formula (C-3) with a cyanating reagent. This reaction is carried out by using equivalent amounts of compound (C-3) and the cyanating reagent or by using either one in excess and allowing them to react in an inert solvent, optionally in the presence of a base and a palladium or copper catalyst, between room temperature and heating under reflux for normally 0.5 hours to 2 days. It is preferred that this reaction is performed under an inert gas atmosphere such as nitrogen. As the cyanating reagent used, a cyanating reagent such as potassium cyanide, sodium cyanide, copper cyanide, or zinc cyanide is used. The amount of the cyanating reagent is normally 1 or more equivalents and preferably 1.0 to 2.0 equivalents. When a basic substance is used, 1.0 to 3.0 equivalents relative to compound (C-3) are used. As the basic substance used, a carboxylate such as sodium formate, potassium formate, or sodium acetate, a carbonate such as potassium carbonate, sodium carbonate, or sodium hydrogencarbonate, or an organic amine salt such as triethylamine, pyridine, or 4-aminopyridine is used. Solvents used in this reaction include solvents such as acetic acid, formic acid, toluene, benzene, pyridine, ethyl acetate, dichloromethane, 1,2-dichloroethane, chloroform, carbon tetrachloride, diethyl ether, tetrahydrofuran (THF), 1,4-dioxane, 1,2-dimethoxyethane, 1,2-diethoxyethane, N,N-dimethylformamide (DMF), N-methylpyrrolidone, dimethyl sulfoxide (DMSO), or a mixed solvent thereof. As the palladium catalyst, tetrakis(triphenylphosphine)palladium, dichlorobis(triphenylphosphine)palladium, palladium chloride-1,1'-bis(diphenylphosphino)ferrocene, or the like is preferred. As the copper catalyst, copper iodide or the like is preferred.

(In the formulae, $R^6$ represents a carboxyl-protecting group.) This synthetic method is a method for synthesizing the compound (C-5) of the invention by deprotecting the protecting group $R^6$ of compound (C-4) using an acid or a base etc.

This reaction is carried out by allowing compound (C-4) to react with an equivalent amount or an excess of acid or base in an inert solvent between room temperature and heating under reflux for normally 0.5 to 5 days. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, alcohols such as methanol, ethanol, 2-propanol, and butanol, N,N-dimethylformamide (DMF), N-methylpyrrolidone, dimethyl sulfoxide (DMSO), water, or a mixed solvent thereof, and the like. Acids include inorganic salts such as hydrogen chloride, hydrogen bromide, sulfuric acid, nitric acid, phosphoric acid or a solution of the acids diluted with water or organic solvents. Bases include sodium hydroxide, potassium hydroxide, lithium hydroxide, inorganic salts such as sodium carbonate, potassium carbonate, cesium carbonate, and tripotassium phosphate, metal alkoxides such as sodium ethoxide and sodium methoxide, or solutions obtained by diluting these bases with water etc., and the like.

Synthetic Method (D)
Synthesis of Compound (D-2)

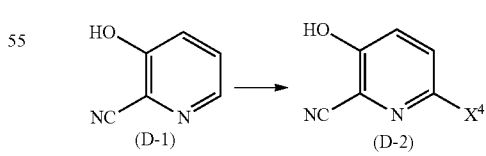

(D-1)

(D-2)

(In the formulae, $X^4$ represents a leaving group.) This synthetic method is a method for synthesizing compound (D-2) by halogenating compound (D-1). The leaving group represented by $X^4$ includes iodine, bromine, and chlorine atoms. This reaction is carried out by reacting compound (D-1) with an equivalent amount or an excess of halogenating agent in an inert solvent between 0° C. and heating under reflux for normally 0.5 hours to 3 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, ethyl acetate, water, or a mixed solvent thereof. Halogenating agents include chlorine, bromine, N-chlorosuccinimide, N-bromosuccinimide, N-iodosuccinimide, water, or a mixed solvent thereof, and the like.

Synthesis of Compound (D-4)

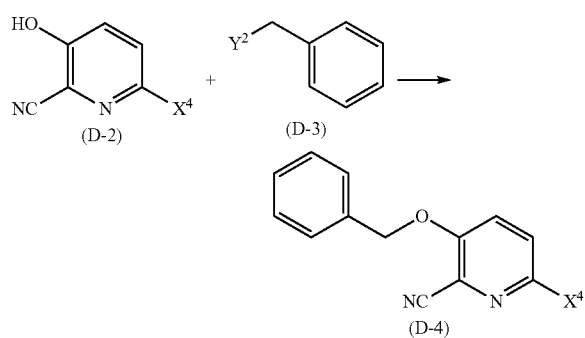

(In the formulae, $X^4$ and $Y^2$ represent a leaving groups.) This synthesis method is a method for synthesising the compound (D-4) by reacting compounds (D-2) and ((D-3). The leaving group represented by $X^4$ includes an iodine atom, a bromine atom, a chlorine atom, and the leaving group represented by $Y^2$ includes halogen atom, a methanesulfonyloxy group, a p-toluenesulfonyloxy group, a trifluoromethanesulfonyloxy group, and the like. This reaction is carried out by using equivalent amounts of compounds (D-2) and (D-3) or by using either one in excess and allowing them to react in an inert solvent in the presence of a base between room temperature and heating under reflux for normally 0.5 hours to 3 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, N,N-dimethylformamide (DMF), N-methylpyrrolidone, dimethyl sulfoxide (DMSO), pyridine, ethyl acetate or a mixed solvent thereof, and the like. Bases include inorganic salts such as sodium hydride, sodium hydride, potassium hydroxide, lithium hydroxide, sodium carbonate, potassium carbonate, cesium carbonate, metal alkoxides such as sodium ethoxide and sodium methoxide, or an organic amine base such as triethylamine, N-ethyl-N,N-diisopropylamine (DIPEA) or 1,8-diazabicyclo(5.4.0)-7-undecene (DBU), pyridine, and the like.

Synthesis of Compound (D-5)

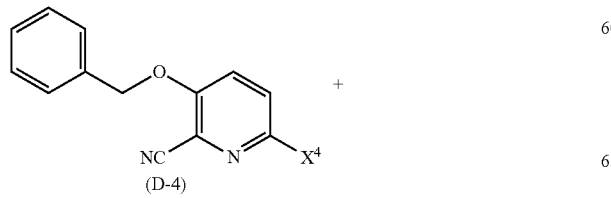

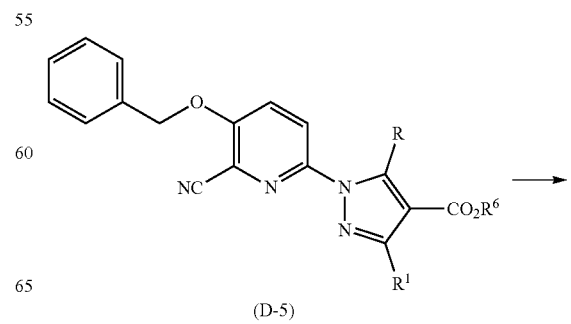

(In the formulae, $R^6$ represents a carboxyl-protecting group and $X^4$ represents a leaving group.) This reaction is a method for synthesizing compound (D-5) by coupling compounds (D-4) and (A-6). The leaving group represented by $X^4$ includes an iodine atom, a bromine atom and a chlorine atom. This reaction is carried out by using equivalent amounts of compounds (D-4) and (A-6) or by using either one in excess and allowing them to react in an inert solvent in the presence of a base, a copper catalyst, and a ligand between room temperature and heating under reflux for normally 0.5 hours to 3 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, N,N-dimethylformamide (DMF), N-methylpyrrolidone, dimethyl sulfoxide (DMSO), ethyl acetate or a mixed solvent thereof, and the like. Bases include inorganic salts such as sodium hydride, sodium hydroxide, potassium hydroxide, lithium hydroxide, sodium carbonate, potassium carbonate, cesium carbonate, metal alkoxides such as sodium ethoxide and sodium methoxide, or an organic amine base such as triethylamine, N-ethyl-N,N-diisopropylamine (DIPEA) or 1,8-diazabicyclo(5.4.0)-7-undecene (DBU), and the like. Copper catalysts include copper chloride, copper bromide, copper iodide, copper oxide, and the like. Ligands include proline, trans-N,N'-dimethylcyclohexane-1,2-diamine, N,N-dimethylaminoacetic acid, 1,10-phenanthroline, and the like.

Synthesis of Compound (D-6)

-continued

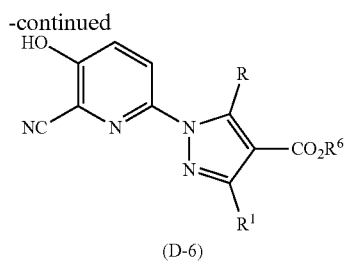

(D-6)

(In the formulae, $R^6$ represents a carboxyl-protecting group.) This synthetic method is a method for synthesizing compound (D-6) by debenzylation of compound (D-5). This reaction is carried out by allowing compound (D-5) to react in an inert solvent in the presence of a palladium catalyst under a hydrogen gas atmosphere between room temperature and heating under reflux for normally 0.5 to 2 days. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, alcohols such as methanol, ethanol, 2-propanol, and butanol, N,N-dimethylformamide (DMF), N-methylpyrrolidone, dimethyl sulfoxide (DMSO), ethyl acetate or a mixed solvent thereof, and the like. As the palladium catalyst, palladium-carbon, palladium hydroxide, palladium black, or the like is preferred.

Synthesis of Compound (D-8)

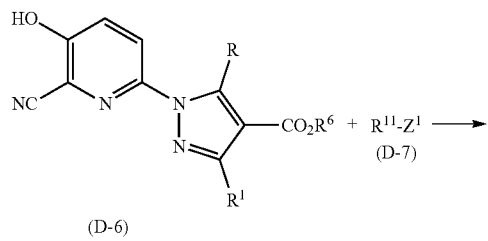

(D-6)                              (D-7)

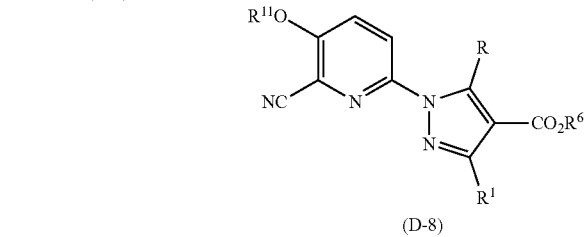

(D-8)

(In the formulae, $R^6$ represents a carboxyl-protecting group. $R^{11}$ represents an unsubstituted or substituted $C_{1-9}$ alkylsulfonyl group or an unsubstituted or substituted phenylsulfonyl group. $Z^1$ represents a leaving group.) This synthetic method is a method for synthesizing compound (D-8) by sulfonyl-esterification of the phenolic hydroxyl group of compound (D-6). Sulfonyl groups represented by $R^{11}$ include methanesulfonyl, trifluoromethanesulfonyl, p-toluenesulfonyl groups, and the like. The leaving group represented by $Z^1$ includes a halogen atom, a methanesulfonyloxy group, a p-toluenesulfonyloxy group, a trifluoromethanesulfonyloxy group, and the like. This reaction is carried out by using equivalent amounts of compounds (D-6) and (D-7) or by using either one in excess and allowing them to react in an inert solvent in the presence of a base between 0° C. and heating under reflux for normally 0.5 hours to 2 days. It is preferred that this reaction is performed under an inert gas atmosphere such as nitrogen. Solvents here include, though not particularly limited to, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, N,N-dimethylformamide (DMF), N-methylpyrrolidone, dimethyl sulfoxide (DMSO), pyridine, ethyl acetate or a mixed solvent thereof, and the like. It is preferred that this reaction is performed under an inert gas atmosphere. Bases include inorganic salts such as sodium hydride, sodium hydroxide, potassium hydroxide, lithium hydroxide, sodium carbonate, potassium carbonate, cesium carbonate, sodium hydrogen carbonate, or an organic amine base such as triethylamine, N-ethyl-N, N-diisopropylamine (DIPEA) or 1,8-diazabicyclo(5.4.0)-7-undecene (DBU), pyridine, and the like.

Synthesis of Compound (D-9)

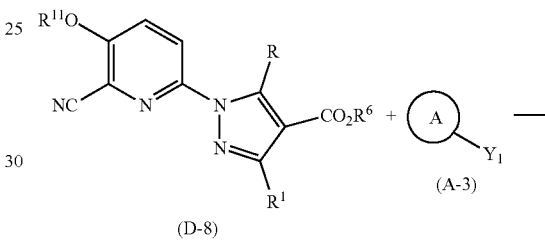

(D-8)                              (A-3)

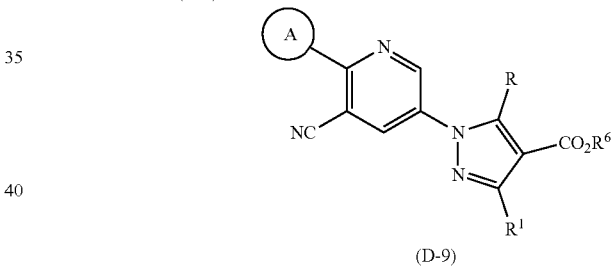

(D-9)

(In the formulae, $R^6$ represents a carboxyl-protecting group. $R^{11}$ represents an unsubstituted or substituted $C_{1-9}$ alkylsulfonyl group or an unsubstituted or substituted phenylsulfonyl group. $Y^1$ represents $-B(OH)_2$ or $-B(OR^7)OR^8$, wherein $R^7$ and $R^8$ are the same or different from each other and represent $C_{1-6}$ alkyl groups, or $R^7$ and $R^8$ are taken together to represent a $C_{1-6}$ alkylene group.) This reaction is a method for synthesizing compound (D-9) by coupling compounds (D-8) and (A-3). The sulfonyl group represented by $R^{11}$ includes a methanesulfonyl group, a trifluoromethanesulfonyl group, a p-toluenesulfonyl group, and the like. This reaction is carried out by using equivalent amounts of compounds (D-8) and (A-3) or by using either one in excess and allowing them to react in an inert solvent in the presence of a base and a palladium catalyst between room temperature and heating under reflux for normally 0.5 to 2 days. It is preferred that this reaction is performed under an inert gas atmosphere such as nitrogen. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, alcohols such as methanol, ethanol, 2-propanol, and butanol, N,N-dimethylformamide (DMF), N-methylpyrrolidone, dimethyl sulfoxide (DMSO), water, or a mixed solvent thereof, and the like. Bases include sodium hydroxide, potassium hydroxide, lithium hydroxide, inorganic salts such as sodium carbonate, potassium carbonate, cesium carbonate, and potassium phosphate, metal alkoxides such as sodium ethoxide and sodium methoxide, or solutions obtained by diluting these bases with water etc., and the like. As the palladium catalyst, tetrakis(triphenylphosphine)palladium, dichlorobis(triphenylphosphine)palladium, palladium chloride-1,1'-bis(diphenylphosphino)ferrocene, or the like is preferred.

Synthesis of Compound (D-10)

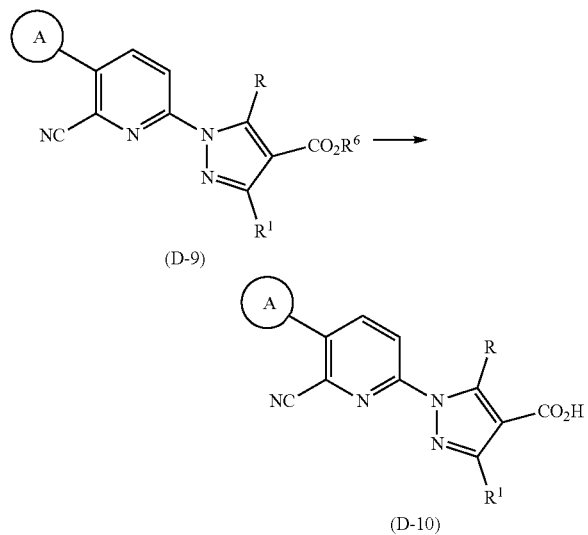

(In the formulae, $R^6$ represents a carboxyl-protecting group.) This synthetic method is a method for synthesizing the inventive compound (D-10) of the invention by deprotecting the protecting group $R^6$ of compound (D-9) using an acid or a base etc. This reaction is carried out by allowing compound (D-9) to react with an equivalent amount or an excess of acid or base in an inert solvent between room temperature and heating under reflux for normally 0.5 to 5 days. Solvents here include, though not particularly limited, for example, aromatic hydrocarbons such as benzene, toluene, and xylene, ethers such as diethyl ether, tetrahydrofuran (THF), 1,4-dioxane, 1,2-dimethoxyethane, and 1,2-diethoxyethane, halogenated hydrocarbons such as dichloromethane, 1,2-dichloroethane, and chloroform, alcohols such as methanol, ethanol, 2-propanol, and butanol, N,N-dimethylformamide (DMF), N-methylpyrrolidone, dimethyl sulfoxide (DMSO), water, or a mixed solvent thereof, and the like. Acids include inorganic salts such as hydrogen chloride, hydrogen bromide, sulfuric acid, nitric acid, phosphoric acid or a solution of the acids diluted with water or organic solvents. Bases include sodium hydroxide, potassium hydroxide, lithium hydroxide, inorganic salts such as sodium carbonate and potassium carbonate, metal alkoxides such as sodium ethoxide and sodium methoxide, or solutions obtained by diluting these bases with water etc., and the like.

Hereinafter, salts described as preferred compounds and pharmaceutically acceptable salts thereof among compounds represented by the foregoing formula (I) include, though not particularly limited as long as they are pharmaceutically acceptable salts, for example, salts with inorganic acids such as hydrogen chloride, hydrogen bromide, sulfuric acid, nitric acid, phosphoric acid, and carbonic acid; salts with organic acids such as maleic acid, fumaric acid, citric acid, malic acid, tartaric acid, lactic acid, succinic acid, benzoic acid, oxalic acid, methanesulfonic acid, benzenesulfonic acid, p-toluenesulfonic acid, acetic acid, trifluoroacetic acid, and formic acid; salts with amino acids such as glycine, lysine, arginine, histidine, ornithine, glutamic acid, and aspartic acid; salts with alkali metals such as sodium, potassium, and lithium; salts with alkaline earth metals such as calcium and magnesium; salts with metals such as aluminum, zinc, and iron, salts with organic oniums such as tetramethylammonium, choline, etc.; and salts with organic bases such as ammonia, propanediamine, pyrrolidine, piperidine, pyridine, ethanolamine, N,N-dimethylethanolamine, 4-hydroxypiperidine, t-octylamine, dibenzylamine, morpholine, glucosamine, phenylglycyl alkyl ester, ethylenediamine, N-methylglucamine, guanidine, diethylamine, triethylamine, dicyclohexylamine, N,N'-dibenzylethylenediamine, chloroprocaine, procaine, diethanolamine, N-benzylphenylamine, piperazine, and tris(hydroxymethyl)aminomethane.

Furthermore, the compounds represented by formula (I) and salts thereof encompass various hydrates and solvates.

The foregoing various pharmaceutically acceptable salts of the compounds represented by formula (I) can be appropriately produced based on the ordinary skill in the art.

The compounds of the present invention also include the stereoisomers, the racemates, and all possible optically active forms of the compounds represented by formula (I).

The compounds represented by formula (I) of the present invention and pharmaceutically acceptable salts thereof have particularly excellent xanthine oxidase inhibitory activity. In view of their excellent xanthine oxidase inhibitory activity, the compounds represented by formula (I) of the present invention and pharmaceutically acceptable salts thereof will be useful as xanthine oxidase inhibitors.

The compounds represented by formula (I) of the present invention and pharmaceutically acceptable salts thereof can be used as pharmaceuticals for the treatment or prophylaxis of diseases associated with xanthine oxidase, such as gout, hyperuricemia, tumor lysis syndrome, urinary calculus, hypertension, dyslipidemia, diabetes, cardiovascular diseases such as arteriosclerosis or heart failure, renal diseases such as diabetic nephropathy, respiratory diseases such as chronic obstructive pulmonary disease, inflammatory bowel diseases, or autoimmune diseases, to which they are clinically applicable as xanthine oxidase inhibitors.

The compounds represented by the foregoing formula (I) and pharmaceutically acceptable salts thereof can be made into a pharmaceutical composition together with a pharmaceutically acceptable carrier and/or diluent. The pharmaceutical composition can be formed into various dosage forms to be administered orally or parenterally. Parenteral administration includes, for example, intravenous, subcutaneous, intramuscular, transdermal, or rectal administration.

Formulations containing one or more than one of the compounds represented by formula (I) of the present invention or salts thereof as an active ingredient are prepared by using carriers, excipients, and other additives that are commonly used in drug formulation. Carriers and excipients for drug formulation may be solid or liquid and include, for example, lactose, magnesium stearate, starch, talc, gelatin, agar, pectin, *acacia* gum, olive oil, sesame oil, cacao butter, ethylene glycol, etc. and other commonly used ones. Administration may be in the form of oral administration via tablets, pills, capsules, granules, powders, liquid preparations, etc. or in the form of parenteral administration via injections such as intravenous and intramuscular injections, suppositories, transdermal preparations, etc.

In general, a dosage of the compound represented by formula (I) of the present invention or a pharmaceutically acceptable salt thereof in the range of 0.01 to 1000 mg can be administered per adult per day, at one time or divided into several times, though the dosage varies depending on the type of disease, the route of administration, the symptoms, age, sex, and body weight of the patient, etc. However, since the dosage varies under various conditions, there are some cases where an amount lower than the above described dosage is sufficient and others where a dosage exceeding the above described range is needed.

EXAMPLES

The present invention will be described below based on specific examples; however, it is not limited to these examples.

Structures of isolated novel compounds were confirmed by $^1$H NMR and/or mass spectrometry using a single quadrupole instrumentation equipped with an electrospray source, or other appropriate analytical methods.

For compounds for which $^1$H NMR spectra (400 MHz, DMSO-$d_6$ or CDCl$_3$) were measured, their chemical shifts (δ:ppm) and coupling constants (J:Hz) are shown. As for the results of mass spectrometry, M$^+$+H, i.e., a measured value observed as a value of compound's molecular mass (M) to which a proton (H$^+$) is added, is shown. It should be noted that the following abbreviations respectively stand for the following. s=singlet, d=doublet, t=triplet, q=quartet, brs=broad singlet, m=multiplet.

On the compounds synthesized according to the methods of the following examples, further analyses were performed by high-performance liquid chromatography (HPLC) analysis and by mass spectrometry using Time Of Flight-Mass Spectroscopy (TOF-MS) equipped with an electrospray ion source.

The retention time (in min) of a compound in HPLC analysis under the following analytical conditions is shown as HPLC retention time.
Measurement Conditions of HPLC
Measurement device: Hewlett-Packard 1100HPLC
Column: Imtakt Cadenza CD-C18 100 mm×4.6 mm 3 μm
UV: PDA detection (254 nm)
Column temperature: 40 degrees centigrade
Gradient conditions:
  Solvent: A: H$_2$O/acetonitrile=95/5
  0.05% TFA (trifluoroacetic acid)
  B: H$_2$O/acetonitrile=5/95
  0.05% TFA (trifluoroacetic acid)
  Flow rate: 1.0 mL/min
  Gradient:
  0 to 1 min, Solvent B: 2%, Solvent A: 98%
  1 to 14 min, Solvent B: 2% to 100%, Solvent A: 98% to 0%
  14 to 17 min, Solvent B: 100%, Solvent A: 0%
  17 to 19 min, Solvent B: 100% to 2%, Solvent A: 0% to 98%

As for the results of mass spectrometry, together with the value of "M$^+$+H" observed by the device and analytical conditions given below (Obs. Mass: i.e., an observed value of compound's molecular mass (M) to which a proton (H$^+$) is added) and the calculated value of "M$^+$+H" (Pred. Mass), the compositional formula (Formula) calculated from the observed value of "M$^+$+H" is also shown.
Measurement Conditions of TOF-MS
Mass spectrometer: Shimadzu LCMS-IT-TOF
LC: Prominence
Column: Phenomenex Synergi Hydro-RP 4.0 mm×20 mm 2.5 μm
UV: PDA detection (254 nm)
Flow rate: 0.6 mL/min
Column temperature: 40 degrees centigrade
Detection voltage: 1.63 kV
Gradient conditions:
  Solvent: A: H$_2$O/acetonitrile=95/5
  0.1% HCOOH
  B: H$_2$O/acetonitrile=5/95
  0.1% HCOOH
  Flow rate: 0.5 mL/min
  Gradient:
  0 to 0.2 min, Solvent B: 2%, Solvent A: 98%
  0.2 to 2.5 min, Solvent B: 2% to 100%, Solvent A: 98% to 0%
  2.5 to 3.8 min, Solvent B: 100%, Solvent A: 0%
  3.8 to 4.0 min, Solvent B: 100% to 2%, Solvent A: 0% to 98%
  4.0 to 5.0 min, Solvent B: 2%, Solvent A: 98%

Reference Example

Synthesis of 5-bromo-2-chloropyridine-4-carbaldehyde (reference example compound)

After a solution prepared by dissolving 10.6 mL of diisopropylamine in 100 mL of THF was cooled to −78° C., 22.7 mL of n-butyllithium was added thereto slowly dropwise. After the reaction solution was stirred for 1 hour, a solution obtained by dissolving 9.7 g of 5-bromo-2-chloropyridine in 50 mL of THF was added slowly dropwise, and the reaction solution was stirred for another hour. Afterwards, 10 mL of N,N-dimethylformamide (DMF) was added dropwise. After this mixed solution was stirred for 1 hour at −78° C., 30 mL of 2 M hydrochloric acid was added, and temperature was raised slowly to room temperature, followed by stirring for 30 minutes at room temperature. Water was added to the reaction mixture, which was then extracted with ethyl acetate. The organic layer was washed with brine, then dried and concentrated in vacuo. 10 mL of dichloromethane was added to the residue, purification was carried out by a conventional method to obtain 3.23 g of 5-bromo-2-chloropyridine-4-carbaldehyde. In addition, after the filtrate was concentrated in vacuo, the residue was purified by silica gel chromatography (hexane:ethyl acetate=9:1) to give 6.34 g of 5-bromo-2-chloropyridine-4-carbaldehyde.
$^1$H-NMR (400 MHz, CDCl$_3$) δ (ppm): 7.72 (1H, s), 8.68 (1H, s), 10.30 (1H, s).

Example 1

Synthesis of 1-(4-cyano-5-phenylpyridin-2-yl)-1H-pyrazole-4-carboxylic acid (compound No. 1) (synthetic method (A))

(1) To a suspension prepared by adding 8.80 g of 5-bromo-2-chloropyridine-4-carbaldehyde, 5.36 g of phenylboronic acid, and 11.06 g of potassium carbonate in 100 mL of a mixed solution of 4-dioxane/water=4/1, 924 mg of tetrakis(triphenylphosphine)palladium was added, and the resultant reaction mixture was heated at 80° C. for 5 hours under a nitrogen atmosphere. Water was added to the reaction mixture, which was then extracted with ethyl acetate. The organic layer was washed with brine, then dried and concentrated in vacuo to give 10.80 g of 2-chloro-5-phenylpyridine-4-carbaldehyde.

$^1$H-NMR (400 MHz, CDCl$_3$) δ (ppm): 7.3-7.42 (2H, m), 7.50-7.60 (3H, m), 7.81 (1H, d, J=0.6 Hz), 8.61 (1H, d, J=0.6 Hz), 9.99 (1H, s).

ESI/MS m/e: 218.0, 220.0 (M$^+$+H, C$_{12}$H$_8$ClNO).

(2) To a suspension prepared by adding 10.80 g of 2-chloro-5-phenylpyridine-4-carbaldehyde, 5.56 g of hydroxylamine monohydrochloride, and 5.44 g of sodium formate to 100 mL of formic acid, 12.2 g of acetic anhydride was added, and the resultant reaction mixture was heated at 100° C. for 2 hours under a nitrogen atmosphere. 100 mL of water was added and purification was conducted by conventional means to give 6.34 g of 2-chloro-5-phenylpyridine-4-carbonitrile.

$^1$H-NMR (400 MHz, CDCl$_3$) δ (ppm): 7.27 (1H, s), 7.5-7.6 (5H, m), 7.67 (1H, s), 8.63 (1H, s).

ESI/MS m/e: 215.0, 217.0 (M$^+$+H, C$_{12}$H$_7$ClN$_2$).

(3) A reaction mixture prepared by suspending 3.22 g of 2-chloro-5-phenylpyridine-4-carbonitrile, 2.31 g of ethyl 1H-pyrazole-4-carboxylate, and 3.11 g of potassium carbonate in 40 mL of dimethyl sulfoxide was heated at 120° C. for 2.5 hours under a nitrogen atmosphere. 50 mL of water was added and purification was conducted by conventional means to give 3.97 g of ethyl 1-(4-cyano-5-phenylpyridin-2-yl)-1H-pyrazole-4-carboxylate.

$^1$H-NMR (400 MHz, DMSO d$_6$) δ (ppm): 1.31 (3H, t, J=8.0 Hz), 4.28 (2H, q, J=8.0 Hz), 7.55-7.62 (3H, m), 7.70-7.72 (2H, m), 8.32 (1H, s), 8.43 (1H, s), 8.86 (1H, s), 9.05 (1H, s) ESI/MS m/e: 319.1 (M$^+$+H, C$_{18}$H$_{14}$N$_4$O$_2$).

(4) To a solution prepared by dissolving 3.97 g of ethyl 1-(4-cyano-5-phenylpyridin-2-yl)-1H-pyrazole-4-carboxylate in 30 mL of a mixed solution of tetrahydrofuran/methanol=1/1, 30 mL of 6 M hydrochloric acid was added, and the resultant reaction mixture was heated at 80° C. for 48 hours. Purification was conducted by conventional means to give 3.71 g of 1-(4-cyano-5-phenylpyridin-2-yl)-1H-pyrazole-4-carboxylic acid.

$^1$H-NMR (400 MHz, DMSO d$_6$) δ (ppm): 7.54-7.62 (3H, m), 7.70-7.72 (2H, m), 8.26 (1H, s), 8.41 (1H, s), 8.85 (1H, s), 8.98 (1H, s), 12.91 (1H, s).

HPLC Retention Time: 10.48 min.
Obs Mass (M$^+$+H): 291.0880
Pred Mass (M$^+$+H): 291.0877
Formula (M): C$_{16}$H$_{10}$N$_4$O$_2$ Examples 2 to 70

Using the above reference example compound as the starting material, compound Nos. 2 to 70 were synthesized in the same manner as in Example 1.

| Ex. | Comp. No. | HPLC Retention Time | Obs Mass (M$^+$ + H) | Pred Mass (M$^+$ + H) | Formula (M) | 1H NMR |
|---|---|---|---|---|---|---|
| 2 | 2 | 10.53 | 321.0975 | 321.0982 | C17H12N4O3 | |
| 3 | 3 | 11.21 | 335.1136 | 335.1139 | C18H14N4O3 | |
| 4 | 4 | 10.92 | 305.1021 | 305.1033 | C17H12N4O2 | |
| 5 | 5 | 10.43 | 309.0772 | 309.0782 | C16H9N4O2F | 400 MHz (DMSO d6) 7.41-7.50 (1H, m), 7.54-7.63 (2H, m), 7.72 (1H, d, J = 4.0 Hz), 8.26 (1H, s), 8.49 (1H, s), 8.79 (1H, s), 9.00 (1H, s), 12.93 (1H, brs). |
| 6 | 6 | 10.89 | 325.0486 | 325.0487 | C16H9N4O2Cl | 400 MHz (DMSO d6) 7.46-7.50 (1H, m), 7.54-7.63 (2H, m), 7.72 (1H, d, J = 4.0 Hz), 8.26 (1H, s), 8.49 (1H, s), 8.79 (1H, s), 9.00 (1H, s), 12.93 (1H, brs). |
| 7 | 7 | 10.52 | 321.0971 | 321.0982 | C17H12N4O3 | 400 MHz (DMSO d6) 3.80 (3H, s), 7.14 (1H, t, J = 8.0 Hz, 8.0 Hz), 7.24 (1H, d, J = 8.0 Hz), 7.43 (1H, d, 8.0 Hz), 7.53 (1H, t, J = 8.0 Hz), 8.24 (1H, s), 8.38 (1H, s), 8.72 (1H, s), 8.97 (1H, s), 12.89 (1H, s). |
| 8 | 8 | 11.03 | 359.0745 | 359.0750 | C17H9N4O2F3 | |
| 9 | 9 | 11.31 | 375.0701 | 375.0700 | C17H9N4O3F3 | |
| 10 | 10 | 11.25 | 305.1027 | 305.1033 | C17H12N4O2 | 400 MHz (DMSO d6) 2.31 (3H, s), 7.36-7.38 (1H, m), 7.47-7.50 (3H, m), 8.24 (1H, s), 8.38 (1H, s), 8.82 (1H, s), 8.96 (1H, s), 12.93 (1H, brs). |
| 11 | 11 | 10.61 | 309.0778 | 309.0782 | C16H9N4O2F | 400 MHz (DMSO d6) 7.39-7.44 (1H, m), 7.55-7.57 (1H, m), 7.61-7.67 (2H, m), 8.25 (1H, s), 8.43 (1H, s), 8.87 (1H, s), 8.97 (1H, s), 12.93 (1H, brs). |
| 12 | 12 | 11.30 | 325.0474 | 325.0487 | C16H9N4O2Cl | 400 MHz (DMSO d6) 7.61-7.68 (3H, m), 7.81 (1H, s), 8.24 (1H, s), 8.40 (1H, s), 8.85 (1H, s), 8.95 (1H, s), 12.91 (1H, s). |
| 13 | 13 | 10.59 | 321.0979 | 321.0982 | C17H12N4O3 | 400 MHz (DMSO d6) 3.84 (3H, s), 7.11-7.14 (1H, m), 7.25-7.27 (2H, m), 7.50 (1H, t, J = 8.0 Hz, 8.0 Hz), 8.24 (1H, s), 8.39 (1H, s), 8.85 (1H, s), 8.96 (1H, s), 12.90 (1H, brs). |
| 14 | 14 | 11.29 | 305.1030 | 305.1033 | C17H12N4O2 | 400 MHz (DMSO d6) 2.40 (3H, s), 7.40 (2H, d, J = 8.0 Hz), 7.60 (2H, d, J = 8.0 Hz), 8.24 (1H, s), 8.38 (1H, s), 8.82 (1H, s), 8.96 (1H, s), 12.92 (1H, brs). |

Ex. denotes Example and Comp. No. denotes Compound Number in the above table including all the following tables.

| Ex. | Comp. No. | HPLC Retention Time | Obs Mass (M$^+$ + H) | Pred Mass (M$^+$ + H) | Formula (M) | 1H NMR |
|---|---|---|---|---|---|---|
| 15 | 15 | 11.41 | 325.0485 | 325.0487 | C16H9N4O2Cl | 400 MHz (DMSO d6) 7.67 (2H, d, J = 8.0 Hz), 7.74 (2H, d, J = 8.0 Hz), 8.25 (1H, s), 8.42 (1H, s), 8.85 (1H, s), 8.97 (1H, s), 12.92 (1H, brs). |
| 16 | 16 | 8.64 | 307.0816 | 308.0826 | C16H10N4O3 | |
| 17 | 17 | 11.26 | 353.1047 | 353.1044 | C18H13N4O3F | 400 MHz (DMSO d6) 1.23 (3H, t, J = 8.0 Hz), 4.07-4.15 (2H, m), 7.03 (1H, t, J = 8.0 Hz), 7.09 (1H, d, J = 8.0 Hz), 7.52-7.58 (1H, m), 8.25 (1H, s), 8.47 (1H, s), 8.78 (1H, s), 8.98 (1H, s), 12.95 (1H, brs). |
| 18 | 18 | 10.61 | 339.0877 | 339.0888 | C17H11N4O3F | 400 MHz (DMSO d6) 3.81 (3H, s), 7.06 (1H, t, J = 8.0 Hz), 7.11 (1H, d, J = 8.0 Hz), 7.55-7.61 (1H, m), 8.25 (1H, s), 8.47 (1H, s), 8.77 (1H, s), 8.98 (1H, s), 12.95 (1H, brs). |
| 19 | 19 | 10.33 | 339.0880 | 339.0888 | C17H11N4O3F | 400 MHz (DMSO d6) 3.92 (3H, s), 7.14-7.17 (1H, m), 7.32-7.41 (2H, m), 8.25 (1H, s), 8.47 (1H, s), 8.82 (1H, s), 8.97 (1H, s), 12.95 (1H, brs). |
| 20 | 20 | 10.64 | 327.0682 | 327.0688 | C16H8N4O2F2 | |
| 21 | 21 | 10.25 | 297.0435 | 297.0441 | C14H8N4O2S | 400 MHz (DMSO d6) 7.61-7.62 (1H, m), 7.81-7.83 (1H, m), 8.13-8.14 (1H, m), 8.23 (1H, s), 8.36 (1H, s), 8.94 (2H, s), 12.95 (1H, brs). |
| 22 | 22 | 10.77 | 311.0594 | 311.0597 | C15H10N4O2S | |
| 23 | 23 | 9.76 | 281.0658 | 281.0669 | C14H8N4O3 | 400 MHz (DMSO d6) 7.13-7.14 (1H, m), 7.93 (1H, t, J = 4.0 Hz), 8.22 (1H, s), 8.33 (1H, s), 8.39 (1H, m), 8.93 (1H, s), 8.96 (1H, s), 12.88 (1H, brs). |
| 24 | 24 | 6.46 | 322.0921 | 322.0935 | C16H11N5O3 | |
| 25 | 25 | 6.25 | 292.0813 | 292.0829 | C15H9N5O2 | |
| 26 | 26 | 11.17 | 305.1024 | 305.1033 | C17H12N4O2 | |
| 27 | 27 | 12.78 | 333.1335 | 333.1346 | C19H16N4O2 | 400 MHz (DMSO d6) 1.15 (6H, d, J = 8.0 Hz), 3.55 (1H, q, J = 8.0 Hz), 7.54-7.62 (3H, m), 7.69-7.71 (2H, m), 8.32 (1H, s), 8.82 (1H, s), 8.87 (1H, s), 12.74 (1H, s). |
| 28 | 28 | 11.33 | 319.1180 | 319.1190 | C18H14N4O2 | |
| 29 | 29 | 10.60 | 309.0771 | 309.0782 | C16H9N4O2F | |
| 30 | 30 | 11.33 | 333.0993 | 333.0993 | C18H14N4O3 | |
| 31 | 31 | 12.17 | 349.1291 | 349.1295 | C19H16N4O3 | |
| 32 | 32 | 10.68 | 327.0678 | 327.0688 | C16H8N4O2F2 | 400 MHz (DMSO d6) 7.34-7.38 (1H, m), 7.54-7.60 (1H, m), 7.72-7.78 (1H, m), 8.26 (1H, s), 8.48 (1H, s), 8.83 (1H, s), 8.99 (1H, s), 12.93 (1H, s). |
| 33 | 33 | 11.22 | 323.0928 | 323.0939 | C17H11N4O2F | 400 MHz (DMSO d6) 2.42 (3H, s), 7.24 (1H, d, J = 8.0 Hz), 7.30 (1H, d, J = 8.0 Hz), 7.53 (1H, t, J = 8.0 Hz), 8.25 (1H, s), 8.45 (1H, s), 8.80 (1H, s), 8.98 (1H, s), 12.90 (1H, s). |
| 34 | 34 | 11.18 | 323.0923 | 323.0939 | C17H11N4O2F | 400 MHz (DMSO d6) 2.37 (3H, s), 7.32-7.36 (1H, m), 7.40-7.44 (2H, m), 8.25 (1H, s), 8.46 (1H, s), 8.81 (1H, s), 8.98 (1H, s), 12.92 (1H, s). |
| 35 | 35 | 10.56 | 327.0691 | 327.0688 | C16H8N4O2F2 | 400 MHz (DMSO d6) 7.47-7.58 (2H, m), 7.61-7.66 (1H, m), 8.27 (1H, s), 8.50 (1H, s), 8.87 (1H, s), 8.99 (1H, s), 12.92 (1H, brs). |
| 36 | 36 | 11.21 | 323.0934 | 323.0939 | C17H11N4O2F | 400 MHz (DMSO d6) 2.33 (3H, s), 7.29-7.33 (1H, m), 7.43-7.52 (2H, m), 8.25 (1H, s), 8.46 (1H, s), 8.81 (1H, s), 8.98 (1H, s), 12.91 (1H, s). |
| 37 | 37 | 11.39 | 323.0925 | 323.0939 | C17H11N4O2F | 400 MHz (DMSO d6) 2.33 (3H, s), 7.38 (1H, dd, J = 8.0 Hz, 12.0 Hz), 7.56-7.60 (1H, m), 7.64 (1H, d, J = 12.0 Hz), 8.25 (1H, s), 8.40 (1H, s), 8.83 (1H, s), 8.97 (1H, s), 12.92 (1H, s). |
| 38 | 38 | 11.52 | 319.1190 | 319.1190 | C18H14N4O2 | 400 MHz (DMSO d6) 2.07 (3H, s), 2.33 (3H, s), 7.17 (1H, d, J = 8.0 Hz), 7.25 (1H, t, J = 8.0 Hz), 7.35 (1H, d, J = 8.0 Hz), 8.25 (1H, s), 8.42 (1H, s), 8.67 (1H, s), 8.98 (1H, s), 12.91 (1H, s). |

-continued

| Ex. | Comp. No. | HPLC Retention Time | Obs Mass (M⁺ + H) | Pred Mass (M⁺ + H) | Formula (M) | 1H NMR |
|---|---|---|---|---|---|---|
| 39 | 39 | 11.41 | 323.0932 | 323.0939 | C17H11N4O2F | 400 MHz (DMSO d6) 2.32 (3H, s), 7.44-7.56 (3H, m), 8.25 (1H, s), 8.40 (1H, s), 8.84 (1H, s), 8.96 (1H, s), 12.92 (1H, s). |
| 40 | 40 | 11.42 | 341.0243 | 341.0247 | C16H8N4O2FCl | 400 MHz (DMSO d6) 7.67 (1H, dd, J = 8.0 Hz, 12.0 Hz), 7.73-7.77 (1H, m), 8.01 (1H, dd, J = 4.0 Hz, 8.0 Hz), 8.25 (1H, s), 8.42 (1H, s), 8.87 (1H, s), 8.97 (1H, s), 12.91 (1H, brs). |
| 41 | 41 | 11.23 | 343.0403 | 343.0393 | C16H8N4O2FCl | |
| 42 | 42 | 8.41 | 335.0766 | 335.0775 | C17H10N4O4 | 400 MHz (DMSO d6) 7.85 (2H, d, J = 8.0 Hz), 8.12 (2H, d, J = 8.0 Hz), 8.26 (1H, s), 8.44 (1H, s), 8.89 (1H, s), 8.98 (1H, s), 13.07 (2H, brs) |
| 43 | 43 | 11.62 | 359.0743 | 359.0750 | C17H9N4O2F3 | 400 MHz (DMSO d6) 7.93-7.99 (4H, m), 8.26 (1H, s), 8.45 (1H, s), 8.89 (1H, s), 8.98 (1H, s), 12.90 (1H, brs). |
| 44 | 44 | 11.88 | 375.0697 | 375.0700 | C17H9N4O3F3 | 400 MHz (DMSO d6) 7.61 (2H, d, J = 8.0 Hz), 8.85 (2H, d, J = 8.0 Hz), 8.26 (1H, s), 8.43 (1H, s), 8.88 (1H, s), 8.98 (1H, s), 12.90 (1H, brs). |
| 45 | 45 | 11.48 | 359.0745 | 359.0750 | C17H9N4O2F3 | 400 MHz (DMSO d6) 7.84 (1H, t, J = 8.0 Hz), 7.93 (1H, d, J = 8.0 Hz), 8.03 (1H, d, J = 8.0 Hz), 8.11 (1H, s), 8.26 (1H, s), 8.44 (1H, s), 8.92 (1H, s), 8.98 (1H, s), 12.94 (1H, brs). |
| 46 | 46 | 10.83 | 357.0798 | 357.0794 | C17H10N4O3F2 | 400 MHz (DMSO d6) 7.35 (1H, t, J = 72 Hz), 7.37 (1H, m), 7.55-7.68 (3H, m), 8.26 (1H, s), 8.43 (1H, s), 8.88 (1H, s), 8.98 (1H, s), 12.92 (1H, s). |
| 47 | 47 | 12.55 | 333.1340 | 333.1346 | C19H16N4O2 | 400 MHz (DMSO d6) 1.26 (6H, d, J = 8.0 Hz), 2.99 (1H, q, J = 8.0 Hz), 7.47 (2H, d, J = 8.0 Hz), 7.63 (2H, d, J = 8.0 Hz), 8.24 (1H, s), 8.39 (1H, s), 8.83 (1H, s), 8.97 (1H, s), 12.90 (1H, brs). |
| 48 | 48 | 12.50 | 333.1341 | 333.1346 | C19H16N4O2 | 400 MHz (DMSO d6) 1.26 (6H, d, J = 8.0 Hz), 3.00 (1H, q, J = 8.0 Hz), 7.41-7.45 (1H, m), 7.50-7.52 (2H, m), 7.75 (1H, s), 8.25 (1H, s), 8.39 (1H, s), 8.86 (1H, s), 8.98 (1H, s), 12.91 (1H, brs).. |
| 49 | 49 | 11.01 | 323.0934 | 323.0939 | C17H11N4O2F | 400 MHz (DMSO d6) 2.20 (3H, s), 7.22 (1H, td, J = 4.0 Hz, 8.0 Hz), 7.31 (1H, dd, J = 4.0 Hz 12.0 Hz), 7.42 (1H, dd, J = 8.0 Hz, 12.0 Hz), 8.24 (1H, s), 8.43 (1H, s), 8.71 (1H, s), 8.97 (1H, s), 12.91 (1H, brs). |
| 50 | 50 | 10.74 | 339.0872 | 339.0888 | C17H11N4O3F | 400 MHz (DMSO d6) 3.82 (3H, s), 6.97-7.01 (1H, m), 7.17-7.20 (1H, m), 7.47-7.51 (1H, m), 8.24 (1H, s), 8.39 (1H, s), 8.71 (1H, s), 8.96 (1H, s), 12.90 (1H, s). |
| 51 | 51 | 12.19 | 339.0629 | 339.0643 | C17H11N4O2Cl | 400 MHz (DMSO d6) 2.42 (3H, s), 7.54-7.57 (1H, m), 7.63-7.65 (1H, m), 7.69-7.70 (1H, m), 8.24 (1H, s), 8.40 (1H, s), 8.83 (1H, s), 8.96 (1H, s), 12.90 (1H, brs). |
| 52 | 52 | 11.89 | 349.1290 | 349.1295 | C19H16N4O3 | |
| 53 | 53 | 13.00 | 347.1495 | 347.1503 | C20H18N4O2 | |
| 54 | 54 | 12.55 | 383.1141 | 383.1139 | C22H14N4O3 | 400 MHz (DMSO d6) 7.12-7.24 (5H, m), 7.46 (2H, dd, J = 8.0 Hz), 7.72 (2H, d, J = 8.0 Hz), 8.24 (1H, s), 8.39 (1H, s), 8.84 (1H, s), 8.96 (1H, s). |
| 55 | 55 | 10.31 | 335.1135 | 335.1139 | C18H14N4O3 | |
| 56 | 56 | 12.92 | 363.1446 | 363.1452 | C20H18N4O3 | |
| 57 | 57 | 11.91 | 341.1030 | 341.1033 | C20H12N4O2 | |
| 58 | 58 | 5.93 | 322.0920 | 322.0935 | C16H11N5O3 | |
| 59 | 59 | 6.32 | 335.1243 | 335.1251 | C17H14N6O2 | |
| 60 | 60 | 8.63 | 310.0723 | 310.0735 | C15H8N5O2F | 400 MHz (DMSO d6) 8.20-8.24 (1H, m), 8.27 (1H, s), 8.50 (1H, s), 8.79-8.81 (2H, m), 8.95 (1H, s), 9.00 (1H, s), 12.94 (1H, s). |
| 61 | 61 | 11.44 | 347.0580 | 347.0597 | C18H10N4O2S | 400 MHz (DMSO d6) 7.45-7.51 (2H, m), 7.70-7.73 (1H, m), 8.14-8.16 (1H, m), 8.21 (1H, m), 8.28 (1H, s), 8.49 (1H, s), 8.90 (1H, s), 9.01 (1H, s), 12.92 (1H, s). |

-continued

| Ex. | Comp. No. | HPLC Retention Time | Obs Mass (M+ + H) | Pred Mass (M+ + H) | Formula (M) | 1H NMR |
|---|---|---|---|---|---|---|
| 62 | 62 | 5.78 | 292.0817 | 292.0829 | C15H9N5O2 | |
| 63 | 63 | 11.31 | 337.0749 | 337.0754 | C17H12N4O2S | 400 MHz (DMSO d6) 2.49 (3H, s), 7.40 (2H, d, J = 8.0 Hz), 7.59 (2H, d, J = 8.0 Hz), 8.18 (1H, s), 8.32 (1H, s), 8.77 (1H, s), 8.90 (1H, s), 12.86 (1H, s). |
| 64 | 64 | 9.99 | 376.1395 | 376.1404 | C20H17N5O3 | 400 MHz (DMSO d6) 3.24 (4H, t, J = 4.0 Hz), 3.76 (4H, t, J = 4.0 Hz), 7.13 (2H, d, J = 8.0 Hz), 7.59 (2H, d, J = 8.0 Hz), 8.23 (1H, s), 8.33 (1H, s), 8.81 (1H, s), 8.95 (1H, s), 12.88 (1H, s). |
| 65 | 65 | 12.61 | 367.1192 | 367.1190 | C22H14N4O2 | 400 MHz (DMSO d6) 7.40-7.44 (1H, m), 7.50-7.53 (2H, m), 7.77-7.83 (4H, m), 7.90-7.92 (2H, m), 8.26 (1H, s), 8.43 (1H, s), 8.91 (1H, s), 8.99 (1H, s). |
| 66 | 66 | 12.49 | 397.1290 | 397.1295 | C23H16N4O3 | 400 MHz (DMSO d6) 5.21 (2H, s), 7.23 (2H, d, J = 8.0 Hz), 7.34-7.50 (5H, m), 7.66 (2H, d, J = 8.0 Hz), 8.24 (1H, s), 8.36 (1H, s), 8.81 (1H, s), 8.96 (1H, s), 12.86 (1H, s). |
| 67 | 67 | 8.46 | 334.1281 | 334.1299 | C18H15N5O2 | 400 MHz (DMSO d6) 2.97 (6H, s), 6.89-6.95 (2H, m), 6.99 (1H, s), 7.37 (1H, t, J = 8.0 Hz), 8.25 (1H, s), 8.37 (1H, s), 8.85 (1H, s), 8.97 (1H, s). |
| 68 | 68 | 7.10 | 306.0974 | 306.0986 | C16H11N5O2 | 400 MHz (DMSO d6) 5.62 (2H, s), 6.71 (2H, d, J = 8.0 Hz), 7.39 (2H, d, J = 8.0 Hz), 8.21 (1H, s), 8.27 (1H, s), 8.75 (1H, s), 8.92 (1H, s), 12.84 (1H, s). |
| 69 | 69 | 8.57 | 384.0774 | 384.0761 | C17H13N5O4S | 400 MHz (DMSO d6) 3.10 (3H, s), 7.38 (2H, d, J = 8.0 Hz), 7.69 (2H, d, J = 8.0 Hz), 8.25 (1H, s), 8.39 (1H, s), 8.83 (1H, s), 8.96 (1H, s), 10.13 (1H, s), 12.89 (1H, s). |
| 70 | 70 | 8.23 | 404.1347 | 404.1353 | C21H17N5O4 | 400 MHz (DMSO d6) 3.51-3.77 (8H, m), 7.63 (2H, d, J = 8.0 Hz), 7.79 (2H, d, J = 8.0 Hz), 8.26 (1H, s), 8.44 (1H, s), 8.88 (1H, s), 8.99 (1H, s). |

Example 71

Synthesis of 1-[4-cyano-5-(3-methylsulfonylphenyl) pyridin-2-yl]-1H-pyrazole-4-carboxylic acid (compound No. 71) (synthetic method (B))

(1) A reaction mixture prepared by suspending 5.51 g of 5-bromo-2-chloropyridine-4-carbaldehyde, 26.5 g of trimethyl orthoformate, and 4.75 g of p-toluenesulfonic acid monohydrate in 50 mL of methanol was heated at 70° C. for 4 hours. Water was added to the reaction mixture, which was then extracted with ethyl acetate. The organic layer was washed with saturated aqueous sodium hydrogencarbonate solution and brine, then dried, and concentrated in vacuo to give 5.48 g of 5-bromo-2-chloro-4-(dimethoxymethyl)-pyridine.

$^1$H-NMR (400 MHz, CDCl$_3$) δ (ppm): 3.39 (6H, s), 5.46 (1H, s), 7.57 (1H, s), 8.49 (1H, s).

(2) A reaction mixture prepared by suspending 5.33 g of 5-bromo-2-chloro-4-(dimethoxymethyl)-pyridine, 2.33 g of ethyl 1H-pyrazole-4-carboxylate, and 4.14 g of potassium carbonate in 50 mL of dimethylformamide was heated at 90° C. for 7 hours under a nitrogen atmosphere. After the reaction mixture was cooled to room temperature, water was added to the reaction mixture, which was then extracted with ethyl acetate. The organic layer was washed with brine, then dried, and concentrated in vacuo to give a crude product of ethyl 1-(5-bromo-4-(dimethoxymethyl)pyridin-2-yl)-1H-pyrazole-4-carboxylate.

A mixture prepared by first suspending the crude product obtained above in 25 mL of formic acid and then adding 2.78 g of hydroxylamine monohydrochloride was heated at 70° C. for 30 minutes under a nitrogen atmosphere. After the formation of an oxime was confirmed, a reaction mixture prepared by adding 2.72 g of sodium formate and 10.2 g of acetic anhydride to the above mixture was heated at 110° C. for 15 hours. After the reaction mixture was cooled to room temperature, 25 mL of water was added, followed by washing with 100 mL of water to give 2.26 g of ethyl 1-(5-bromo-4-cyanopyridin-2-yl)-1H-pyrazole-4-carboxylate.

$^1$H-NMR (400 MHz, CDCl$_3$) δ (ppm): 1.38 (3H, t, J=8.0 Hz), 4.35 (2H, q, J=8.0 Hz), 8.14 (1H, s), 8.29 (1H, s), 8.71 (1H, s), 8.97 (1H, s).

(3) A reaction mixture prepared by suspending 80.3 mg of ethyl 1-(5-bromo-4-cyanopyridin-2-yl)-1H-pyrazole-4-carboxylate, 75.0 mg of 3-(methylsulfonyl)phenylboronic acid, 10.2 mg of palladium chloride-1,1'-bis(diphenylphosphino) ferrocene, and 106.1 mg of tripotassium phosphate in 0.8 mL of a mixed solvent of 1,4-dioxane/water=3/1 was heated at 90° C. for 15 hours under a nitrogen atmosphere. After the reaction mixture was cooled to room temperature, 2 mL of water and 4 mL of ethyl acetate were added, followed by stirring. The organic phase was concentrated and dried in vacuo to give a crude product of ethyl 1-[4-cyano-5-(3-methylsulfonylphenyl)pyridin-2-yl]-1H-pyrazole-4-carboxylate.

A reaction mixture prepared by dissolving the crude product obtained above in 0.8 mL of a 4 M solution of hydrochloric acid in 1,4-dioxane and adding 0.2 mL of 6 M hydrochloric acid was heated at 100° C. for 14 hours. The reaction mixture was cooled to room temperature and then concentrated to give a crude product of 1-[4-cyano-5-(3-methylsulfonylphenyl)pyridin-2-yl]-1H-pyrazole-4-carboxylic acid. This was purified by reversed phase HPLC to give 18.1 mg of 1-[4-cyano-5-(3-methylsulfonylphenyl)pyridin-2-yl]-1H-pyrazole-4-carboxylic acid.

$^1$H-NMR (400 MHz, DMSO d$_6$) δ (ppm): 3.30 (3H, s), 7.89 (1H, dd, J=8.0 Hz, 8.0 Hz), 8.09 (1H, d, J=8.0 Hz), 8.11 (1H, d, J=8.0 Hz), 8.27 (2H, s), 8.46 (1H, s), 8.95 (1H, s), 9.00 (1H, s), 12.91 (1H, s).

HPLC Retention Time: 8.60 min.
Obs Mass (M$^+$+H): 369.0645
Pred Mass (M$^+$+H): 369.0652
Formula (M): C$_{17}$H$_{12}$N$_4$O$_4$S Examples 72 to 74

Using the above reference example compound as the starting material, compound Nos. 72 to 74 were synthesized in the same manner as in Example 71.

| Ex. | Comp. No. | HPLC Retention Time | Obs Mass (M$^+$ + H) | Pred Mass (M$^+$ + H) | Formula (M) | 1H NMR |
|---|---|---|---|---|---|---|
| 72 | 72 | 10.15 | 334.0575 | 334.0582 | C16H9N5O4 | 400 MHz (DMSO d6) 7.91 (1H, dd, J = 8.0 Hz, 8.0 Hz), 8.19 (1H, d, J = 8.0 Hz), 8.27 (1H, s), 8.42 (1H, d, J = 8.0 Hz), 8.47 (1H, s), 8.60 (1H, s), 8.95 (1H, s), 9.01 (1H, s). |
| 73 | 73 | 11.53 | 395.1138 | 395.1139 | C23H14N4O3 | 400 MHz (DMSO d6) 7.58-7.62 (2H, m), 7.70-7.74 (1H, m), 7.79-7.81 (2H, m), 7.90-7.95 (4H, m), 8.27 (1H, s), 8.47 (1H, s), 8.93 (1H, s), 9.00 (1H, s). |
| 74 | 74 | 9.61 | 333.0964 | 333.0982 | C18H12N4O3 | 400 MHz (DMSO d6) 2.66 (3H, s), 7.87 (2H, d, J = 8.0 Hz), 8.15 (2H, d, J = 8.0 Hz), 8.27 (1H, s), 8.45 (1H, s), 8.90 (1H, s), 8.99 (1H, s). |

Example 75

Synthesis of 1-(5-cyano-6-phenylpyridin-3-yl)-1H-pyrazole-4-carboxylic acid (compound No. 75) (synthetic method (C))

(1) A reaction mixture prepared by suspending 255 mg of 2,3-dibromo-5-fluoropyridine, 168 mg of ethyl 1H-pyrazole-4-carboxylate, and 207 mg of potassium carbonate in 2 mL of dimethyl sulfoxide was heated at 120° C. for 2 hours under a nitrogen atmosphere. Water was added to the reaction mixture, which was then extracted with ethyl acetate. The organic layer was washed with saturated aqueous sodium hydrogencarbonate solution and brine, then dried, and concentrated in vacuo to give a crude product of ethyl 1-(5,6-dibromopyridine)-1H-pyrazole-4-carboxylate. This was purified by column chromatography (hexane/ethyl acetate=9/1) to give 164 mg of ethyl 1-(5,6-dibromopyridine)-1H-pyrazole-4-carboxylate.

$^1$H-NMR (400 MHz, CDCl$_3$) δ (ppm): 1.39 (3H, t, J=8.0 Hz), 4.36 (2H, q, J=8.0 Hz), 8.15 (1H, s), 8.37 (1H, d, J=4.0 Hz), 8.43 (1H, s), 8.72 (1H, d, J=4.0 Hz).

ESI/MS m/e: 373.9, 375.9, 377.9 (M$^+$+H, C$_{11}$H$_{10}$Br$_2$N$_3$O$_2$).

(2) A suspension was prepared by adding 82.0 mg of ethyl 1-(5,6-dibromopyridine)-1H-pyrazole-4-carboxylate, 29.3 mg of phenylboronic acid, and 60.5 mg of potassium carbonate were suspended in 1.5 mL of a mixed solution of 1,4-dioxane/water=4/1. A reaction mixture prepared by adding 12.6 mg of tetrakis(triphenylphosphine)palladium to the suspension was heated at 80° C. for 7 hours under a nitrogen atmosphere. Water was added to the reaction mixture, which was then extracted with ethyl acetate. The organic layer was washed with brine, then dried, and concentrated in vacuo to give a crude product of ethyl 1-(5-bromo-6-phenylpyridin-3-yl)-1H-pyrazole-4-carboxylate. This was purified by column chromatography (hexane/ethyl acetate=3/1) to give 82.2 mg of ethyl 1-(5-bromo-6-phenylpyridine-3-yl)-1H-pyrazole-4-carboxylate.

ESI/MS m/e: 372.0, 374.0 (M$^+$+H, C$_{17}$H$_{15}$BrN$_3$O$_2$).

(3) A reaction mixture prepared by suspending 82.2 mg of ethyl 1-(5-bromo-6-phenylpyridin-3-yl)-1H-pyrazole-4-carboxylate and 31.3 mg of copper (I) cyanide in 1.5 mL of dimethylformamide was heated at 160° C. for 6 hours under a nitrogen atmosphere. After the reaction mixture was cooled to room temperature, insoluble matter was removed by filtration through celite, and water was added to the filtrate, which was then extracted with ethyl acetate. The organic layer was washed with brine, then dried, and concentrated in vacuo to give a crude product of ethyl 1-(5-cyano-6-phenylpyridin-3-yl)-1H-pyrazole-4-carboxylate. This was purified by column chromatography (hexane/ethyl acetate=3/1) to give 54.2 mg of ethyl 1-(5-cyano-6-phenylpyridin-3-yl)-1H-pyrazole-4-carboxylate.

ESI/MS m/e: 319.1 (M$^+$+H, C$_{18}$H$_{15}$N$_4$O$_2$).

(4) A reaction mixture prepared by suspending 54.2 mg of ethyl 1-(5-cyano-6-phenylpyridin-3-yl)-1H-pyrazole-4-carboxylate was suspended in 1.0 mL of a mixed solution of tetrahydrofuran/methanol=1/1 and adding 0.2 mL of 2 M sodium hydroxide aqueous solution was heated at 50° C. for 2 hours under a nitrogen atmosphere. 0.2 mL of 2 M hydrochloric acid was added to the reaction mixture, which was then extracted with ethyl acetate. The organic layer was washed with brine, then dried, and concentrated in vacuo to give a crude product of 1-(5-cyano-6-phenylpyridine-3-yl)-1H-pyrazole-4-carboxylic acid. This was purified by reversed phase HPLC to give 6.35 mg of 1-(5-cyano-6-phenylpyridine-3-yl)-1H-pyrazole-4-carboxylic acid.

$^1$H-NMR (400 MHz, DMSO d$_6$) δ (ppm): 7.58-7.59 (3H, m), 7.89-7.91 (2H, m), 8.22 (1H, s), 8.97 (1H, d, J=4.0 Hz), 9.27 (1H, s), 9.50 (1H, d, J=4.0 Hz), 12.93 (1H, brs).

HPLC Retention Time: 9.76 min
Obs Mass (M$^+$+H): 291.0875
Pred Mass (M$^+$+H): 291.0877
Formula (M): C$_{16}$H$_{10}$N$_4$O$_2$

Examples 76 to 84

Using the above ethyl 1-(5,6-dibromopyridine-1H-pyrazole-4-carboxylate as the starting material, compound Nos. 76 to 84 were synthesized in the same manner as in Example 75.

| Ex. | Comp. No. | HPLC Retention Time | Obs Mass ($M^+ + H$) | Pred Mass ($M^+ + H$) | Formula (M) | 1H NMR |
|---|---|---|---|---|---|---|
| 76 | 76 | 9.57 | 309.0772 | 309.0782 | C16H9N4O2F | 400 MHz (DMSO d6) 7.34-8.00 (4H, m), 8.23 (1H, s), 9.01 (1H, d, J = 4.0 Hz), 9.27 (1H, s), 9.53 (1H, d, J = 4.0 Hz), 12.86 (1H, brs). |
| 77 | 77 | 9.97 | 327.0685 | 327.0688 | C16H8N4O2F2 | |
| 78 | 78 | 10.35 | 323.0937 | 323.0939 | C17H11N4O2F | |
| 79 | 79 | 10.34 | 323.0940 | 323.0939 | C17H11N4O2F | |
| 80 | 80 | 9.92 | 327.0688 | 327.0688 | C16H8N4O2F2 | |
| 81 | 81 | 9.94 | 327.0691 | 327.0688 | C16H8N4O2F2 | |
| 82 | 82 | 10.84 | 323.0934 | 323.0939 | C17H11N4O2F | |
| 83 | 83 | 10.93 | 323.0949 | 323.0939 | C17H11N4O2F | |
| 84 | 84 | 9.76 | 339.0889 | 339.0888 | C17H11N4O3F | |

Example 85

Synthesis of 1-(6-cyano-5-phenylpyridin-2-yl)-1H-pyrazole-4-carboxylic acid (compound No. 85) (synthetic method (D))

(1) A suspension prepared by adding 2.73 g of 2-cyano-3-hydroxypyridine to 60 mL of a mixed solution of acetonitrile/water=5/1 was cooled to 0° C. A reaction mixture prepared by adding 4.85 g of N-bromosuccinimide slowly to the suspension was stirred for 2 hours under a nitrogen atmosphere. Water was added to the reaction mixture, which was then extracted with ethyl acetate. The organic layer was washed with brine, then dried, and concentrated in vacuo to give 5.39 g of a crude product of 6-bromo-2-cyano-3-hydroxypyridine.

(2) A reaction mixture prepared by first suspending 5.39 g of 6-bromo-2-cyano-3-hydroxypyridine and 4.71 g of potassium carbonate in 60 mL of dimethylformamide and then adding 4.66 g of benzyl bromide was heated at 60° C. for 12 hours. After the reaction mixture was cooled to room temperature, 60 mL of water was added and purification was conducted by conventional means to give 4.73 g of 3-benzyloxy-6-bromo-2-cyanopyridine.

$^1$H-NMR (400 MHz, CDCl$_3$) δ (ppm): 5.26 (2H, s), 7.24 (1H, d, J=8.0 Hz), 7.36-7.44 (5H, m), 7.57 (1H, d, J=8.0 Hz)

(3) A reaction mixture prepared by first suspending 2.64 g of 3-benzyloxy-6-bromo-2-cyanopyridine, 1.44 g of ethyl 1H-pyrazole-4-carboxylate, 98 mg of copper iodide and 2.29 g of potassium carbonate were suspended in 20 mL of toluene and then adding 236 mg of trans-N,N'-dimethylcyclohexane-1,2-diamine was heated at 100° C. for 12 hours under a nitrogen atmosphere. After the reaction mixture was cooled to room temperature, water was added thereto, which was then extracted with ethyl acetate. The organic layer was washed with brine, then dried, and concentrated in vacuo. The crude product obtained was separated and purified by silica gel column chromatography to give 1.30 g of ethyl 1-(5-benzyloxy-6-cyanopyridin-2-yl)-1H-pyrazole-4-carboxylate.

(4) A reaction mixture prepared by first suspending 1.39 g of ethyl 1-(5-benzyloxy-6-cyanopyridin-2-yl)-1H-pyrazole-4-carboxylate was suspended in 30 mL of a mixed solution of tetrahydrofuran/ethanol=1/1 and then adding 409 mg of palladium/carbon (10% wt) was stirred at room temperature for 14 hours under a hydrogen atmosphere. The reaction mixture was filtered, and the filtrate was concentrated in vacuo to give 1.02 g of ethyl 1-(6-cyano-5-hydroxypyridin-2-yl)-1H-pyrazole-4-carboxylate.

(5) A mixture prepared by suspending 46 mg of ethyl 1-(6-cyano-5-hydroxypyridin-2-yl)-1H-pyrazole-4-carboxylate in 1 mL of dichloromethane and adding 35 mg of N,N-diisopropylethylamine was added, followed by cooling to 0° C. A reaction mixture prepared by adding 76 mg of trifluoromethanesulfonic anhydride to the suspension was stirred at room temperature for 4 hours under a nitrogen atmosphere. Water was added to the reaction mixture, which was then extracted with ethyl acetate. The organic layer was washed with brine, then dried, and concentrated in vacuo. The crude product obtained was separated and purified by silica gel column chromatography to give 45.3 mg of ethyl 1-[6-cyano-5-(trifluoromethylsulfonyloxy)pyridin-2-yl]-1H-pyrazole-2-carboxylate.

$^1$H-NMR (400 MHz, CDCl$_3$) δ (ppm): 1.40 (3H, t, J=8.0 Hz), 4.37 (2H, q, J=8.0 Hz), 8.00 (1H, d, J=8.0 Hz), 8.15 (1H, s), 8.39 (1H, d, J=8.0 Hz), 8.98 (1H, s).

(6) A reaction mixture prepared by first suspending 46.8 mg of ethyl 1-[6-cyano-5-(trifluoromethylsulfonyloxy)pyridin-2-yl]-1H-pyrazole-2-carboxylate, 17.6 mg of phenylboronic acid, and 7.8 mg of palladium chloride-1,1'-bis(diphenylphosphino)ferrocene-dichloromethane complex were suspended in 1.0 mL of 1,2-dimethoxyethane and then adding 0.12 mL of 1 M potassium carbonate aqueous solution was heated at 80° C. for 3 hours under a nitrogen atmosphere. Water was added to the reaction mixture, which was then extracted with ethyl acetate. The organic layer was washed with brine, then dried, and concentrated in vacuo to give a crude product of ethyl 1-(6-cyano-5-phenylpyridin-2-yl)-1H-pyrazole-4-carboxylate.

A reaction mixture prepared by first suspending the above crude product in 1.5 mL of a mixed solution of tetrahydrofuran/methanol=2/1 and then adding 0.24 mL of 2 M sodium hydroxide aqueous solution was heated at 50° C. for 4 hours. After the reaction mixture was cooled to room temperature, 0.24 mL of 2 M hydrochloric acid were added, followed by extraction with ethyl acetate and concentration in vacuo. The crude product obtained was purified by reversed phase HPLC to give 18.8 mg of 1-(6-cyano-5-phenylpyridin-2-yl)-1H-pyrazole-4-carboxylic acid.

$^1$H-NMR (400 MHz, DMSO d$_6$) δ (ppm): 7.56-7.61 (3H, m), 7.70-7.71 (2H, d, J=4.0 Hz), 8.25 (1H, s), 8.30-8.37 (2H, m), 8.97 (1H, s), 12.95 (1H, s).

HPLC Retention Time: 10.40 min.
Obs Mass ($M^+$+H): 291.0874
Pred Mass ($M^+$+H): 291.0877
Formula (M): $C_{16}H_{10}N_4O_2$ Examples 86 to 96

Using as a raw material the ethyl 1-[6-cyano-5-(trifluoromethylsulfonyloxy)pyridine-2-yl]-1H-pyrazole-2-carboxylate obtained above in (5) of Example 85, compound Nos. 86 to 96 were synthesized in the same manner as in Example 85.

| Ex. | Comp. No. | HPLC Retention Time | Obs Mass (M⁺ + H) | Pred Mass (M⁺ + H) | Formula (M) | 1H NMR |
|---|---|---|---|---|---|---|
| 86 | 86 | 10.37 | 309.0776 | 309.0782 | C16H9N4O2F | 400 MHz (DMSO d6) 7.41-7.50 (2H, m), 7.61-7.69 (2H, m), 8.26 (1H, s), 8.36 (2H, s), 8.99 (1H, s), 12.95 (1H, s). |
| 87 | 87 | 11.15 | 323.0931 | 323.0939 | C17H11N4O2F | 400 MHz (DMSO d6) 2.42 (3H, s), 7.27 (2H, dd, J = 24.0 Hz, 8.0 Hz), 7.54 (1H, dd, J = 8.0 Hz, 8.0 Hz), 8.26 (1H, s), 8.33 (2H, s), 8.98 (1H, s), 12.94 (1H, s). |
| 88 | 88 | 11.10 | 323.0939 | 323.0939 | C17H11N4O2F | 400 MHz (DMSO d6) 2.37 (3H, s), 7.32-7.45 (3H, m), 8.26 (1H, s), 8.34 (2H, s), 8.99 (1H, s), 12.94 (1H, s). |
| 89 | 89 | 10.51 | 309.0780 | 309.0782 | C16H9N4O2F | 400 MHz (DMSO d6) 7.45 (2H, dd, J = 8.0 Hz, 8.0 Hz), 7.77 (2H, dd, J = 4.0 Hz, 8.0 Hz), 8.26 (1H, s), 8.30-8.36 (2H, m), 8.98 (1H, s). |
| 90 | 90 | 10.60 | 327.0677 | 327.0688 | C16H8N4O2F2 | 400 MHz (DMSO d6) 7.35 (1H, td, J = 8.0 Hz, 4.0 Hz), 7.57 (1H, td, J = 8.0 Hz, 4.0 Hz), 7.76 (1H, td, J = 8.0 Hz, 8.0 Hz), 8.26 (1H, s), 8.35 (2H, s), 8.99 (1H, s), 12.93 (1H, s). |
| 91 | 91 | 10.55 | 339.0885 | 339.0888 | C17H11N4O3F | |
| 92 | 92 | 11.16 | 305.1038 | 305.1033 | C17H12N4O2 | 400 MHz (DMSO d6) 2.41 (3H, s), 7.37-7.38 (1H, m), 7.45-7.49 (3H, m), 8.25 (1H, s), 8.29-8.35 (2H, m), 12.91 (1H, s). |
| 93 | 93 | 11.24 | 335.1134 | 335.1139 | C18H14N4O3 | 400 MHz (DMSO d6) 1.36 (3H, t, J = 8.0 Hz), 4.11 (2H, q, J = 8.0 Hz), 7.10 (1H, dd, J = 8.0 Hz, 4.0 Hz), 7.22-7.25 (3H, m), 7.48 (1H, t, J = 8.0 Hz), 8.25 (1H, s), 8.28-8.36 (2H, m), 12.91 (1H, s). |
| 94 | 94 | 11.28 | 323.0943 | 323.0939 | C17H11N4O2F | 400 MHz (DMSO d6) 2.33 (3H, s), 7.37 (1H, t, J = 8.0 Hz), 7.57-7.59 (2H, m), 7.63 (1H, d, J = 8.0 Hz), 8.25 (1H, s), 8.29-8.34 (2H, m), 12.91 (1H, s). |
| 95 | 95 | 10.40 | 327.0688 | 327.0688 | C16H8N4O2F2 | 400 MHz (DMSO d6) 7.40 (2H, t, J = 8.0 Hz), 7.67-7.75 (1H, m), 8.27 (1H, s), 8.39-8.46 (2H, m), 9.00 (1H, s), 12.93 (1H, s). |
| 96 | 96 | 10.55 | 339.0884 | 339.0888 | C17H11N4O3F | 400 MHz (DMSO d6) 3.82 (3H, s), 7.06 (1H, t, J = 8.0 Hz), 7.12 (1H, d, J = 8.0 Hz), 7.58 (1H, q, J = 8.0 Hz), 8.25 (1H, s), 8.29-8.35 (2H, m), 8.98 (1H, s), 12.90 (1H, s). |

Examples 97 to 107

Using the above reference example compound as the starting material, compound Nos. 97 to 107 were synthesized in the same manner as in Example 1.

| Ex. | Comp. No. | HPLC Retention Time | Obs Mass (M⁺ + H) | Pred Mass (M⁺ + H) | Formula (M) | 1H NMR |
|---|---|---|---|---|---|---|
| 97 | 97 | 10.26 | 306.0978 | 306.0986 | C16H11N5O2 | 400 MHz (DMSO d6) 7.54-7.60 (3H, m), 7.66-7.69 (2H, m), 8.03 (1H, s), 8.68 (1H, s), 8.74 (1H, s). |
| 98 | 98 | 10.22 | 324.0897 | 324.0891 | C16H10FN5O2 | 400 MHz (DMSO d6) 5.92 (2H, brs), 7.39-7.48 (2H, m), 7.58-7.65 (2H, m), 8.08 (1H, s), 8.69 (1H, s), 8.73 (1H, s), 12.73 (1H, brs). |

| Ex. | Comp. No. | HPLC Retention Time | Obs Mass (M⁺ + H) | Pred Mass (M⁺ + H) | Formula (M) | 1H NMR |
|---|---|---|---|---|---|---|
| 99 | 99 | 10.39 | 324.0894 | 324.0891 | C16H10FN5O2 | |
| 100 | 100 | 11.20 | 340.0587 | 340.0596 | C16H10ClN5O2 | 400 MHz (DMSO d6) 5.92 (2H, brs), 7.64-7.72 (4H, m), 8.03 (1H, s), 8.67 (1H, s), 8.74 (1H, s). |
| 101 | 101 | 10.98 | 320.1133 | 320.1142 | C17H13N5O2 | 400 MHz (DMSO d6) 2.40 (3H, s), 5.90 (2H, brs), 7.34-7.36 (1H, m), 7.44-7.47 (3H, m), 8.01 (1H, s), 8.67 (1H, s), 8.72 (1H, s), 12.71 (1H, brs). |
| 102 | 102 | 10.32 | 336.1088 | 336.1091 | C17H13N5O3 | |
| 103 | 103 | 10.97 | 338.1044 | 338.1048 | C17H12FN5O2 | 400 MHz (DMSO d6) 2.41 (3H, s), 5.91 (2H, brs), 7.19-7.31 (3H, m), 7.47-7.52 (1H, m), 8.06 (1H, s), 8.68 (1H, s), 8.69 (1H, s), 12.71 (1H, brs). |
| 104 | 104 | 10.91 | 338.1036 | 338.1048 | C17H12FN5O2 | |
| 105 | 105 | 10.43 | 342.0791 | 342.0797 | C16H9F2N5O2 | |
| 106 | 106 | 11.10 | 338.1056 | 338.1048 | C17H12FN5O2 | |
| 107 | 107 | 10.33 | 354.0983 | 354.0997 | C17H12FN5O3 | |

Example 108

The xanthine oxidase inhibitory activity was measured for the compounds synthesized according to the above Examples.

(1) Preparation of Test Compounds

After a test compound was dissolved in DMSO (manufactured by Sigma Co.) so that the concentration is 20 mM, the test compound was prepared and used at a desired concentration at the time of use.

(2) Measurement Method

The evaluation of the xanthine oxidase inhibitory activity of the compounds of the present invention was conducted by partially modifying the method described in the literature (Method Enzymatic Analysis, 1, 521-522, 1974). The present evaluation is based on the oxidase type xanthine oxidase inhibitory activity evaluation. That is, a xanthine (manufactured by Sigma Co.) solution prepared at 10 mM in advance using a 20 mM sodium hydroxide solution was adjusted to 30 μM using a 100 mM phosphate buffer solution, and 75 μL/well of each solution was added into a 96-well plate. Aliquots (1.5 μL/well) of each test sample, which was diluted with DMSO so that the concentration is 100 times the final concentration, were added into a 96-well plate, and after mixing, the absorbance at 290 nm was measured by a microplate reader SPECTRA MAX Plus 384 (manufactured by Molecular Devices, LLC). Subsequently, oxidase type xanthine oxidase (derived from buttermilk, supplied by Calbiochem Novabiochem Corp.) was prepared at 30.6 mU/mL using a 100 mM phosphate buffer solution and 73.5 μL/well of each solution was added. Immediately after mixing, the change in absorbance at 290 nm was measured for 5 minutes. The enzyme activity when DMSO was used instead of a test compound solution was defined as 100%, the inhibitory rate of the test compounds was calculated and the 50% inhibitory concentration with respect to oxidase type xanthine oxidase was calculated by fitting to the dose-response curve.

The results are shown in the following table. Note that the symbols (+, ++, +++) in the table represent inhibitory activity values as shown below.

10.0 nM ≤ IC₅₀: +
5.0 nM ≤ IC₅₀ < 10.0 nM: ++
1.0 nM ≤ IC₅₀ < 5.0 nM: +++

| Compound Number | Inhibitory Activity |
|---|---|
| 1 | +++ |
| 2 | +++ |
| 3 | ++ |
| 4 | ++ |
| 5 | +++ |
| 6 | +++ |
| 7 | +++ |
| 8 | + |
| 9 | + |
| 10 | +++ |
| 11 | ++ |
| 12 | ++ |
| 13 | +++ |
| 14 | +++ |
| 15 | +++ |
| 16 | +++ |
| 17 | ++ |
| 18 | ++ |
| 19 | +++ |
| 20 | +++ |
| 21 | +++ |
| 22 | +++ |
| 23 | ++ |
| 24 | + |
| 25 | + |
| 26 | + |
| 27 | + |
| 28 | + |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | ++ |
| 41 | +++ |
| 42 | +++ |
| 43 | +++ |
| 44 | +++ |
| 45 | ++ |
| 46 | ++ |
| 47 | +++ |
| 48 | +++ |
| 49 | + |
| 50 | +++ |
| 51 | +++ |

-continued

| Compound Number | Inhibitory Activity |
|---|---|
| 52 | +++ |
| 53 | +++ |
| 54 | +++ |
| 55 | +++ |
| 56 | ++ |
| 57 | +++ |
| 58 | + |
| 59 | +++ |
| 60 | + |
| 61 | +++ |
| 62 | + |
| 63 | +++ |
| 64 | +++ |
| 65 | +++ |
| 66 | +++ |
| 67 | ++ |
| 68 | +++ |
| 69 | +++ |
| 70 | +++ |
| 71 | +++ |
| 72 | + |
| 73 | +++ |
| 74 | + |
| 75 | + |
| 76 | + |
| 77 | + |
| 79 | + |
| 80 | + |
| 81 | + |
| 82 | + |
| 83 | ++ |
| 84 | ++ |
| 85 | + |
| 86 | ++ |
| 88 | + |
| 89 | + |
| 90 | + |
| 91 | ++ |
| 92 | + |
| 93 | + |
| 94 | + |
| 95 | ++ |
| 96 | + |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |

Example 109

Hypouricemic Effect

Normal Mice

To 7 to 8-weeks-old Crlj:CD1-type male mice (Charles River Laboratories Japan, Inc.), test compounds suspended in 0.5% methylcellulose solution were administered by gavage using a feeding needle. Blood was taken from the heart at 6, 16, and 24 hours after the administration, after which the serum was separated. Blood uric acid levels were measured by the uricase method on an absorptiometer (Hitachi Autoanalyzer 7180) using a uric acid measurement kit (Autosera SUA: Sekisui Medical), and the percentage of hypouricemic effect was determined according to the following equation.

Percentage of hypouricemic effect (%)=(Level of uric acid of the control animal−Level of uric acid of the test compound-administered animal)×100/Level of uric acid of the control animal.

In this test, the excellent hypouricemic effects of the inventive compounds were confirmed. For example, the compounds of compound Nos. 1, 5, 10, 14, 19, 21, and 33 showed the percentage of hypouricemic effect of 70% or more 6 hours after oral administration of 1 mg/kg.

From the above results, it was shown that the compounds of the present invention have a strong hypouricemic effect.

Example 110

Hypouricemic Effect

Normal Rats

A test compound suspended in a 0.5% methylcellulose solution was administered to 8 to 9 week-old Sprague-Dawley male rats (Japan Charles River Co.) by oral gavage administration using a feeding needle. After the blood was collected from the tail vein at 6 hours and 24 hours after administration, the plasma was separated. The level of uric acid in the blood sample was measured by uricase method using an absorption spectrometer as well as a uric acid determination kit (L type Wako UA F: Wako Pure Chemical Industries, Ltd.). The percentage of hypouricemic effect was determined by the following expression:

Percentage of hypouricemic effect (%)=(Level of uric acid of the control animal−Level of uric acid of the test compound-administered animal)×100/Level of uric acid of the control animal.

The compound of compound No. 1 showed a hypouricemic effect of 70% or more at the dose of 1 mg/kg at 6 hours and 24 hours after administration. Also, the compounds of compound No. 97 and 98 showed a hypouricemic effect of 50% or more at the dose of 10 mg/kg at 6 hours and 24 hours after administration. From these results, it was shown that the compounds of the present invention have a strong and lasting hypouricemic effect.

Example 111

Hypouricemic Effects

*Cebus apella* Monkeys

To *Cebus apella* monkeys, test compounds suspended in 0.5% methylcellulose solution were administered by gavage into the stomach through the nasal cavity using a disposable catheter and a syringe. Blood was taken from the saphenous vein at 4 hours and 24 hours after the administration, after which the plasma was separated. The level of uric acid in the blood was measured using a uric acid measurement kit (L type Wako UA F: Wako Pure Chemical Industries, Ltd.) by the uricase method using an absorption spectrometer and the percentage of hypouricemic effect was determined by the following expression:

Percentage of hypouricemic effect (%)=(Level of uric acid of the control animal−Level of uric acid of the test compound-administered animal)×100/Level of uric acid of the control animal.

The compound of compound No. 1 showed a hypouricemic effect of 50% or more at the dose of 1 mg/kg at 4 hours and 24 hours after administration. From these results, it was shown that the compounds of the present invention had a strong and lasting hypouricemic effect also in Cebus apella monkeys.

Example 112

Hypouricemic Effect

Beagle Dogs

The hypouricemic effect of the compound (I) in beagle dogs was confirmed. A test compound suspended in a 0.5% methyl cellulose solution was orally administered by gavage to beagle dogs (Kitayama Labs). Blood was drawn from the cephalic vein at 24 hours after administration and plasma was separated. The level of uric acid in the plasma sample was measured using an LC-MS/MS method and the percentage of hypouricemic effect was determined by the following expression:

Percentage of hypouricemic effect (%)=(Level of uric acid of the control animal−Level of uric acid of the test compound-administered animal)×100/Level of uric acid of the control animal.

The compound of compound No. 1 showed a hypouricemic effect of 50% or more at the dose of 3 mg/kg at 24 hours after administration.

From these results, the compounds of the present invention were shown to have a strong and lasting hypouricemic effect in dogs.

In view of the above results, the inventive compounds of the present invention can be expected to exert potent hypouricemic effects even when they are administered once a day or at longer intervals. Clinically, in the treatment or prophylaxis of hyperuricemia and various diseases, particularly chronic diseases, resulting therefrom, it is important to continually lower uric acid levels, and the present invention can be expected to exert excellent effects on such diseases.

INDUSTRIAL APPLICABILITY

The compounds represented by the foregoing formula (I) of the present invention and pharmaceutically acceptable salts thereof have xanthine oxidase inhibitory activity, and can be used as therapeutic or prophylactic agents for diseases associated with xanthine oxidase, particularly gout, hyperuricemia, tumor lysis syndrome, urinary calculus, hypertension, dyslipidemia, diabetes, cardiovascular diseases such as arteriosclerosis or heart failure, renal diseases such as diabetic nephropathy, respiratory diseases such as chronic obstructive pulmonary disease, inflammatory bowel diseases, autoimmune diseases, or the like, to which they are clinically applicable as xanthine oxidase inhibitors.

The invention claimed is:

1. A compound or a pharmaceutically acceptable salt thereof represented by the following formula (I)

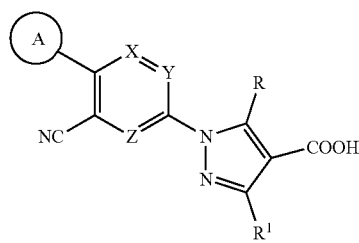

(I)

wherein:
A represents a $C_{6-10}$ aryl group or a heteroaryl group, wherein the aryl group or heteroaryl group may be unsubstituted or substituted with 1 to 3 groups Q which are the same or different from one another and selected from the group consisting of a halogen atom, —CN, —$NO_2$, a $C_{1-6}$ alkyl group, a $C_{3-7}$ cycloalkyl group, a $C_{1-6}$ halogenoalkyl group, a phenyl group, —$CH_2$—O—$R^2$, —O—$R^2$, —O—$C_{1-6}$ halogenoalkyl, —O-benzyl, —O-phenyl, —O—CO—$R^2$, —$NR^3R^4$, —NH—CO—$R^2$, —$CO_2$—$R^2$, —CO—$R^2$, —CO—$NR^3R^4$, —NH—$SO_2$—$R^2$, —CO-aryl, —S—$R^2$, —$SO_2$—$C_{1-6}$ alkyl, and —$SO_2$-phenyl;

X, Y, and Z represent $CR^5$ or a nitrogen atom, wherein one of X, Y, and Z represents a nitrogen atom and the remaining two represent $CR^5$;

R represents a hydrogen atom or a $C_{1-6}$ alkyl group;

$R^1$ represents a hydrogen atom, an amino group, or a $C_{1-6}$ alkyl group;

$R^2$ represents a hydrogen atom or a $C_{1-6}$ alkyl group;

$R^3$ and $R^4$ are the same or different from each other and are a hydrogen atom or a $C_{1-6}$ alkyl group, where $R^3$ and $R^4$ may be taken together to form with the nitrogen atom to which they are attached a nitrogen-containing saturated monocyclic heterocycle; and $R^5$ represents a hydrogen atom, a halogen atom, or a $C_{1-6}$ alkyl group.

2. The compound or a pharmaceutically acceptable salt thereof according to claim 1, wherein X and Z represent $CR^5$, and Y represents a nitrogen atom.

3. The compound or a pharmaceutically acceptable salt thereof according to claim 1, wherein Y and Z represent $CR^5$, and X represents a nitrogen atom.

4. The compound or a pharmaceutically acceptable salt thereof according to claim 1, wherein X and Y represent $CR^5$, and Z represents a nitrogen atom.

5. The compound or a pharmaceutically acceptable salt thereof according to claim 1, wherein $R^5$ represents a hydrogen atom.

6. The compound or a pharmaceutically acceptable salt thereof according to claim 1, wherein R and $R^1$ represent hydrogen atom.

7. The compound or a pharmaceutically acceptable salt thereof according to claim 1, wherein A represents a $C_{6-10}$ aryl group which may be unsubstituted or substituted with 1 to 2 groups Q which are the same or different from one another and selected from the group consisting of a halogen atom, —CN, —$NO_2$, a $C_{1-6}$ alkyl group, a $C_{3-7}$ cycloalkyl group, a $C_{1-6}$ halogenoalkyl group, a phenyl group, —$CH_2$—O—$R^2$, —O—$R^2$, —O—$C_{1-6}$ halogenoalkyl, —O-benzyl, —O-phenyl, —O—CO—$R^2$, —$NR^3R^4$, —NH—CO—$R^2$, —$CO_2$—$R^2$, —CO—$R^2$, —CO—$NR^3R^4$, —NH—$SO_2$—$R^2$, —CO-aryl, —S—$R^2$, —$SO_2$—$C_{1-6}$ alkyl, and —$SO_2$-phenyl.

8. The compound or a pharmaceutically acceptable salt thereof according to claim 7, wherein A represents a phenyl group which may be unsubstituted or substituted with 1 to 2 groups Q which are the same or different from one another and selected from the group consisting of a halogen atom, —CN, —$NO_2$, a $C_{1-6}$ alkyl group, a $C_{3-7}$ cycloalkyl group, a $C_{1-6}$ halogenoalkyl group, a phenyl group, —$CH_2$—O—$R^2$, —O—$R^2$, —O—$C_{1-6}$ halogenoalkyl, —O-benzyl, —O-phenyl, —O—CO—$R^2$, —$NR^3R^4$, —NH—CO—$R^2$, —$CO_2$—$R^2$, —CO—$R^2$, —CO—$NR^3R^4$, —NH—$SO_2$—$R^2$, —CO-aryl, —S—$R^2$, —$SO_2$—$C_{1-6}$ alkyl, and —$SO_2$-phenyl.

9. The compound or a pharmaceutically acceptable salt thereof according to any of claim 1, wherein A represents a heteroaryl group which may be unsubstituted or substituted with 1 to 2 groups Q which are the same or different from one another and selected from the group consisting of a halogen atom, —CN, —NO$_2$, a C$_{1-6}$ alkyl group, a C$_{3-7}$ cycloalkyl group, a C$_{1-6}$ halogenoalkyl group, a phenyl group, —CH$_2$—O—R$^2$, —O—R$^2$, —O—C$_{1-6}$ halogenoalkyl, —O-benzyl, —O-phenyl, —O—CO—R$^2$, —NR$^3$R$^4$, —NH—CO—R$^2$, —CO$_2$—R$^2$, —CO—R$^2$, —CO—NR$^3$R$^4$, —NH—SO$_2$—R$^2$, —CO-aryl, —S—R$^2$, —SO$_2$—C$_{1-6}$ alkyl, and —SO$_2$-phenyl.

10. The compound or a pharmaceutically acceptable salt thereof according to claim 9, wherein A represents a thienyl group which may be unsubstituted or substituted with 1 to 2 groups Q which are the same or different from one another and selected from the group consisting of a halogen atom, —CN, —NO$_2$, a C$_{1-6}$ alkyl group, a C$_{3-7}$ cycloalkyl group, a C$_{1-6}$ halogenoalkyl group, a phenyl group, —CH$_2$—O—R$^2$, —O—R$^2$, —O—C$_{1-6}$ halogenoalkyl, —O-benzyl, —O-phenyl, —O—CO—R$^2$, —NR$^3$R$^4$, —NH—CO—R$^2$, —CO$_2$—R$^2$, —CO—R$^2$, —CO—NR$^3$R$^4$, —NH—SO$_2$—R$^2$, —CO-aryl, —S—R$^2$, —SO$_2$—C$_{1-6}$ alkyl, and —SO$_2$-phenyl.

11. The compound or a pharmaceutically acceptable salt thereof according to claim 1, wherein A is unsubstituted.

12. The compound or a pharmaceutically acceptable salt thereof according to claim 1, wherein A is substituted with 1 to 3 groups Q which are the same or different from one another and selected from the group consisting of a halogen atom, a C$_{1-6}$ alkyl group, a C$_{3-7}$ cycloalkyl group, a C$_{1-6}$ halogenoalkyl group, a phenyl group, —O—R$^2$, and —O—C$_{1-6}$ halogenoalkyl.

13. The compound or a pharmaceutically acceptable salt thereof according to claim 12, wherein Q is selected from the group consisting of a halogen atom, a methyl group, and a methoxy group.

14. A compound selected from the following (1) to (107):
(1) 1-(4-cyano-5-phenylpyridin-2-yl)-1H-pyrazole-4-carboxylic acid;
(2) 1-[4-cyano-5-(4-methoxyphenyl)pyridin-2-yl]-1H-pyrazole-4-carboxylic acid;
(3) 1-[4-cyano-5-(2-ethoxyphenyl)pyridin-2-yl]-1H-pyrazole-4-carboxylic acid;
(4) 1-[4-cyano-5-(2-methylphenyl)pyridin-2-yl]-1H-pyrazole-4-carboxylic acid;
(5) 1-[4-cyano-5-(2-fluorophenyl)pyridin-2-yl]-1H-pyrazole-4-carboxylic acid;
(6) 1-[4-cyano-5-(2-chlorophenyl)pyridin-2-yl]-1H-pyrazole-4-carboxylic acid;
(7) 1-[4-cyano-5-(2-methoxyphenyl)pyridin-2-yl]-1H-pyrazole-4-carboxylic acid;
(8) 1-{4-cyano-5-[2-(trifluoromethyl)phenyl]pyridin-2-yl}-1H-pyrazole-4-carboxylic acid;
(9) 1-{4-cyano-5-[2-(trifluoromethoxy)phenyl]pyridin-2-yl}-1H-pyrazole-4-carboxylic acid;
(10) 1-[4-cyano-5-(3-methylphenyl)pyridin-2-yl]-1H-pyrazole-4-carboxylic acid;
(11) 1-[4-cyano-5-(3-fluorophenyl)pyridin-2-yl]-1H-pyrazole-4-carboxylic acid;
(12) 1-[4-cyano-5-(3-chlorophenyl)pyridin-2-yl]-1H-pyrazole-4-carboxylic acid;
(13) 1-[4-cyano-5-(3-methoxyphenyl)pyridin-2-yl]-1H-pyrazole-4-carboxylic acid;
(14) 1-[4-cyano-5-(4-methylphenyl)pyridin-2-yl]-1H-pyrazole-4-carboxylic acid;
(15) 1-[4-cyano-5-(4-chlorophenyl)pyridin-2-yl]-1H-pyrazole-4-carboxylic acid;
(16) 1-[4-cyano-5-(4-hydroxyphenyl)pyridin-2-yl]-1H-pyrazole-4-carboxylic acid;
(17) 1-[4-cyano-5-(2-ethoxy-6-fluorophenyl)pyridin-2-yl]-1H-pyrazole-4-carboxylic acid;
(18) 1-[4-cyano-5-(2-fluoro-6-methoxyphenyl)pyridin-2-yl]-1H-pyrazole-4-carboxylic acid;
(19) 1-[4-cyano-5-(2-fluoro-3-methoxyphenyl)pyridin-2-yl]-1H-pyrazole-4-carboxylic acid;
(20) 1-[4-cyano-5-(2,3-difluorophenyl)pyridin-2-yl]-1H-pyrazole-4-carboxylic acid;
(21) 1-[4-cyano-5-(thiophen-3-yl)pyridin-2-yl]-1H-pyrazole-4-carboxylic acid;
(22) 1-[4-cyano-5-(3-methylthiophen-2-yl)pyridin-2-yl]-1H-pyrazole-4-carboxylic acid;
(23) 1-[4-cyano-5-(furan-3-yl)pyridin-2-yl]-1H-pyrazole-4-carboxylic acid;
(24) 1-[4-cyano-5-(3-methoxypyridin-4-yl)pyridin-2-yl]-1H-pyrazole-4-carboxylic acid;
(25) 1-[4-cyano-5-(pyridin-3-yl)pyridin-2-yl]-1H-pyrazole-4-carboxylic acid;
(26) 1-(4-cyano-5-phenylpyridin-2-yl)-3-methyl-1H-pyrazole-4-carboxylic acid;
(27) 1-(4-cyano-5-phenylpyridin-2-yl)-3-(propan-2-yl)-1H-pyrazole-4-carboxylic acid;
(28) 1-(4-cyano-5-phenylpyridin-2-yl)-3,5-dimethyl-1H-pyrazole-4-carboxylic acid;
(29) 1-[4-cyano-5-(4-fluorophenyl)pyridin-2-yl]-1H-pyrazole-4-carboxylic acid;
(30) 1-[4-cyano-5-(3-ethoxyphenyl)pyridin-2-yl]-1H-pyrazole-4-carboxylic acid;
(31) 1-[4-cyano-5-(3-propoxyphenyl)pyridin-2-yl]-1H-pyrazole-4-carboxylic acid;
(32) 1-[4-cyano-5-(2,4-difluorophenyl)pyridin-2-yl]-1H-pyrazole-4-carboxylic acid;
(33) 1-[4-cyano-5-(2-fluoro-4-methylphenyl)pyridin-2-yl]-1H-pyrazole-4-carboxylic acid;
(34) 1-[4-cyano-5-(2-fluoro-5-methylphenyl)pyridin-2-yl]-1H-pyrazole-4-carboxylic acid;
(35) 1-[4-cyano-5-(2,5-difluorophenyl)pyridin-2-yl]-1H-pyrazole-4-carboxylic acid;
(36) 1-[4-cyano-5-(2-fluoro-3-methylphenyl)pyridin-2-yl]-1H-pyrazole-4-carboxylic acid;
(37) 1-[4-cyano-5-(4-fluoro-3-methylphenyl)pyridin-2-yl]-1H-pyrazole-4-carboxylic acid;
(38) 1-[4-cyano-5-(2,3-dimethylphenyl)pyridin-2-yl]-1H-pyrazole-4-carboxylic acid;
(39) 1-[4-cyano-5-(3-fluoro-4-methylphenyl)pyridin-2-yl]-1H-pyrazole-4-carboxylic acid;
(40) 1-[4-cyano-5-(3-chloro-4-fluorophenyl)pyridin-2-yl]-1H-pyrazole-4-carboxylic acid;
(41) 1-[4-cyano-5-(3-chloro-2-fluorophenyl)pyridin-2-yl]-1H-pyrazole-4-carboxylic acid;
(42) 1-[5-(4-carboxyphenyl)-4-cyanopyridin-2-yl]-1H-pyrazole-4-carboxylic acid;
(43) 1-{4-cyano-5-[4-(trifluoromethyl)phenyl]pyridin-2-yl}-1H-pyrazole-4-carboxylic acid;
(44) 1-{4-cyano-5-[4-(trifluoromethoxy)phenyl]pyridin-2-yl}-1H-pyrazole-4-carboxylic acid;
(45) 1-{4-cyano-5-[3-(trifluoromethyl)phenyl]pyridin-2-yl}-1H-pyrazole-4-carboxylic acid;
(46) 1-{4-cyano-5-[3-(difluoromethoxy)phenyl]pyridin-2-yl}-1H-pyrazole-4-carboxylic acid;
(47) 1-{4-cyano-5-[4-(propane-2-yl)phenyl]pyridin-2-yl}-1H-pyrazole-4-carboxylic acid;

(48) 1-{4-cyano-5-[3-(propane-2-yl)phenyl]pyridin-2-yl}-1H-pyrazole-4-carboxylic acid;
(49) 1-[4-cyano-5-(4-fluoro-2-methylphenyl)pyridin-2-yl]-1H-pyrazole-4-carboxylic acid;
(50) 1-[4-cyano-5-(4-fluoro-2-methoxyphenyl)pyridin-2-yl]-1H-pyrazole-4-carboxylic acid;
(51) 1-[4-cyano-5-(4-chloro-3-methylphenyl)pyridin-2-yl]-1H-pyrazole-4-carboxylic acid;
(52) 1-{4-cyano-5-[(4-propan-2-yloxy)phenyl]pyridin-2-yl}-1H-pyrazole-4-carboxylic acid;
(53) 1-[5-(4-tert-butylphenyl)-4-cyanopyridin-2-yl]-1H-pyrazole-4-carboxylic acid;
(54) 1-[4-cyano-5-(4-phenoxyphenyl)pyridin-2-yl]-1H-pyrazole-4-carboxylic acid;
(55) 1-{4-cyano-5-[4-(methoxymethyl)phenyl]pyridin-2-yl}-1H-pyrazole-4-carboxylic acid;
(56) 1-{4-cyano-5-[3-(2-methylpropoxy)phenyl]pyridin-2-yl}-1H-pyrazole-4-carboxylic acid;
(57) 1-[4-cyano-5-(naphthalen-2-yl)pyridin-2-yl]-1H-pyrazole-4-carboxylic acid;
(58) 1-[4-cyano-5-(4-methoxypyridin-3-yl)pyridin-2-yl]-1H-pyrazole-4-carboxylic acid;
(59) 1-{4-cyano-5-[6-(dimethylamino)pyridin-3-yl]pyridin-2-yl}-1H-pyrazole-4-carboxylic acid;
(60) 1-[4-cyano-5-(5-fluoropyridin-3-yl)pyridin-2-yl]-1H-pyrazole-4-carboxylic acid;
(61) 1-[5-(1-benzothiophen-3-yl)-4-cyanopyridin-2-yl]-1H-pyrazole-4-carboxylic acid;
(62) 1-[4-cyano-5-(pyridin-4-yl)pyridin-2-yl]-1H-pyrazole-4-carboxylic acid;
(63) 1-{4-cyano-5-[4-(methylsulfanyl)phenyl]pyridin-2-yl}-1H-pyrazole-4-carboxylic acid;
(64) 1-{4-cyano-5-[4-(morpholin-4-yl)phenyl]pyridin-2-yl}-1H-pyrazole-4-carboxylic acid;
(65) 1-[4-cyano-5-(4-phenylphenyl)pyridin-2-yl]-1H-pyrazole-4-carboxylic acid;
(66) 1-{5-[4-(benzyloxy)phenyl]-4-cyanopyridin-2-yl}-1H-pyrazole-4-carboxylic acid;
(67) 1-{4-cyano-5-[3-(dimethylamino)phenyl]pyridin-2-yl}-1H-pyrazole-4-carboxylic acid;
(68) 1-[5-(4-aminophenyl)-4-cyanopyridin-2-yl]-1H-pyrazole-4-carboxylic acid;
(69) 1-[4-cyano-5-(4-methanesulfonamidophenyl)pyridin-2-yl]-1H-pyrazole-4-carboxylic acid;
(70) 1-(4-cyano-5-{4-[(morpholin-4-yl)carbonyl]phenyl}pyridin-2-yl)-1H-pyrazole-4-carboxylic acid;
(71) 1-[5-(4-acetophenyl)-4-cyanopyridin-2-yl]-1H-pyrazole-4-carboxylic acid;
(72) 1-[4-cyano-5-(3-nitrophenyl)pyridin-2-yl]-1H-pyrazole-4-carboxylic acid;
(73) 1-[5-(4-benzoylphenyl)-4-cyanopyridin-2-yl]-1H-pyrazole-4-carboxylic acid;
(74) 1-[4-cyano-5-(4-methanesulfonylphenyl)pyridin-2-yl]-1H-pyrazole-4-carboxylic acid;
(75) 1-(5-cyano-6-phenylpyridin-3-yl)-1H-pyrazole-4-carboxylic acid;
(76) 1-[5-cyano-6-(2-fluorophenyl)pyridin-3-yl]-1H-pyrazole-4-carboxylic acid;
(77) 1-[5-cyano-6-(2,4-difluorophenyl)pyridin-3-yl]-1H-pyrazole-4-carboxylic acid;
(78) 1-[5-cyano-6-(2-fluoro-4-methylphenyl)pyridin-3-yl]-1H-pyrazole-4-carboxylic acid;
(79) 1-[5-cyano-6-(2-fluoro-5-methylphenyl)pyridin-3-yl]-1H-pyrazole-4-carboxylic acid;
(80) 1-[5-cyano-6-(2,5-difluorophenyl)pyridin-3-yl]-1H-pyrazole-4-carboxylic acid;
(81) 1-[5-cyano-6-(2,3-difluorophenyl)pyridin-3-yl]-1H-pyrazole-4-carboxylic acid;
(82) 1-[5-cyano-6-(4-fluoro-3-methylphenyl)pyridin-3-yl]-1H-pyrazole-4-carboxylic acid;
(83) 1-[5-cyano-6-(3-fluoro-4-methylphenyl)pyridin-3-yl]-1H-pyrazole-4-carboxylic acid;
(84) 1-[5-cyano-6-(2-fluoro-5-methoxyphenyl)pyridin-3-yl]-1H-pyrazole-4-carboxylic acid;
(85) 1-(6-cyano-5-phenylpyridin-2-yl)-1H-pyrazole-4-carboxylic acid;
(86) 1-[6-cyano-5-(2-fluorophenyl)pyridin-2-yl]-1H-pyrazole-4-carboxylic acid;
(87) 1-[6-cyano-5-(2-fluoro-4-methylphenyl)pyridin-2-yl]-1H-pyrazole-4-carboxylic acid;
(88) 1-[6-cyano-5-(2-fluoro-5-methylphenyl)pyridin-2-yl]-1H-pyrazole-4-carboxylic acid;
(89) 1-[6-cyano-5-(4-fluorophenyl)pyridin-2-yl]-1H-pyrazole-4-carboxylic acid;
(90) 1-[6-cyano-5-(2,4-difluorophenyl)pyridin-2-yl]-1H-pyrazole-4-carboxylic acid;
(91) 1-[6-cyano-5-(2-fluoro-5-methoxyphenyl)pyridin-2-yl]-1H-pyrazole-4-carboxylic acid;
(92) 1-[6-cyano-5-(3-methylphenyl)pyridin-2-yl]-1H-pyrazole-4-carboxylic acid;
(93) 1-[6-cyano-5-(3-ethoxyphenyl)pyridin-2-yl]-1H-pyrazole-4-carboxylic acid;
(94) 1-[6-cyano-5-(4-fluoro-3-methylphenyl)pyridin-2-yl]-1H-pyrazole-4-carboxylic acid;
(95) 1-[6-cyano-5-(2,6-difluorophenyl)pyridin-2-yl]-1H-pyrazole-4-carboxylic acid;
(96) 1-[6-cyano-5-(2-fluoro-6-methoxyphenyl)pyridin-2-yl]-1H-pyrazole-4-carboxylic acid;
(97) 3-amino-1-(4-cyano-5-phenylpyridin-2-yl)-1H-pyrazole-4-carboxylic acid;
(98) 3-amino-1-[4-cyano-5-(2-fluorophenyl)pyridin-2-yl]-1H-pyrazole-4-carboxylic acid;
(99) 3-amino-1-[4-cyano-5-(4-fluorophenyl)pyridin-2-yl]-1H-pyrazole-4-carboxylic acid;
(100) 3-amino-1-[4-cyano-5-(4-chlorophenyl)pyridin-2-yl]-1H-pyrazole-4-carboxylic acid;
(101) 3-amino-1-[4-cyano-5-(3-methylphenyl)pyridin-2-yl]-1H-pyrazole-4-carboxylic acid;
(102) 3-amino-1-[4-cyano-5-(3-methoxyphenyl)pyridin-2-yl]-1H-pyrazole-4-carboxylic acid;
(103) 3-amino-1-[4-cyano-5-(2-fluoro-4-methylphenyl)pyridin-2-yl]-1H-pyrazole-4-carboxylic acid;
(104) 3-amino-1-[4-cyano-5-(2-fluoro-5-methylphenyl)pyridin-2-yl]-1H-pyrazole-4-carboxylic acid;
(105) 3-amino-1-[4-cyano-5-(2,4-difluorophenyl)pyridin-2-yl]-1H-pyrazole-4-carboxylic acid;
(106) 3-amino-1-[4-cyano-5-(4-fluoro-3-methylphenyl)pyridin-2-yl]-1H-pyrazole-4-carboxylic acid; and
(107) 3-amino-1-[4-cyano-5-(2-fluoro-5-methoxyphenyl)pyridine-2-yl]-1H-pyrazole-4-carboxylic acid;
or a pharmaceutically acceptable salt thereof.

15. A pharmaceutical composition comprising the compound according to claim 1, or a pharmaceutically acceptable salt thereof, and a pharmaceutically acceptable carrier.

16. A xanthine oxidase inhibitor comprising the compound according to claim 1, or a pharmaceutically acceptable salt thereof, as an active ingredient.

17. A therapeutic agent for gout, hyperuricemia, tumor lysis syndrome, urinary calculus, hypertension, dyslipidemia, diabetes, cardiovascular diseases such as arteriosclerosis or heart failure, renal diseases such as diabetic nephropathy, respiratory diseases such as chronic obstructive pulmonary disease, inflammatory bowel diseases, or autoimmune diseases, comprising the compound according to claim 1, or a pharmaceutically acceptable salt thereof, as an active ingredient.

18. A therapeutic agent for gout or hyperuricemia, comprising the compound according to claim 1, or a pharmaceutically acceptable salt thereof, as an active ingredient.

19. A compound represented by formula (II):

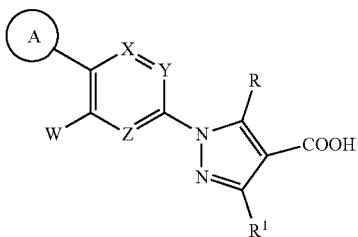
(II)

wherein:

A represents a $C_{6-10}$ aryl group or a heteroaryl group, wherein the aryl group or heteroaryl group may be unsubstituted or substituted with 1 to 3 groups Q which are the same or different from one another and selected from the group consisting of a halogen atom, —CN, —$NO_2$, a $C_{1-6}$ alkyl group, a $C_{3-7}$ cycloalkyl group, a $C_{1-6}$ halogenoalkyl group, a phenyl group, —$CH_2$—O—$R^2$, —O—$R^2$, —O—$C_{1-6}$ halogenoalkyl, —O-benzyl, —O-phenyl, —O—CO—$R^2$, —$NR^3R^4$, —NH—CO—$R^2$, —$CO_2$—$R^2$, —CO—$R^2$, —CO—$NR^3R^4$, —NH—$SO_2$—$R^2$, —CO-aryl, —S—$R^2$, —$SO_2$—$C_{1-6}$ alkyl, and —$SO_2$-phenyl;

X, Y, and Z represent $CR^5$ or a nitrogen atom, wherein one of X, Y, and Z represents a nitrogen atom and the remaining two represent $CR^5$;

R represents a hydrogen atom or a $C_{1-6}$ alkyl group;

$R^1$ represents a hydrogen atom, an amino group, or a $C_{1-6}$ alkyl group;

$R^2$ represents a hydrogen atom or a $C_{1-6}$ alkyl group;

$R^3$ and $R^4$ are the same or different from each other and are a hydrogen atom or a $C_{1-6}$ alkyl group, where $R^3$ and $R^4$ may be taken together to form with the nitrogen atom to which they are attached a nitrogen-containing saturated monocyclic heterocycle; and $R^5$ represents a hydrogen atom, a halogen atom, or a $C_{1-6}$ alkyl group;

$R^6$ represents a protective group of a carboxyl group; and

W represents a halogen atom, a methanesulfonyloxy group, a p-toluenesulfonyloxy group, a trifluoromethanesulfonyloxy group, or a cyano group.

* * * * *